US008362208B2

(12) United States Patent
Clegg et al.

(10) Patent No.: US 8,362,208 B2
(45) Date of Patent: Jan. 29, 2013

(54) IMMUNOGLOBULINS

(75) Inventors: Stephanie Jane Clegg, Stevenage (GB); Jonathan Henry Ellis, Stevenage (GB); Volker Germaschewski, Stevenage (GB); Paul Andrew Hamblin, Stevenage (GB); George Kopsidas, Melbourne (AU); Ruth McAdam, Stevenage (GB); Rabinder Kumar Prinjha, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 711 days.

(21) Appl. No.: 12/097,279

(22) PCT Filed: Dec. 14, 2006

(86) PCT No.: PCT/EP2006/069737
§ 371 (c)(1),
(2), (4) Date: Jun. 13, 2008

(87) PCT Pub. No.: WO2007/068750
PCT Pub. Date: Jun. 21, 2007

(65) Prior Publication Data
US 2010/0221260 A1    Sep. 2, 2010

(30) Foreign Application Priority Data

Dec. 16, 2005 (GB) .................................. 0525662.3

(51) Int. Cl.
| C07K 16/00 | (2006.01) |
| C12P 21/08 | (2006.01) |
| A61K 39/395 | (2006.01) |
| A61K 39/40 | (2006.01) |
| C07K 17/00 | (2006.01) |

(52) U.S. Cl. ............... 530/387.1; 530/387.3; 530/388.1; 530/388.25; 424/130.1; 424/133.1; 424/141.1; 424/152.1

(58) Field of Classification Search .......................... None
See application file for complete search history.

(56) References Cited

U.S. PATENT DOCUMENTS

| 6,420,388 B1 | 7/2002 | Emonds-Alt et al. |
| 7,780,964 B2 * | 8/2010 | Ellis et al. .................. 424/141.1 |
| 2005/0215770 A1 | 9/2005 | Bell |

FOREIGN PATENT DOCUMENTS

| WO | WO 95/32948 A1 | 12/1995 |
| WO | WO 2004/052932 | 6/2004 |
| WO | WO 2005/014575 A1 | 2/2005 |
| WO | WO 2005/028508 | 3/2005 |
| WO | WO 2005/016545 A2 | 7/2005 |
| WO | WO 2005/061544 * | 7/2005 |
| WO | WO 2005/061544 | 9/2005 |

OTHER PUBLICATIONS

Rudikoff et al. PNAS 1982 vol. 79, pp. 1979-1983.*
Rader et al. PNAS. 1998. 95:8910-8915.*
Coleman et al. Research in Immunology, 1994; 145(1): 33-36.*
Bareyre, et al., Journal of Neuroscience, No. 16, pp. 7097-7110, Aug. 15, 2002.
Caroni, et al., Neuron, vol. 1, pp. 85-96, Mar. 1988.
Casset, et al., Biochemical and Biophysical Research, vol. 307 (2003) pp. 198-205.
Chen, et al., J.Mol. Biol., (1999) 293, 865-881.
DePascalis, et al., Journal of Immnunolgy, 2002, 169: 3076-3084.
Emerick, et al., The Journal of Neuroscience, Jun. 15, 2003, 23(12):4826-4830.
Fiedler, et al., Protein Engineering, vol. 15, No. 11, pp. 931-941, 2002.
Fouad, at al., Brain Research Reviews, 36 (2001), pp. 204-212.
Giardina, et al., Journal Medicinal Chemistry, 42(6), 1053-1065, Mar. 2, 1999.
Glick, et al., Annals Internal Med., 2001, 134:47-60.
MacCallum, et al., Journal of Molecular Biology, (1996) 262, 732-745.
Pemberton, et al., Neuroscience 2003 Abstract.
Reindl, et al., Journal of Neuroimmunology, 145 (2003) 139-147.
Schmidlin, et al., Society for Neuroscience. Program No. 275.9 Abstract 2003 Online.
Schwab, et al., Society for Neuroscience, Program No. 678.9 Abstract 2003 Online.
Schnell. et al., Society for Neuroscience, Program No. 678.5 Abstract 2003 Online.
Vajdos, et al., J. Mol. Biol. (2002) 320, 415-428.
Wiessner, et al., Journal of Cerebral Blood Flow & Metabolism, 23:154-165 2003.
Wu, et al., J. Mol. Biol. (1999) 294, 151-162.
Zander, et al., Journal of Molecular Recognition, 20, 185-196, 2007.

* cited by examiner

*Primary Examiner* — Chun Dahle
(74) *Attorney, Agent, or Firm* — Jonathan M. Dermott; William M. Han; Carl W. Battle

(57) ABSTRACT

The present invention relates to antibodies to NOGO, pharmaceutical formulations containing them and to the use of such antibodies in the treatment and/or prophylaxis of neurological diseases/disorder.

2 Claims, 18 Drawing Sheets

IMMUNOGLOBULINS

This application is the US National Stage of International Application No. PCT/EP2006/069737, filed 14 Dec. 2006, which is incorporated herein by reference. This application also claims benefit of the filing date of GB 0525662.3, filed 16 Dec. 2005.

FIELD OF THE INVENTION

The present invention relates to immunoglobulins, particularly antibodies that bind to NOGO and neutralise the activity thereof, polynucleotides encoding such antibodies, pharmaceutical formulations containing said antibodies and to the use of such antibodies in the treatment and/or prophylaxis of neurological diseases. Other aspects, objects and advantages of the present invention will become apparent from the description below.

BACKGROUND OF THE INVENTION

Stroke is a major cause of death and disability in the Western World. There is no approved therapy for the treatment of stroke other than tissue plasminogen (t-PA) which has to be administered within 3 hours of onset following a computer tomography (CT) scan to exclude hemorrhage. To date most therapeutic agents directed towards the treatment of acute stroke (i.e. neuroprotection), have predominantly involved targeting glutamate receptors and their down stream signalling pathways known to be involved in acute cell death. However to date these strategies have proved unsuccessful in clinical trials and are often associated with dose-limiting side effects (Hill & Hachinski, The Lancet, 352: (suppl III) 10-14 (1998)). Therefore there is a need for novel approaches directed towards the amelioration of cell death following the cessation of blood flow. Neuroprotection is the ability of a treatment to prevent or ameliorate neuronal cell loss in response to an insult or disease process. This may be achieved by targeting the neurons directly or indirectly by preventing glial (including oligodendrocyte) cell loss.

Following the onset of stroke, some degree of spontaneous functional recovery is observed in many patients, suggesting that the brain has the (albeit limited) ability to repair and/or remodel following injury. Agents that have the potential to enhance this recovery may therefore allow intervention to be made much later (potentially days) following the onset of cerebral ischaemia. Agents which are able to offer both acute neuroprotection and enhance functional recovery may provide significant advantages over current potential neuroprotective strategies.

Alzheimer's disease (AD) is characterised by the presence of two diagnostic features of pathology. These are amyloid plaques and neurofibrillary tangles composed of aggregated beta-amyloid peptide (Aβ40 and Aβ42) and hyperphosphorylated tau respectively (Dawbarn & Allen 2001 Neurobiology of Alzheimer's Disease OUP).

A comprehensive study has shown a strong link in patients between beta-amyloid accumulation and cognitive decline (Naslund et al, JAMA, Mar. 22/29, 2000, Vol. 283, No; 12, page 1571-1577). This is consistent with genetic and epidemiological studies that suggest that some mutations in APP and presenilin genes can predispose to early onset AD, which mutations also enhance the levels of Aβ40 and Aβ42 peptide, including the ratio thereof.

Cleavage of the type I transmembrane amyloid precursor protein (APP) by two distinct proteases designated beta- and gamma-secretase is necessary for the formation of beta-amyloid peptide. The molecular identity of beta-secretase as the aspartyl-protease Asp2/BACE1 has been confirmed (Hussain et al Mol. Cell. NeuroSci. 16, 609-619 (2000); Vassar et al, Science (1999), Oct. 22; 286 (5440):735-741). The nature of gamma-secretase remains the source of some debate and is likely to consist of a high molecular weight complex consisting of at least the following proteins: presenilins, Aph1, Pen2 and nicastrin (reviewed in Medina & Dotti Cell Signalling 2003 15(9):829-41).

The processing of APP within the CNS is likely to occur within a number of cell-types including neurons, oligodendrocytes, astrocytes and microglia. While the overall rate of APP processing in these cells will be influenced by the relative level of expression of APP, BACE1/Asp2, presenilin-1 and -2, Aph1, Pen2 and nicastrin.

Furthermore, additional factors regulating the subcellular location of APP can also influence its processing as shown by the finding that mutation of the YENP motif in the APP cytoplasmic domain which blocks its endocytosis reduces beta-amyloid production (Perez et al 1999 J Biol Chem 274 (27) 18851-6). Retention of the APP-beta-CTF in the ER by the addition of the KKQN retention motif is sufficient to reduce amyloid production in transfected cells (Maltese et al 2001 J Biol Chem 276 (23) 20267-20279). Conversely, elevation of endocytosis, by overexpression of Rab5 is sufficient to elevate amyloid secretion from transfected cells (Grbovic et al 2003 J Biol Chem 278 (33) 31261-31268).

Consistent with these findings further studies have shown that reduction of cellular cholesterol levels (a well known risk factor for AD) reduced beta-amyloid formation. This change was dependent on altered endocytosis as demonstrated by the use of the dominant negative dynamin mutants (K44A) and overexpression of the Rab5 GTPase activating protein RN-Tre (Ehehalt et al 2003 J Cell Biol 160 (1) 113-123).

Cholesterol rich microdomains or rafts are also an important cellular site of beta-amyloid production and APP, BACE1 and components of the gamma-secretase complex have all been shown to transiently reside within rafts. Antibody cross-linking of APP and BACE1 towards cholesterol rich rafts was able to elevate beta-amyloid production (Ehehalt et al 2003 J Cell Biol 160 (1) 113-123). Expression of GPI-anchored BACE1, which is exclusively targeted to lipid rafts, is similarly able to elevate APP cleavage and beta-amyloid production (Cordy et al 2003 PNAS 100 (20) 11735-11740).

The mechanisms underlying functional recovery after a stroke or other neurodamaging event or disease, are currently unknown. The sprouting of injured or non-injured axons has been proposed as one possible mechanism. However, although in vivo studies have shown that treatment of spinal cord injury or stroke with neurotrophic factors results in enhanced functional recovery and a degree of axonal sprouting, these do not prove a direct link between the degree of axonal sprouting and extent of functional recovery (Jakeman, et al. 1998, Exp. Neurol. 154: 170-184, Kawamata et al. 1997, Proc Natl Acad. Sci. USA, 94:8179-8184, Ribotta, et al. 2000, J. Neurosci. 20: 5144-5152). Furthermore, axonal sprouting requires a viable neuron. In diseases such as stroke which is associated with extensive cell death, enhancement of functional recovery offered by a given agent post stroke may therefore be through mechanisms other than axonal sprouting such as differentiation of endogenous stem cells, activation of redundant pathways, changes in receptor distribution or excitability of neurons or glia (Fawcett & Asher, 1999, Brain Res. Bulletin, 49: 377-391, Horner & Gage, 2000, Nature 407 963-970).

The limited ability of the central nervous system (CNS) to repair following injury is thought in part to be due to molecules within the CNS environment that have an inhibitory effect on axonal sprouting (neurite outgrowth). CNS myelin is thought to contain inhibitory molecules (Schwab M E and Caroni P (1988) J. Neurosci. 8, 2381-2193). Two myelin proteins, myelin-associated glycoprotein (MAG) and NOGO have been cloned and identified as putative inhibitors of neurite outgrowth (Sato S. et al (1989) Biochem. Biophys. Res. Comm. 163, 1473-1480; McKerracher L et al (1994) Neuron 13, 805-811; Mukhopadhyay G et al (1994) Neuron 13, 757-767; Torigoe K and Lundborg G (1997) Exp. Neurology 150, 254-262; Schafer et al (1996) Neuron 16, 1107-1113; WO9522344; WO9701352; Prinjha R et al (2000) Nature 403, 383-384; Chen M S et al (2000) Nature 403, 434-439; GrandPre T et al (2000) Nature 403, 439-444; US005250414A; WO200005364A1; WO0031235).

Three forms of human NOGO have been identified: NOGO-A having 1192 amino acid residues (GenBank accession no. AJ251383); NOGO-B, a splice variant which lacks residues 186 to 1004 in the putative extracellular domain (GenBank accession no. AJ251384) and a shorter splice variant, NOGO-C, which also lacks residues 186 to 1004 and also has smaller, alternative amino terminal domain (GenBank accession no. AJ251385) (Prinjha et al (2000) supra).

Inhibition of the CNS inhibitory proteins such as NOGO may provide a therapeutic means to ameliorate neuronal damage and promote neuronal repair and growth thereby potentially assisting recovery from neuronal injury such as that sustained in stroke. Examples of such NOGO inhibitors may include small molecules, peptides and antibodies.

It has been reported that a murine monoclonal antibody, IN-1, that was raised against NI-220/250, a myelin protein which is a potent inhibitor of neurite growth (and subsequently shown to be fragment of NOGO-A), promotes axonal regeneration (Caroni, P and Schwab, M E (1988) Neuron 1 85-96; Schnell, L and Schwab, M E (1990) Nature 343 269-272; Bregman, B S et al (1995) Nature 378 498-501 and Thallmair, M et al (1998) Nature Neuroscience 1 124-131). It has also been reported that NOGO-A is the antigen for IN-1 (Chen et at (2000) Nature 403 434-439). Administration of IN-1 Fab fragment or humanised IN-1 to rats that have undergone spinal cord transection, enhanced recovery (Fiedler, M et al (2002) Protein Eng 15 931-941; Brosamle, C et al (2000) J. Neuroscience 20 8061-8068).

Monoclonal antibodies which bind to NOGO are described in WO 04/052932 and WO2005028508. WO 04/052932 discloses a murine antibody 11C7 which binds to certain forms of human NOGO with high affinity.

Patent application WO05/061544 also discloses high affinity monoclonal antibodies, including a murine monoclonal antibody 2A10, and generally discloses humanised variants thereof, for example H1 L11 (the sequences for the H1 and L11 are provided in SEQ ID NOs. 33 and 34 respectively (VH or VL sequences only)). The antibodies disclosed bind to human NOGO-A with high affinity. The murine 2A10 antibody (and CDR-grafted humanised variants thereof) are characterised by the following complementarity determining region (CDR) sequences (as determined using the Kabat methodology (Kabat et al. (1991) "Sequences of proteins of immunological interest"; Fifth Edition; US Department of Health and Human Services; NIH publication No 91-3242)) within their light and heavy chain variable regions:

TABLE 1

Antibody 2A10 light chain CDRs

| CDR | Sequence |
|---|---|
| L1 | RSSKSLLYKDGKTYLN (SEQ ID NO: 4) |
| L2 | LMSTRAS (SEQ ID NO: 5) |
| L3 | QQLVEYPLT (SEQ ID NO: 6) |

TABLE 2

Antibody 2A10 heavy chain CDRs

| CDR | Sequence |
|---|---|
| H1 | SYWMH (SEQ ID NO: 1) |
| H2 | NINPSNGGTNYNEKFKS (SEQ ID NO: 2) |
| H3 | GQGY (SEQ ID NO: 3) |

WO05/061544 further discloses "analogues" of the antibodies that comprise the CDRs of Tables 1 and 2 above, such "analogues" the have same antigen binding specificity and/or neutralizing ability as the donor antibody from which they were derived.

Despite the art providing high affinity anti-NOGO antibodies, it remains a highly desirable goal to isolate and develop alternative, or improved, therapeutically useful monoclonal antibodies that bind and inhibit the activity of human NOGO.

The process of neurodegeneration underlies many neurological diseases/disorders including, but not limited to, acute diseases such as stroke (ischemic or haemorrhagic), traumatic brain injury and spinal cord injury as well as chronic diseases including Alzheimer's disease, fronto-temporal dementias (tauopathies), peripheral neuropathy, Parkinson's disease, Creutzfeldt-Jakob disease (CJD), Schizophrenia, amyotrophic lateral sclerosis (ALS), multiple sclerosis, Huntington's disease, multiple sclerosis and inclusion body myositis. Consequently the anti-NOGO monoclonal antibodies, and the like, of the present invention may be useful in the treatment of these diseases/disorders. Antibodies for the treatment of the above mentioned disease/disorders are provided by the present invention and described in detail below.

BRIEF SUMMARY OF THE INVENTION

The invention provides specific heavy chain variable regions, and antibodies or fragments thereof comprising the said specific heavy chain variable regions and a light chain variable region that allows, when paired with the heavy chain variable regions, the Fv dimer to bind human NOGO-A with high affinity, and thereby neutralise the activity of human NOGO-A.

The heavy chain variable regions of the present invention may be formatted, together with light chain variable regions to allow binding to human NOGO-A, in the conventional immunoglobulin manner (for example, human IgG, IgA, IgM etc.) or in any other fragment thereof or "antibody-like" format that binds to human NOGO-A (for example, single chain Fv, diabodies, Tandabs™ etc (for a summary of alternative "antibody" formats see Holliger and Hudson, Nature Biotechnology, 2005, Vol 23, No. 9, 1126-1136)).

A heavy chain variable region comprising a third CDR consisting essentially of the amino acid residues GQGY wherein the CDR contains at least one substitution within the GQGY core sequence, the substitutions being selected from the following substitutions: where the G in the first position is replaced by R, I, W or M; the Q in the second position is replaced by D, I, A, L, V or S; the G in the third position is replaced by W, N, Y, S, L or F; and the Y in the fourth position is replaced by W.

In another embodiment, the third heavy chain CDR (CDR H3) only contains one substitutions to yield the following CDR H3: RQGY (SEQ ID NO.75), IQGY (SEQ ID NO.76), MQGY (SEQ ID NO.45), GDGY (SEQ ID NO.77), GIGY (SEQ ID NO.78), GSGY (SEQ ID NO.79), GQNY (SEQ ID NO.80), GQYY (SEQ ID NO.81), GQSY (SEQ ID NO.62), GQLY (SEQ ID NO.82), GQFY (SEQ ID NO.83), GQGW (SEQ ID NO.84), WQGY (SEQ ID NO.86), GAGY (SEQ ID NO.87), GLGY (SEQ ID NO.88), GVGY (SEQ ID NO.89), GQWY (SEQ ID NO.90).

In another embodiment, the heavy chain variable regions above further contain the other CDRs listed in Table 2, i.e. CDR H1 (SEQ ID NO. 1) and CDR H2 (SEQ ID NO.2).

The antibodies of the present invention, or fragments thereof, retain the human NOGO binding activity of antibodies that comprise the CDR H3: GQGY, in terms of their activity as measured in ELISA and Biacore experiments, and in some cases the activity in these experiments is increased.

Human or Humanised Heavy Chain Variable Regions Containing G95M (Substitution numbering by Kabat)

In one embodiment of the present invention, the heavy chain variable regions of the present invention comprise the CDRs defined in Table 3 (as defined by Kabat):

TABLE 3

| CDR | Sequence |
|---|---|
| H1 | SYWMH (SEQ ID NO: 1) |
| H2 | NINPSNGGTNYNEKFKS (SEQ ID NO: 2) |
| H3 | MQGY (SEQ ID NO: 45) |

In one embodiment of the present invention there is provided a human or humanised heavy chain variable region comprising each of the CDRs listed in Table 3. In another embodiment of the present invention there is provided a humanised heavy chain variable region comprising the CDRs listed in Table 3 within the larger sequence of a human heavy chain variable region. In yet another embodiment the humanised heavy chain variable region comprises the CDRs listed in Table 3 within an acceptor antibody framework having greater than 40% identity in the framework regions, or greater than 50%, or greater than 60%, or greater than 65% identity to the murine 2A10 donor antibody heavy chain variable region (SEQ ID NO.7).

When the CDRs of Table 3 are all used, in one embodiment the heavy chain variable region sequence is sequence H98 provided as SEQ ID NO. 66 (H98 VH is the equivalent of H1 VH (SEQ ID NO.33) differing only in that the CDR H3 is MQGY in H98 instead of GQGY as found in H1).

In one aspect of the present invention the antibodies comprise a heavy chain variable region having the amino acid sequence of SEQ ID NO. 66 (H98 variable region) further comprising a number of substitutions at one or more of positions 38, 40, 48, 67, 68, 70, 72, 74, and 79; wherein each substituted amino acid residue is replaced with the amino acid residue at the equivalent position in SEQ ID NO 7 (the heavy chain variable region of the donor antibody 2A10) and the number of substitutions is between 1 and 9. In other embodiments the number of substitutions is 1, or 2, or 3, or 4, or 5, or 6, or 7, or 8 or 9.

In this context the substitutions that are described are equivalent in concept to "back-mutations" where the human framework amino acid residues in specific positions within the H98 sequence are back-mutated to the amino acid residues in the equivalent position within the 2A10 donor antibody sequence.

Unless specifically stated otherwise to the contrary herein, when a numerical position of an amino acid residue found within a specific sequence is mentioned in this document, for example "position 12", it is intended that the skilled reader assigns the first amino acid in the sequence the position "1" and counts from position one and identifies the amino acid which is in the desired position, in this example the twelfth amino acid residue in the sequence. The skilled reader will notice that this numbering system does not correspond with the Kabat numbering system which is often used to define amino acid positions within antibody sequences.

For optimal binding affinity, it was found for the humanisation of the mouse antibody 2A10 (the VH for which is SEQ ID NO. 7) that the pair of amino acid residues in positions 48 and 68, should be I and A respectively (as they exist in 2A10) or M and V respectively (as they exist in H98). It is expected that the above finding is also of relevance to the humanisation of the G95M variant of 2A10.

The following table includes details of three different heavy chain variable (VH) regions which may form part of the antibodies of the present invention. Each of the disclosed VH is based on the H98 VH (SEQ ID NO. 66) further comprising the substitutions mentioned in the table (Table 4) where the H98 residue at the relevant position is substituted with the 2A10 residue at that position (in the table, "-" means that there is no substitution in that position, and so the residue remains as in the sequence of H98):

TABLE 4

| | Numerical Residue No. | | | | | | | | |
|---|---|---|---|---|---|---|---|---|---|
| | 38 | 40 | 48 | 67 | 68 | 70 | 72 | 74 | 79 |
| | | | | Kabat No. | | | | | |
| | 38 | 40 | 48 | 66 | 67 | 69 | 71 | 73 | 78 |
| | | | | 2A10 | | | | | |
| New VH (SEQ ID NO. X) | K | R | I | K | A | L | V | K | A |
| | | | | H98 | | | | | |
| | R | A | M | R | V | M | R | T | V |
| H26 (47) | — | — | I | — | A | — | — | — | A |
| H27 (48) | K | R | I | K | A | L | V | K | A |
| H28 (49) | — | — | I | K | A | — | — | — | A |

In one embodiment of the present invention, therefore, the heavy chain variable regions (VH) of the present invention are H26 VH (SEQ ID NO. 47), H27 VH (SEQ ID NO. 48) and H28 VH (SEQ ID NO. 49)

SEQ ID 47: VH humanised construct H26
QVQLVQSGAEVKKPGASVKVSCKASGYTFTSYWMHWVRQAPGQGLEWIGN

INPSNGGTNYNEKFKSRATMTRDTSTSTAYMELSSLRSEDTAVYYCELMQ

GYWGQGTLVTVSS

SEQ ID 48: VH humanised construct H27
QVQLVQSGAEVKKPGASVKVSCKASGYTFTSYWMHWVKQRPGQGLEWIGN

INPSNGGTNYNEKFKSKATLTVDKSTSTAYMELSSLRSEDTAVYYCELMQ

GYWGQGTLVTVSS

SEQ ID 49: VH humanised construct H28
QVQLVQSGAEVKKPGASVKVSCKASGYTFTSYWMHWVRQAPGQGLEWIGN

INPSNGGTNYNEKFKSKATMTRDTSTSTAYMELSSLRSEDTAVYYCELMQ

GYWGQGTLVTVSS

Human or Humanised Heavy Chain Variable Regions Including G101S (Substitution Numbering by Kabat)

In another embodiment of the present invention there is provided a human or humanised heavy chain variable region which comprises CDRs defined in Table 5:

TABLE 5

| CDR | According to Kabat |
|-----|-------------------|
| H1  | SYWMH (SEQ ID NO: 1) |
| H2  | NINPSNGGTNYNEKFKS (SEQ ID NO: 2) |
| H3  | GQSY (SEQ ID NO: 62) |

In one embodiment the CDRs of Table 5 are incorporated within a human heavy chain variable region sequence. In another embodiment the humanised heavy chain variable region comprises the CDRs listed in Table 5 within an acceptor antibody framework having greater than 40% identity in the framework regions, or greater than 50%, or greater than 60%, or greater than 65% identity to the murine 2A10 donor antibody heavy chain variable region (SEQ ID NO.7).

In another embodiment the CDRs of Table 5 are inserted into a human heavy chain variable region to give the following sequence (H99): QVQLVQSGAEVKKPGASVKVSCK-ASGYTFTSYWMHWVRQAPGQGLEWMGNI NPSNG-GTNYNEKFKSRVTMTRDTSTSTVYMELSSLRSEDTAVYYCELGQSYW GQGTLVTVSS (SEQ ID 61: 2A10 VH humanised construct H99).

In other embodiments, further back mutations are added to the H99 VH sequence in any one of positions (denoted by numerical residue position) 38, 40, 48, 67, 68, 70, 72, 74 or 79; wherein each substituted amino acid residue is replaced with the amino acid residue at the equivalent position in SEQ ID NO 7 (the heavy chain variable region of the donor antibody 2A10) and the number of substitutions is between 1 and 9. In other embodiments the number of substitutions is 1, or 2, or 3, or 4, or 5, or 6, or 7, or 8 or 9. H99 VH is the equivalent of H1 VH (SEQ ID NO.33) differing only in that the CDR H3 is GQSY in H99 instead of GQGY as found in H1.

For optimal binding affinity, it was found for the humanisation of the mouse antibody 2A10 (the VH for which is SEQ ID NO. 7) that the pair of amino acid residues in positions 48 and 68, should be I and A respectively (as they exist in 2A10) or M and V respectively (as they exist in H98). It is expected that the above finding is also of relevance to the humanisation of the G95M variant of 2A10.

In one embodiment the back mutations are located in the positions indicated in Table 6 below where the H99 residue at the relevant position is substituted with the 2A10 residue at that position (in the table, "-" means that there is no substitution in that position, and so the residue remains as in the sequence of H1):

TABLE 6

| | Numerical Residue No. | | | | | | | | |
|---|---|---|---|---|---|---|---|---|---|
| | 38 | 40 | 48 | 67 | 68 | 70 | 72 | 74 | 79 |
| | | | | Kabat No. | | | | | |
| | 38 | 40 | 48 | 66 | 67 | 69 | 71 | 73 | 78 |
| | | | | 2A10 | | | | | |
| New VH (SEQ ID NO. X) | K | R | I | K | A | L | V | K | A |
| | | | | H99 | | | | | |
| | R | A | M | R | V | M | R | T | V |
| H100 (63) | — | — | I | — | A | — | — | — | A |
| H101 (64) | K | R | I | K | A | L | V | K | A |
| H102 (65) | — | — | I | K | A | — | — | — | A |

Antibodies or Fragments that Comprise the Human or Humanised Heavy Chain Variable Regions and Light Chain Variable Regions The VH constructs of the present invention may be paired with a light chain to form a human NOGO-A binding unit (Fv) in any format, including a conventional IgG antibody format having full length (FL) variable and constant domain heavy chain sequences. Examples of full length (FL) IgG1 heavy chain sequences comprising the VH constructs of the present invention and inactivating mutations in positions 235 and 237 (EU Index numbering) to render the antibody non-lytic are SEQ ID NOs 53, 54 and 55.

SEQ ID 53: Heavy chain humanised construct H26
MGWSCIILFLVATATGVHSQVQLVQSGAEVKKPGASVKVSCKASGYTFTS

YWMHWVRQAPGQGLEWIGNINPSNGGTNYNEKFKSRATMTRDTSTSTAYM

ELSSLRSEDTAVYYCELMQGYWGQGTLVTVSSASTKGPSVFPLAPSSKST

SGGTAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAPELA

GAPSVFLFPPKPKDTLMISRTPEVTCVVVDVSHEDPEVKFNWYVDGVEVH

NAKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESNG

QPENNYKTTPPVLDSDGSFFLYSKLTVDKSRWQQGNVFSCSVMHEALH

NHYTQKSLSLSPGK.

SEQ ID 54: Heavy chain humanised construct H27
MGWSCIILFLVATATGVHSQVQLVQSGAEVKKPGASVKVSCKASGYTFTS

YWMHWVKQRPGQGLEWIGNINPSNGGTNYNEKFKSKATLTVDKSTSTAY

MELSSLRSEDTAVYYCELMQGYWGQGTLVTVSSASTKGPSVFPLAPSSK

STSGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPCPA

PELAGAPSVFLFPPKPKDTLMISRTPEVTCVVVDVSHEDPEVKFNWYV

DGVEVHNAKTKPREEQYNSTYRVVSVLTVLHQDWLNGKEYKCKVSNKAL

PAPIEKTISKAKGQPREPQVYTLPPSRDELTKNQVSLTCLVKGFYPSDIA

VEWESNGQPENNYKTTPPVLDSDGSFFLYSKLTVDKSRWQQGNVFSCS

VMHEALHNHYTQKSLSLSPGK

-continued
SEQ ID 55: Heavy chain humanised construct H28
MGWSCIILFLVATATGVHSQVQLVQSGAEVKKPGASVKVSCKASGYTFTS

YWMHWVRQAPGQGLEWIGNINPSNGGTNYNEKFKSKATMTRDTSTSTAYM

ELSSLRSEDTAVYYCELMQGYWGQGTLVTVSSASTKGPSVFPLAPSSKS

TSGGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCPAP

ELAGAPSVFLFPPKPKDTLMISRTPEVTCVVVDVSHEDPEVKFNWYVDG

VEVHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHE

ALHNHYTQKSLSLSPGK

The light chain variable region sequence that forms an Fv with the heavy chain variable region sequences of the present invention may be any sequence that allows the Fv to bind to Human NOGO-A.

In one embodiment of the present invention the light chain variable region is the 2A10 light chain (see WO 05/061544), the light chain variable region of which is provided herein as SEQ ID NO. 8 or humanised variants thereof. Humanised variants of the 2A10 light chain preferably contain all of the light chain variable region CDRs that are described in Table 1 grafted onto a human light chain variable region acceptor framework. In one embodiment the humanised light chain variable regions are L11 (SEQ ID NO.34), L13 (SEQ ID NO.13) or L16 (SEQ ID NO.14). Alternative light chain variable regions that are based on L13 and L16, which comprise specific substitutions in kabat positions 37 and/or 45, are provided in Table 7.

L100, L101, L102, L103, L104, and L105. It is intended that all possible combinations of the listed heavy chain variable regions and light chain variable regions be specifically disclosed (e.g. H28L104 et. al.).

In particular embodiments the antibodies, fragments or functional equivalents thereof comprise the following variable region pairs:
H27L16 (SEQ ID NO.48+SEQ ID NO.14)
H28L13 (SEQ ID NO.49+SEQ ID NO.13)
H28L16 (SEQ ID NO.49+SEQ ID NO.14)

In another embodiment the antibodies of the present invention comprise the following full length sequences:
H27FL L16FL (SEQ ID NO. 54+SEQ ID NO.18)
H28FL L13FL (SEQ ID NO. 55+SEQ ID NO.17)
H28FL L16FL (SEQ ID NO. 55+SEQ ID NO.18)

In one embodiment the antibody of the present invention comprises H27L16 (SEQ ID NO.48+SEQ ID NO.14), or is the full length antibody H28FL L16FL (SEQ ID NO. 55+SEQ ID NO.18).

In another embodiment, the antibody or fragment thereof binds to the same human NOGO epitope as H28L16, or competes with the binding of H28L16 to human NOGO, characterised in both instances in that the competing antibody, or fragment thereof, is not the murine antibody 2A10 or a human or humanised variant thereof comprising a CDR H3 having the sequence GQGY (SEQ ID NO.3) or a sequence containing one amino acid substitution in the CDR H3.

In particular embodiments the antibodies, fragments or functional equivalents thereof comprise the following variable region pairs:
H100L16 (SEQ ID NO.63+SEQ ID NO.14)
H101L13 (SEQ ID NO.64+SEQ ID NO.13)
H102L16 (SEQ ID NO.65+SEQ ID NO.14)

TABLE 7

| Description | SEQ ID NO. | Sequence |
|---|---|---|
| L100 (L13 + Q37R) | 67 | DIVMTQSPLSLPVTLGQPASISCRSSKSLLYKDGKTYLNWFRQ RPGQSPQLLIYLMSTRASGVPDRFSGGGSGTDFTLKISRVEA EDVGVYYCQQLVEYPLTFGQGTKLEIK |
| L101 (L13 + Q45R) | 68 | DIVMTQSPLSLPVTLGQPASISCRSSKSLLYKDGKTYLNWFQQ RPGQSPRLLIYLMSTRASGVPDRFSGGGSGTDFTLKISRVEAE DVGVYYCQQLVEYPLTFGQGTKLEIK |
| L102 (L13 + Q37R/Q45R) | 69 | DIVMTQSPLSLPVTLGQPASISCRSSKSLLYKDGKTYLNWFRQ RPGQSPRLLIYLMSTRASGVPDRFSGGGSGTDFTLKISRVEAE DVGVYYCQQLVEYPLTFGQGTKLEIK |
| L103 (L16 + Q37R) | 70 | DIVMTQSPLSNPVTLGQPVSISCRSSKSLLYKDGKTYLNWFRQ RPGQSPQLLIYLMSTRASGVPDRFSGGGSGTDFTLKISRVEA EDVGVYYCQQLVEYPLTFGQGTKLEIK |
| L104 (L16 + Q45R) | 71 | DIVMTQSPLSNPVTLGQPVSISCRSSKSLLYKDGKTYLNWFLQ RPGQSPRLLIYLMSTRASGVPDRFSGGGSGTDFTLKISRVEAE DVGVYYCQQLVEYPLTFGQGTKLEIK |
| L105 (L16 + Q37R/Q45R) | 72 | DIVMTQSPLSNPVTLGQPVSISCRSSKSLLYKDGKTYLNWFRQ RPGQSPRLLIYLMSTRASGVPDRFSGGGSGTDFTLKISRVEAE DVGVYYCQQLVEYPLTFGQGTKLEIK |

In another embodiment the full length (FL) light chain sequences are L11 FL (SEQ ID NO.36), L13 FL (SEQ ID NO.17) or L16 FL (SEQ ID NO.18).

In another embodiment the antibodies, fragments or functional equivalents thereof comprise a VH sequence selected from H26, H27, H28, H100, H101 and H102; in combination with any one of the following VL sequences L11, L13, L16, Epitope Mapping and Further Antibodies that Bind to the Same Epitope In another embodiment there is provided an antibody, or fragment thereof, that is capable of binding to human NOGO protein, or fragment thereof such as as a GST-NOGO-A56 protein (SEQ ID NO.32), in an ELISA assay, wherein the binding of the antibody, or fragment thereof, to the human NOGO protein, or fragment thereof, in the ELISA assay is reduced in the presence of a peptide having the following sequence VLPDIVMEAPLN (SEQ ID NO. 60), and is not reduced in the presence of an irrelevant peptide, for instance a peptide from human NOGO that does not overlap with SEQ ID NO.60 (such as SEQ ID NO. 85, YESIKHEPENPP-PYEE), characterised in that the antibody or fragment thereof is not an antibody comprising a heavy chain variable domain having a CDR H3 consisting of the amino acid residues GQGY or analogues thereof having one amino acid substitution in the CDR H3. Alternatively the competing peptide is TPSPVLPDIVMEAPLN (SEQ ID NO. 73) or VLPDI-VMEAPLNSAVP (SEQ ID NO. 74). In addition, the antibody that binds to the same epitope as the antibodies, or fragments thereof, may be an antibody that does not comprise all of the CDRs listed in Tables 1 and 2, or any antibody that comprises a set of CDRs that has 80% or greater homology to the CDRs listed in Tables 1 and 2 combined, or Tables 1 or 2 alone.

In another embodiment of the present invention there is provided an antibody or fragment thereof, that is capable of binding in an ELISA assay to a region of human NOGO protein consisting of the polypeptide sequence of VLPDI-VMEAPLN (SEQ ID NO. 60), characterised in that the antibody, or fragment thereof is not an antibody comprising a variable heavy domain having CDR H3 consisting of the amino acid residues GQGY or analogues thereof having one amino acid substitution in the CDR H3. Alternatively the antibody or fragment thereof is capable of binding to TPSPV-LPDIVMEAPLN (SEQ ID NO. 73) or VLPDIVMEAPLN-SAVP (SEQ ID NO. 74). In addition, the antibody that binds to the same epitope as the antibodies, or fragments thereof, may be an antibody that does not comprise all of the CDRs listed in Tables 1 and 2, or any antibody that comprises a set of CDRs that has 80% or greater homology to the CDRs listed in Tables 1 and 2 combined, or Tables 1 or 2 alone.

In another embodiment of the present invention there is provided a method of obtaining an antibody, or binding fragment thereof, that binds to human NOGO epitope VLPDI-VMEAPLN (SEQ ID NO. 60), comprising immunising a mammal with said peptide and isolating cells capable of producing an antibody which binds to said peptide. In another embodiment of the present invention there is provided a method of obtaining an isolated antibody, or binding fragment thereof, that binds to human NOGO epitope VLPDI-VMEAPLN (SEQ ID NO. 60) comprising screening a library which comprises a plurality of antibodies or binding fragments thereof, each being isolatable from the library together with a nucleotide sequence that encodes the antibody or binding fragment thereof, by the binding of the antibody, or binding fragment thereof to the NOGO epitope VLPDI-VMEAPLN (SEQ ID NO. 60).

Pharmaceutical Compositions

A further aspect of the invention provides a pharmaceutical composition comprising an anti-NOGO antibody of the present invention or functional fragment or equivalent thereof together with a pharmaceutically acceptable diluent or carrier.

In a further aspect, the present invention provides a method of treatment or prophylaxis of stroke (particularly ischemic stroke) and other neurological diseases, in particular Alzheimer's disease, and treatment of a patient suffering from a mechanical trauma to the CNS (such as spinal chord injury), in a human which comprises administering to said human in need thereof an effective amount of an anti-NOGO antibody of the invention or functional fragments thereof.

In another aspect, the invention provides the use of an anti-NOGO antibody of the invention or a functional fragment thereof in the preparation of a medicament for treatment or prophylaxis of stroke (particularly ischemic stroke) and other neurological diseases, in particular Alzheimer's disease and treatment of a patient suffering from a mechanical trauma to the CNS (such as spinal chord injury).

In a further aspect, the present invention provides a method of inhibiting neurodegeneration and/or promoting functional recovery in a human patient afflicted with, or at risk of developing, a stroke (particularly ischemic stroke) or other neurological disease, in particular Alzheimer's disease, and treatment of a patient suffering from a mechanical trauma to the CNS (such as spinal chord injury), which comprises administering to said human in need thereof an effective amount of an anti-NOGO antibody of the invention or a functional fragment thereof.

In a yet further aspect, the invention provides the use of an anti-NOGO antibody of the invention or a functional fragment thereof in the preparation of a medicament for inhibiting neurodegeneration and/or promoting functional recovery in a human patient afflicted with, or at risk of developing, a stroke and other neurological disease, in particular Alzheimer's disease and treatment of a patient suffering from a mechanical trauma to the CNS (such as spinal chord injury).

Other aspects and advantages of the present invention are described further in the detailed description and the preferred embodiments thereof.

DETAILED DESCRIPTION OF THE INVENTION

Figure 1:
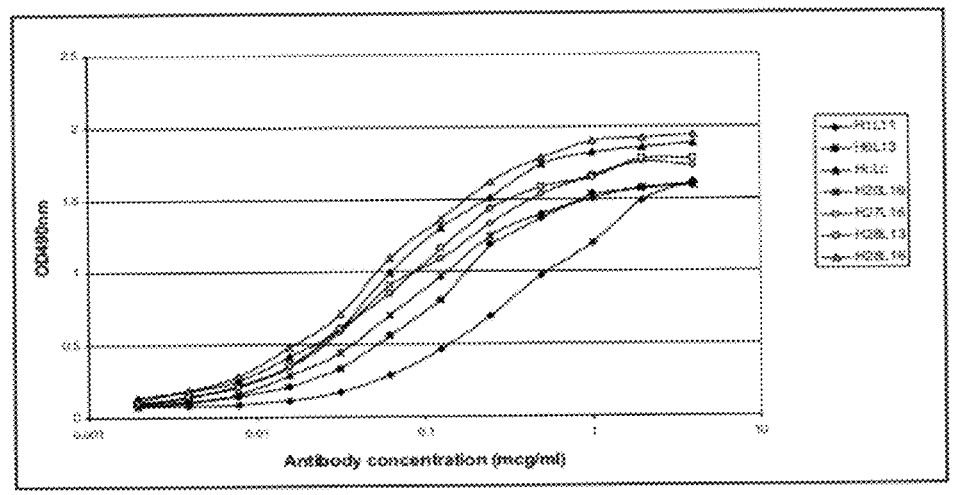
FIG. 1: GST-human NOGO-A56 coated at 1.0mcg/ml. ELISA on purified antibodies.
Figure 2:
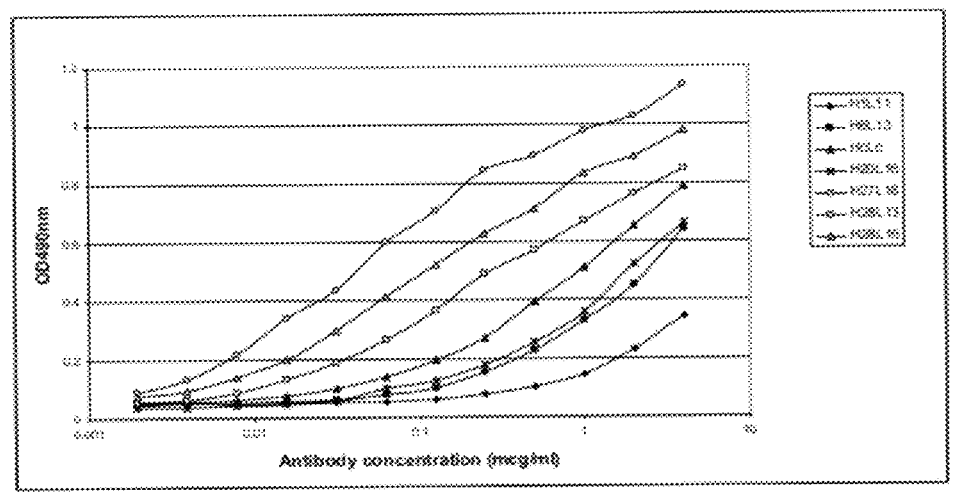
FIG. 2: GST-human NOGO-A56 coated at 0.05mcg/ml. ELISA on purified antibodies.
Figure 3:
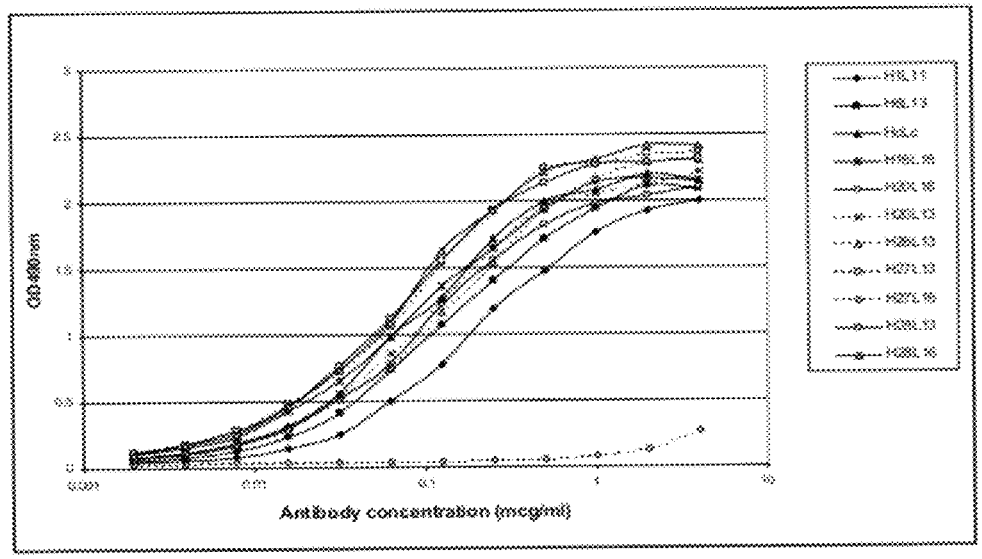
FIG. 3: GST-human NOGO-A56 coated at 1.0mcg/ml. ELISA on purified antibodies.
Figure 4:
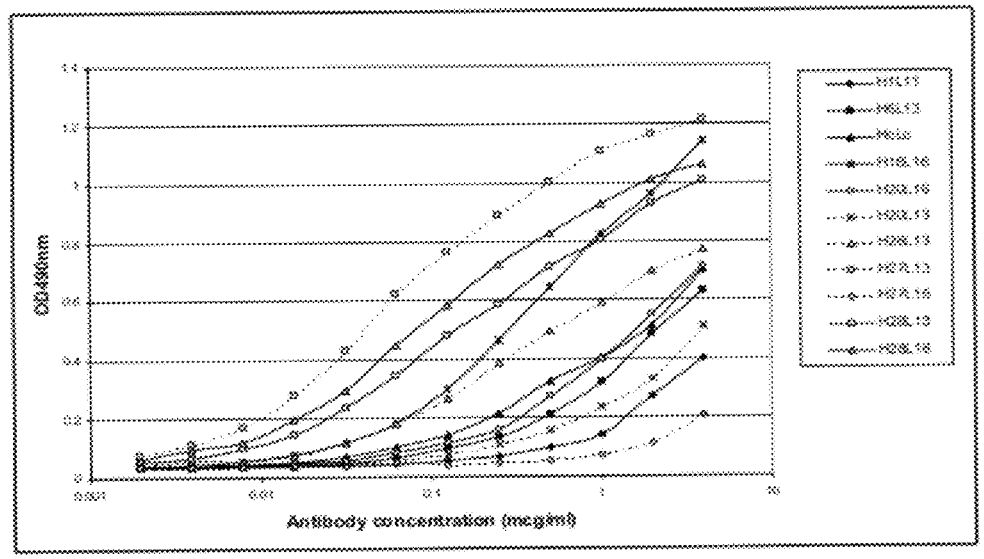
FIG. 4: GST-human NOGO-A56 coated at 0.05 mcg/ml. ELISA on purified antibodies.

The heavy chain variable regions of the invention may be formatted into the structure of a natural antibody or functional fragment or equivalent thereof. The antibody may therefore comprise the VH regions of the invention formatted into a full length antibody, a (Fab')$_2$ fragment, a Fab fragment, or equivalent thereof (such as scFV, bi- tr- or tetra-bodies, Tandabs, etc.), when paired with an appropriate light chain. The antibody may be an IgG1, IgG2, IgG3, or IgG4; or IgM; IgA, IgE or IgD or a modified variant thereof. The constant domain of the antibody heavy chain may be selected accordingly. The light chain constant domain may be a kappa or lambda constant domain. Furthermore, the antibody may comprise modifications of all classes eg IgG dimers, Fc mutants that no longer bind Fc receptors or mediate C1q binding. The antibody may also be a chimeric antibody of the type described in WO86/01533 which comprises an antigen binding region and a non-immunoglobulin region.

The constant region is selected according to the functionality required. Normally an IgG1 will demonstrate lytic ability through binding to complement and/or will mediate ADCC (antibody dependent cell cytotoxicity). An IgG4 will be preferred if a non-cytotoxic blocking antibody is required. However, IgG4 antibodies can demonstrate instability in production and therefore it may be more preferable to modify the generally more stable IgG1. Suggested modifications are described in EP0307434 preferred modifications include at positions 235 and 237. The invention therefore provides a lytic or a non-lytic form of an antibody according to the invention.

In preferred forms therefore the antibody of the invention is a full length (i.e. H2L2 tetramer) non-lytic IgG1 antibody having the heavy chain variable regions described herein.

In a further aspect, the invention provides polynucleotides encoding the heavy chain variable regions as described herein.

"NOGO" refers to any NOGO polypeptide, including variant forms. This includes, but is not limited to, NOGO-A having 1192 amino acid residues (GenBank accession no. AJ251383); NOGO-B, a splice variant which lacks residues 186 to 1004 in the putative extracellular domain (GenBank accession no. AJ251384) and a shorter splice variant, NOGO-C, which also lacks residues 186 to 1004 and also has smaller, alternative amino terminal domain (GenBank accession no. AJ251385) (Prinjha et al (2000) supra). All references to "NOGO" herein is understood to include any and all variant forms of NOGO such as NOGO-A and the splice variants described, unless a specific form is indicated.

"Neutralising" and grammatical variations thereof refers to inhibition, either total or partial, of NOGO function including its binding to neurones and inhibition of neurite growth.

The terms Fv, Fc, Fd, Fab, or F(ab)$_2$ are used with their standard meanings (see, e.g., Harlow et al., Antibodies A Laboratory Manual, Cold Spring Harbor Laboratory, (1988)).

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., Queen et al., Proc. Natl. Acad Sci USA, 86:10029-10032 (1989), Hodgson et al., Bio/Technology, 9:421 (1991)). A suitable human acceptor antibody may be one selected from a conventional database, e.g., the KABAT® database, Los Alamos database, and Swiss Protein database, by homology to the nucleotide and amino acid sequences of the donor antibody (in this case the murine donor antibody 2A10). A human antibody characterized by a homology to the framework regions of the donor antibody (on an amino acid basis) may be suitable to provide a heavy chain constant region and/or a heavy chain variable framework region for insertion of the donor CDRs (see Table 1 for the 2A10 CDRs for insertion into the acceptor framework). A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanised antibodies—see for example EP-A-0239400 and EP-A-054951.

The term "donor antibody" refers to a non-human antibody which contributes the amino acid sequences of its variable regions, CDRs, or other functional fragments or analogs thereof to the humanised antibody, and thereby provide the humanised antibody with the antigenic specificity and neutralizing activity characteristic of the donor antibody.

The term "acceptor antibody" refers to an antibody heterologous to the donor antibody, which provides the amino acid sequences of its heavy and/or light chain framework regions and/or its heavy and/or light chain constant regions to the humanised antibody. The acceptor antibody may be derived from any mammal provided that it is non-immunogenic in humans. Preferably the acceptor antibody is a human antibody.

Alternatively, humanisation may be achieved by a process of "veneering". A statistical analysis of unique human and murine immunoglobulin heavy and light chain variable regions revealed that the precise patterns of exposed residues are different in human and murine antibodies, and most individual surface positions have a strong preference for a small number of different residues (see Padlan E. A. et al; (1991) Mol. Immunol. 28, 489-498 and Pedersen J. T. et al (1994) J. Mol. Biol. 235; 959-973). Therefore it is possible to reduce the immunogenicity of a non-human Fv by replacing exposed residues in its framework regions that differ from those usually found in human antibodies. Because protein antigenicity can be correlated with surface accessibility, replacement of the surface residues may be sufficient to render the mouse variable region "invisible" to the human immune system (see also Mark G. E. et al (1994) in *Handbook of Experimental Pharmacology vol. 113: The pharmacology of monoclonal Antibodies*, Springer-Verlag, pp 105-134). This procedure of humanisation is referred to as "veneering" because only the surface of the antibody is altered, the supporting residues remain undisturbed. A further alternative approach is set out in WO04/006955.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883.

A bispecific antibody is an antibody having binding specificities for at least two different epitopes. Methods of making such antibodies are known in the art. Traditionally, the recombinant production of bispecific antibodies is based on the coexpression of two immunoglobulin H chain-L chain pairs, where the two H chains have different binding specificities see Millstein et al, Nature 305 537-539 (1983), WO93/08829 and Traunecker et al EMBO, 10, 1991, 3655-3659. Because of the random assortment of H and L chains, a potential mixture of ten different antibody structures are produced of which only one has the desired binding specificity. An alternative approach involves fusing the variable domains with the desired binding specificities to heavy chain constant region comprising at least part of the hinge region, CH2 and CH3 regions. It is preferred to have the CH1 region containing the site necessary for light chain binding present in at least one of the fusions. DNA encoding these fusions, and if desired the L chain are inserted into separate expression vectors and are then cotransfected into a suitable host organism. It is possible though to insert the coding sequences for two or all three chains into one expression vector. In one preferred approach, the bispecific antibody is composed of a H chain with a first binding specificity in one arm and a H-L chain pair, providing a second binding specificity in the other arm, see WO94/04690. See also Suresh et al Methods in Enzymology 121, 210, 1986.

In one embodiment of the invention there is provided a bispecific therapeutic antibody wherein at least one binding specificity of said antibody binds to human NOGO at the epitope described in SEQ ID NO. 60. In another embodiment of the present invention the bispecific antibody comprises the heavy chain variable region CDR H3 sequence MQGY (SEQ ID NO. 45). In another embodiment the bispecific antibody comprises the following pairs of heavy and light chain variable regions: H27L16 (SEQ ID NO.48+SEQ ID NO.14), H28L13 (SEQ ID NO.49+SEQ ID NO.13) or H28L16 (SEQ ID NO.49+SEQ ID NO.14).

The antibodies of the present invention may be produced by transfection of a host cell with an expression vector comprising the coding sequence for the antibodies of the invention. An expression vector or recombinant plasmid is produced by placing these coding sequences for the antibody in operative association with conventional regulatory control sequences capable of controlling the replication and expression in, and/or secretion from, a host cell. Regulatory sequences include promoter sequences, e.g., CMV promoter, and signal sequences, which can be derived from other known antibodies. Similarly, a second expression vector can be produced having a DNA sequence which encodes a complementary antibody light or heavy chain. Preferably this second expression vector is identical to the first except insofar as the coding sequences and selectable markers are concerned, so to ensure as far as possible that each polypeptide chain is functionally expressed. Alternatively, the heavy and light chain coding sequences for the altered antibody may reside on a single vector.

A selected host cell is co-transfected by conventional techniques with both the first and second vectors (or simply transfected by a single vector) to create the transfected host cell of the invention comprising both the recombinant or synthetic light and heavy chains. The transfected cell is then cultured by conventional techniques to produce the engineered antibody of the invention. The antibody which includes the association of both the recombinant heavy chain and/or light chain is screened from culture by appropriate assay, such as ELISA or RIA. Similar conventional techniques may be employed to construct other altered antibodies and molecules.

One useful expression system is a glutamate synthetase system (such as sold by Lonza Biologics), particularly where the host cell is CHO or NS0 (see below). Polynucleotide encoding the antibody is readily isolated and sequenced using conventional procedures (e.g. oligonucleotide probes). Vectors that may be used include plasmid, virus, phage, transposons, minichromsomes of which plasmids are a typical embodiment. Generally such vectors further include a signal sequence, origin of replication, one or more marker genes, an enhancer element, a promoter and transcription termination sequences operably linked to the light and/or heavy chain polynucleotide so as to facilitate expression. Polynucleotide encoding the light and heavy chains may be inserted into separate vectors and introduced (e.g. by electroporation) into the same host cell or, if desired both the heavy chain and light chain can be inserted into the same vector for transfection into the host cell. Thus according to one embodiment of the present invention there is provided a process of constructing a vector encoding the light and/or heavy chains of a therapeutic antibody or antigen binding fragment thereof of the invention, which method comprises inserting into a vector, a polynucleotide encoding either a light chain and/or heavy chain of a therapeutic antibody of the invention.

In another embodiment there is provided a polynucletotide encoding a humanised heavy chain variable region having the sequence set forth as SEQ. ID. NO: 47, 48 or 49.

In another embodiment there is provided a polynucleotide encoding a humanised heavy chain having the sequence set forth as SEQ.I.D.NO: 53, 54 or 55.

It will be immediately apparent to those skilled in the art that due to the redundancy of the genetic code, alternative polynucleotides to those disclosed herein are also available that will encode the polypeptides of the invention.

Suitable vectors for the cloning and subcloning steps employed in the methods and construction of the compositions of this invention may be selected by one of skill in the art. For example, the conventional pUC series of cloning vectors may be used. One vector, pUC19, is commercially available from supply houses, such as Amersham (Buckinghamshire, United Kingdom) or Pharmacia (Uppsala, Sweden). Additionally, any vector which is capable of replicating readily, has an abundance of cloning sites and selectable genes (e.g., antibiotic resistance), and is easily manipulated may be used for cloning. Thus, the selection of the cloning vector is not a limiting factor in this invention.

Other preferable vector sequences include a poly A signal sequence, such as from bovine growth hormone (BGH) and the betaglobin promoter sequence (betaglopro). The expression vectors useful herein may be synthesized by techniques well known to those skilled in this art. Typical selection genes encode proteins that (a) confer resistance to antibiotics or other toxins e.g. ampicillin, neomycin, methotrexate or tetracycline or (b) complement auxotrophic deficiencies or supply nutrients not available in the complex media. The selection scheme may involve arresting growth of the host cell. Cells, which have been successfully transformed with the genes encoding the therapeutic antibody of the present invention, survive due to e.g. drug resistance conferred by the selection marker. Another example is the so-called DHFR selection marker wherein transformants are cultured in the presence of methotrexate. CHO cells are a particularly useful cell line for the DHFR selection. Methods of selecting transformed host cells and amplifying the cell copy number of the transgene include using the DHFR system see Kaufman R. J. et al J. Mol. Biol. (1982) 159, 601-621, for review, see Werner R G, Noe W, Kopp K, Schluter M, "Appropriate mammalian expression systems for biopharmaceuticals", Arzneimittel-Forschung. 48(8):870-80, 1998 Aug. A further example is the glutamate synthetase expression system (Lonza Biologics). A suitable selection gene for use in yeast is the trp1 gene; see Stinchcomb et al Nature 282, 38, 1979.

The components of such vectors, e.g. replicons, selection genes, enhancers, promoters, signal sequences and the like, may be obtained from commercial or natural sources or synthesized by known procedures for use in directing the expression and/or secretion of the product of the recombinant DNA in a selected host. Other appropriate expression vectors of which numerous types are known in the art for mammalian, bacterial, insect, yeast, and fungal expression may also be selected for this purpose.

The present invention also encompasses a cell line transfected with a recombinant plasmid containing the coding sequences of the antibodies or equivalents of the present invention. Host cells useful for the cloning and other manipulations of these cloning vectors are also conventional. However, most desirably, cells from various strains of *E. coli* are used for replication of the cloning vectors and other steps in the construction of altered antibodies of this invention.

Suitable host cells or cell lines for the expression of the antibody of the invention are preferably mammalian cells such as NS0, Sp2/0, CHO (e.g. DG44), COS, a fibroblast cell (e.g., 3T3), and myeloma cells, and more preferably a CHO or a myeloma cell. Human cells may be used, thus enabling the molecule to be modified with human glycosylation patterns. Alternatively, other eukaryotic cell lines may be employed. The selection of suitable mammalian host cells and methods for transformation, culture, amplification, screening and product production and purification are known in the art. See, e.g., Sambrook et al., cited above.

Bacterial cells may prove useful as host cells suitable for the expression of the antibodies or fragments thereof (such as recombinant Fabs or ScFvs) of the present invention (see, e.g., Plückthun, A., Immunol. Rev., 130:151-188 (1992)). However, due to the tendency of proteins expressed in bacterial cells to be in an unfolded or improperly folded form or in a non-glycosylated form, any recombinant fragment produced in a bacterial cell would have to be screened for retention of antigen binding ability. If the molecule expressed by the bacterial cell was produced in a properly folded form, that bacterial cell would be a desirable host. For example, various strains of *E. coli* used for expression are well-known as host cells in the field of biotechnology. Various strains of *B. subtilis, Streptomyces*, other bacilli and the like may also be employed in this method.

Where desired, strains of yeast cells known to those skilled in the art are also available as host cells, as well as insect cells, e.g. *Drosophila* and *Lepidoptera* and viral expression systems. See, e.g. Miller et al., Genetic Engineering, 8:277-298, Plenum Press (1986) and references cited therein.

The general methods by which the vectors may be constructed, the transfection methods required to produce the host cells of the invention, and culture methods necessary to produce the antibody of the invention from such host cell are all conventional techniques. Typically, the culture method of the present invention is a serum-free culture method, usually by culturing cells serum-free in suspension. Likewise, once produced, the antibodies of the invention may be purified from the cell culture contents according to standard procedures of the art, including ammonium sulfate precipitation, affinity columns, column chromatography, gel electrophoresis and the like. Such techniques are within the skill of the art and do not limit this invention. For example, preparation of antibodies are described in WO 99/58679 and WO 96/16990.

Yet another method of expression of the antibodies may utilize expression in a transgenic animal, such as described in U.S. Pat. No. 4,873,316. This relates to an expression system using the animal's casein promoter which when transgenically incorporated into a mammal permits the female to produce the desired recombinant protein in its milk.

In a further aspect of the invention there is provided a method of producing an antibody of the invention which method comprises the step of culturing a host cell transformed or transfected with a vector encoding the light and/or heavy chain of the antibody of the invention and recovering the antibody thereby produced.

Suitable host cells for cloning or expressing vectors encoding antibodies of the invention are prokaroytic, yeast or higher eukaryotic cells. Suitable prokaryotic cells include eubacteria e.g. enterobacteriaceae such as *Escherichia* e.g. *E. Coli* (for example ATCC 31,446; 31,537; 27,325), *Enterobacter, Erwinia, Klebsiella Proteus, Salmonella* e.g. *Salmonella typhimurium, Serratia* e.g. *Serratia marcescans* and *Shigella* as well as Bacilli such as *B. subtilis* and *B. lichenifonnis* (see DD 266 710), *Pseudomonas* such as *P. aeruginosa* and *Streptomyces*. Of the yeast host cells, *Saccharomyces cerevisiae, schizosaccharomyces pombe, Kluyveromyces* (e.g. ATCC 16,045; 12,424; 24178; 56,500), *yarrowia* (EP402, 226), *Pichia Pastoris* (EP183, 070, see also Peng et al J. Biotechnol. 108 (2004) 185-192), *Candida, Trichoderma reesia* (EP244, 234), Penicillin, *Tolypocladium* and *Aspergillus* hosts such as *A. nidulans* and *A. niger* are also contemplated.

Although Prokaryotic and yeast host cells are specifically contemplated by the invention, typically however, host cells of the present invention are vertebrate cells. Suitable vertebrate host cells include mammalian cells such as COS-1 (ATCC No. CRL 1650) COS-7 (ATCC CRL 1651), human embryonic kidney line 293, baby hamster kidney cells (BHK) (ATCC CRL. 1632), BHK570 (ATCC NO: CRL 10314), 293 (ATCC NO. CRL 1573), Chinese hamster ovary cells CHO (e.g. CHO-K1, ATCC NO: CCL 61, DHFR-CHO cell line such as DG44 (see Urlaub et al, (1986) Somatic Cell Mol. Genet. 12, 555-556)), particularly those CHO cell lines adapted for suspension culture, mouse sertoli cells, monkey kidney cells, African green monkey kidney cells (ATCC CRL-1587), HELA cells, canine kidney cells (ATCC CCL 34), human lung cells (ATCC CCL 75), Hep G2 and myeloma or lymphoma cells e.g. NS0 (see U.S. Pat. No. 5,807,715), Sp2/0, Y0.

Thus in one embodiment of the invention there is provided a stably transformed host cell comprising a vector encoding a heavy chain and/or light chain of the therapeutic antibody or antigen binding fragment thereof as described herein. Typically such host cells comprise a first vector encoding the light chain and a second vector encoding said heavy chain.

Host cells transformed with vectors encoding the therapeutic antibodies of the invention or antigen binding fragments thereof may be cultured by any method known to those skilled in the art. Host cells may be cultured in spinner flasks, roller bottles or hollow fibre systems but it is preferred for large scale production that stirred tank reactors are used particularly for suspension cultures. Typically the stirred tankers are adapted for aeration using e.g. spargers, baffles or low shear impellers. For bubble columns and airlift reactors direct aeration with air or oxygen bubbles may be used. Where the host cells are cultured in a serum free culture media it is preferred that the media is supplemented with a cell protective agent such as pluronic F-68 to help prevent cell damage as a result of the aeration process. Depending on the host cell characteristics, either microcarriers may be used as growth substrates for anchorage dependent cell lines or the cells may be adapted to suspension culture (which is typical). The culturing of host cells, particularly vertebrate host cells may utilise a variety of operational modes such as fed-batch, repeated batch processing (see Drapeau et al (1994) cytotechnology 15: 103-109), extended batch process or perfusion culture. Although recombinantly transformed mammalian host cells may be cultured in serum-containing media such media comprising fetal calf serum (FCS), it is preferred that such host cells are cultured in synthetic serum-free media such as disclosed in Keen et al (1995) Cytotechnology 17:153-163, or commercially available media such as ProCHO-CDM or UltraCHO™ (Cambrex N.J., USA), supplemented where necessary with an energy source such as glucose and synthetic growth factors such as recombinant insulin. The serum-free culturing of host cells may require that those cells are adapted to grow in serum free conditions. One adaptation approach is to culture such host cells in serum containing media and repeatedly exchange 80% of the culture medium for the serum-free media so that the host cells learn to adapt in serum free conditions (see e.g. Scharfenberg K et al (1995) in *Animal Cell technology: Developments towards the 21st century* (Beuvery E. C. et al eds), pp 619-623, Kluwer Academic publishers).

Antibodies of the invention secreted into the media may be recovered and purified from the media using a variety of techniques to provide a degree of purification suitable for the intended use. For example the use of therapeutic antibodies of the invention for the treatment of human patients typically mandates at least 95% purity, more typically 98% or 99% purity compared to the culture media comprising the therapeutic antibodies. In the first instance, cell debris from the culture media is typically removed using centrifugation followed by a clarification step of the supernatant using e.g. microfiltration, ultrafiltration and/or depth filtration. A variety of other techniques such as dialysis and gel electrophoresis and chromatographic techniques such as hydroxyapatite (HA), affinity chromatography (optionally involving an affinity tagging system such as polyhistidine) and/or hydrophobic interaction chromatography (HIC, see U.S. Pat. No. 5,429, 746) are available. In one embodiment, the antibodies of the invention, following various clarification steps, are captured using Protein A or G affinity chromatography followed by further chromatography steps such as ion exchange and/or HA chromatography, anion or cation exchange, size exclusion chromatography and ammonium sulphate precipitation. Typically, various virus removal steps are also employed (e.g. nanofiltration using e.g. a DV-20 filter). Following these various steps, a purified (typically monoclonal) preparation comprising at least 75 mg/ml or greater e.g. 100 mg/ml or greater of the antibody of the invention or antigen binding fragment thereof is provided and therefore forms an embodiment of the invention. Suitably such preparations are substantially free of aggregated forms of antibodies of the invention.

In accordance with the present invention there is provided a method of producing an anti-NOGO antibody of the present invention which specifically binds to and neutralises the activity of human NOGO-A which method comprises the steps of;
(a) providing a first vector encoding a heavy chain of the antibody;
(b) providing a second vector encoding the light chain of the antibody;
(c) transforming a mammalian host cell (e.g. CHO) with said first and second vectors;
(d) culturing the host cell of step (c) under conditions conducive to the secretion of the antibody from said host cell into said culture media;
(e) recovering the secreted antibody of step (d).

Once expressed by the desired method, the antibody is then examined for in vitro activity by use of an appropriate assay. Presently conventional ELISA assay formats are employed to assess qualitative and quantitative binding of the antibody to NOGO. Additionally, other in vitro assays may also be used to verify neutralizing efficacy prior to subsequent human clinical studies performed to evaluate the persistence of the antibody in the body despite the usual clearance mechanisms.

Other modifications to the antibodies of the present invention include glycosylation variants of the antibodies of the invention. Glycosylation of antibodies at conserved positions in their constant regions is known to have a profound effect on antibody function, particularly effector functioning such as those described above, see for example, Boyd et al (1996), Mol. Immunol. 32, 1311-1318. Glycosylation variants of the therapeutic antibodies or antigen binding fragments thereof of the present invention wherein one or more carbonhydrate moiety is added, substituted, deleted or modified are contemplated. Introduction of an asparagine-X-serine or asparagine-X-threonine motif creates a potential site for enzymatic attachment of carbonhydrate moieties and may therefore be used to manipulate the glycosylation of an antibody. In Raju et al (2001) Biochemistry 40, 8868-8876 the terminal sialyation of a TNFR-IgG immunoadhesin was increased through a process of regalactosylation and/or resialylation using beta-1,4-galactosyltransferace and/or alpha, 2,3 sialyltransferase. Increasing the terminal sialylation is believed to increase the half-life of the immunoglobulin. Antibodies, in common with most glycoproteins, are typically produced in nature as a mixture of glycoforms. This mixture is particularly apparent when antibodies are produced in eukaryotic, particularly mammalian cells. A variety of methods have been developed to manufacture defined glycoforms, see Zhang et al Science (2004), 303, 371, Sears et al, Science, (2001) 291, 2344, Wacker et al (2002) Science, 298 1790, Davis et al (2002) Chem. Rev. 102, 579, Hang et al (2001) Acc. Chem. Res 34, 727. Thus the invention concerns a plurality of therapeutic (typically monoclonal) antibodies (which may be of the IgG isotype, e.g. IgG1) as described herein comprising a defined number (e.g. 7 or less, for example 5 or less such as two or a single) glycoform(s) of said antibodies or antigen binding fragments thereof.

The therapeutic agents of this invention may be administered as a prophylactic or following the stroke event/on-set of clinical symptoms, or as otherwise needed. The dose and duration of treatment relates to the relative duration of the molecules of the present invention in the human circulation, and can be adjusted by one of skill in the art depending upon the condition being treated and the general health of the patient. It is envisaged that repeated dosing (e.g. once a week or once every two weeks) over an extended time period (e.g. four to six months) may be required to achieve maximal therapeutic efficacy.

The mode of administration of the therapeutic agent of the invention may be any suitable route which delivers the agent to the host. The antibodies, and pharmaceutical compositions of the invention are particularly useful for parenteral administration, i.e., subcutaneously (s.c.), intrathecally, intraperitoneally (i.p.), intramuscularly (i.m.), intravenously (i.v.), or intranasally (i.n.).

Therapeutic agents of the invention may be prepared as pharmaceutical compositions containing an effective amount of the antibody of the invention as an active ingredient in a pharmaceutically acceptable carrier. In the prophylactic agent of the invention, an aqueous suspension or solution containing the engineered antibody, preferably buffered at physiological pH, in a form ready for injection is preferred. The compositions for parenteral administration will commonly comprise a solution of the antibody of the invention or a cocktail thereof dissolved in a pharmaceutically acceptable carrier, preferably an aqueous carrier. A variety of aqueous carriers may be employed, e.g., 0.9% saline, 0.3% glycine, and the like. These solutions are sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc. The concentration of the antibody of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and between about 1 ng to about 100 mg, e.g. about 50 ng to about 30 mg or more preferably, about 5 mg to about 25 mg, of an antibody of the invention. Similarly, a pharmaceutical composition of the invention for intravenous infusion could be made up to contain about 250 ml of sterile Ringer's solution, and about 1 to about 30 and preferably 5 mg to about 25 mg of an engineered antibody of the invention per ml of Ringer's solution. Actual methods for preparing parenterally administrable compositions are well known or will be apparent to those skilled in the art and are described in more detail in, for example, Remington's Pharmaceutical Science, 15th ed., Mack Publishing Company, Easton, Pa. For the preparation of intravenously administrable antibody formulations of the invention see Lasmar U and Parkins D "The formulation of Biopharmaceutical products", Pharma. Sci. Tech. today, page 129-137, Vol. 3 (3 Apr. 2000), Wang, W "Instability, stabilisation and formulation of liquid protein pharmaceuticals", Int. J. Pharm 185 (1999) 129-188, Stability of Protein Pharmaceuticals Part A and B ed Ahern T. J., Manning M. C., New York, N.Y.: Plenum Press (1992), Akers, M. J. "Excipient-Drug interactions in Parenteral Formulations", J. Pharm Sci 91 (2002) 2283-2300, Imamura, K et al "Effects of types of sugar on stabilization of Protein in the dried state", J Pharm Sci 92 (2003) 266-274, Izutsu, Kkojima, S. "Excipient crystallinity and its protein-structure-stabilizing effect during freeze-drying", J. Pharm. Pharmacol, 54 (2002) 1033-1039, Johnson, R, "Mannitol-sucrose mixtures-versatile formulations for protein lyophilization", J. Pharm. Sci, 91 (2002) 914-922.

Ha, E Wang W, Wang Y. j. "Peroxide formation in polysorbate 80 and protein stability", J. Pharm Sci, 91, 2252-2264, (2002) the entire contents of which are incorporated herein by reference and to which the reader is specifically referred.

It is preferred that the therapeutic agent of the invention, when in a pharmaceutical preparation, be present in unit dose forms. The appropriate therapeutically effective dose will be determined readily by those of skill in the art. To effectively treat stroke and other neurological diseases in a human, one dose within the range of 700 to 3500 mg per 70 kg body weight of an antibody of this invention is envisaged to be administered parenterally, preferably s.c., i.v. or i.m. (intramuscularly). Such dose may, if necessary, be repeated at appropriate time intervals selected as appropriate by a physician.

The antibodies described herein can be lyophilized for storage and reconstituted in a suitable carrier prior to use. This technique has been shown to be effective with conventional immunoglobulins and art-known lyophilization and reconstitution techniques can be employed.

In another aspect, the invention provides a pharmaceutical composition comprising anti-NOGO antibody of the present invention or a functional fragment thereof and a pharmaceutically acceptable carrier for treatment or prophylaxis of stroke and other neurological diseases.

In a yet further aspect, the invention provides a pharmaceutical composition comprising the anti-NOGO antibody of the present invention or a functional fragment thereof and a pharmaceutically acceptable carrier for inhibiting neurodegeneration and/or promoting functional recovery in a human patient suffering, or at risk of developing, a stroke or other neurological disease.

The invention further provides a method of treatment or prophylaxis of stroke (particularly ischemic stroke) and other neurological diseases/disorders, in particular Alzheimer's disease, in a human which comprises administering to said human in need thereof an effective amount of an anti-NOGO antibody of the present invention or a functional fragment thereof. Antibodies of the invention may be used in methods of treatment to slow or halt the progression and/or onset of Alzheimer's disease in addition to (or as an alternative to) treating established disease in a human patient.

Further the invention provides the use of an anti-NOGO antibody of the present invention, or a functional fragment thereof, in the preparation of a medicament for treatment or prophylaxis of stroke and other neurological diseases/disorders, in particular Alzheimer's disease.

The invention also provides a method of inhibiting neurodegeneration and/or promoting functional recovery in a human patient suffering, or at risk of developing, a stroke or other neurological disease/disorder, in particular Alzheimer's disease, which comprises administering to said human in need thereof an effective amount of an anti-NOGO antibody of the present invention or a functional fragment thereof.

In addition the invention provides the use of an anti-NOGO antibody of the present invention or a functional fragment thereof in the preparation of a medicament for inhibiting neurodegeneration and/or promoting functional recovery in a human patient afflicted with, or at risk of developing, a stroke and other neurological disease/disorder, in particular Alzheimer's disease.

The invention further provides a method of treating or prophylaxis of stroke or other neurological disease/disorder, in particular Alzheimer's disease, in a human comprising the step of parenteral administration of a therapeutically effective amount of an anti-NOGO antibody of the present invention. Preferably the said anti-NOGO antibody is administered intravenously.

Neurological diseases or disorders as used hereinabove includes, but is not limited to traumatic brain injury, spinal cord injury, fronto-temporal dementias (tauopathies), peripheral neuropathy, Parkinson's disease, Huntington's disease, and in particular Alzheimer's disease, multiple sclerosis or amyotrophic lateral sclerosis (ALS).

The invention also provides a method of promoting axonal sprouting comprising the step of contacting a human axon with an anti-NOGO antibody of the present invention. This method may be performed in-vitro or in-vivo, preferably the method is performed in-vivo.

In a further aspect therefore there is provided a method of treating stroke (particularly ischemic stroke), brain injury, spinal cord injury, fronto-temporal dementias (tauopathies), peripheral neuropathy, Parkinson's disease, Huntington's disease, multiple sclerosis and in particular Alzheimer's disease in a human patient which method comprises the intravenous administration of a therapeutically effective amount of an anti-NOGO antibody of the invention.

In a further aspect of the present invention there is provided a method of promoting axon sprouting of neurons within the central nervous system of a human subject (e.g. patient) which method comprises administering (e.g. intravenously administering) a therapeutically effective amount of an anti-NOGO antibody of the present invention.

In a further aspect of the present invention there is provided the use of an anti-NOGO antibody of the present invention (e.g. an anti-NOGO antibody comprising the CDRs set forth herein) in the manufacture of an intravenously administrable medicament for the treatment of stroke (particularly ischemic stroke), brain injury, spinal cord injury, fronto-temporal dementias (tauopathies), peripheral neuropathy, Parkinson's disease, Huntington's disease, and in particular Alzheimer's disease, multiple sclerosis or amyotrophic lateral sclerosis (ALS) in a human patient.

In a further aspect of the invention there is provided a method of regenerating axon processes in neurons of the central nervous system in a human patient afflicted with (or susceptible to) stroke (particularly ischemic stroke), brain injury, spinal cord injury, fronto-temporal dementia (tauopathies), peripheral neuropathy, Parkinson's disease, Huntington's disease, multiple sclerosis and in particular Alzheimer's disease which method comprises the step of administering (e.g. intravenously) a therapeutically effective amount of an anti-NOGO antibody of the present invention.

In a further aspect of the invention there is provided the use of an anti-NOGO antibody of the present invention in the manufacture of an intravenously administrable pharmaceutical composition for regenerating axon processes in neurons of the central nervous system in a human patient afflicted with (or susceptible to) stroke (particularly ischemic stroke), brain injury, spinal cord injury, fronto-temporal dementias (tauopathies), peripheral neuropathy, Parkinson's disease, Huntington's disease, multiple sclerosis and in particular Alzheimer's disease.

In a further aspect of the invention there is provided a method of modulating the production of an amyloidogenic peptide comprising contacting a cell which is expressing the precursor from which the amyloidogenic peptide is derived and a NOGO polypeptide (e.g. human NOGO-A) with an anti-NOGO antibody of the present invention. In typical embodiments, the precursor is APP. In further typical embodiments the amyloidogenic peptide is A$\beta$, most preferably A$\beta$40, A$\beta$42 or a combination of both.

As used herein, the term "functional recovery" refers to a motor and/or sensory and/or behavioural improvement in a subject following e.g. an ischemic event or injury or on-set of clinical symptoms. Functional recovery in humans may be evaluated by instruments designed to measure elemental neurological functions such as motor strength, sensation and coordination, cognitive functions such as memory, language and the ability to follow directions, and functional capacities such as basic activities of daily living or instrumental activities. Recovery of elemental neurological function can be measured with instruments such as the NIH Stroke Scale (NIHSS), recovery of cognitive function can be measured with neuropsychological tests such as Boston Naming Test, Trail-making Tests, and California Verbal Learning Test, and activities of daily living may be measured with instruments such as the ADCS/ADL (Alzheimer's Disease Clinical Studies/Activities of Daily Living) scale or the Bristol Activities of Daily Living Scale, all tests and scales known in the art.

The following examples illustrate but do not limit the invention.

EXAMPLE 1

Construction and Expression of Humanised Anti-NOGO Antibodies

Humanised $V_H$ and $V_L$ constructs were prepared de novo by build up of overlapping oligonucleotides including restriction sites for cloning into Rld and Rln mammalian expression vectors (or any other suitable expression vector for expression of proteins in mammalian cells) as well as a human signal sequence. Hind III and Spe I restriction sites were introduced to frame the $V_H$ domain containing the CAMPATH-1H signal sequence for cloning into Rld containing the human γ1 mutated constant region to prevent ADCC and CDC activity (L235A and G237A-EU Index numbering system). Hind III and BsiWI restriction sites were introduced to frame the $V_L$ domain containing the CAMPATH-1H signal sequence for cloning into Rln containing the human kappa constant region. CAMPATH-1H Signal Sequence: MGWSCIILFLVATATGVHS (SEQ.ID.NO:31)

Plasmids encoding human IgG heavy chain amino acid sequences, wherein the CDR were that described in table 2, were produced. Plasmids encoding human IgG heavy chain amino acid sequences, wherein the CDRs were that described in table 3, were produced from those existing earlier plasmids by introducing single point mutations, G95M (Kabat numbering), using the Quickchange kit (Stratagene).

The following table discloses which full length heavy chain protein sequences were made in the plasmid vectors and which of the sequences were paired, in the sense that the only difference in the amino acid sequences of the paired full length (FL) heavy chain sequences was a substitution at G95M (kabat numbering) within the CDR H3 of the variable region:

TABLE 8

| CDRs as defined in Table 2 | G95M substitution (to form CDR H3 of Table 3) |
|---|---|
| H1 FL (SEQ ID NO. 35) | Not done |
| H6 FL (SEQ ID NO. 15) | H26 FL (SEQ ID NO. 53) |
| H16 FL (SEQ ID NO. 16) | H27 FL (SEQ ID NO. 54) |
| H20 FL (SEQ ID NO. 42) | H28 FL (SEQ ID NO. 55) |

Plasmids encoding the heavy chains were then co-transfected into CHO cells (for details see example 2) with the one of the following full length light chain sequences: L11 FL (SEQ ID NO. 36), L13 FL (SEQ ID NO. 17), or L16 FL (SEQ ID NO. 18).

In parallel a chimera termed HcLc (which is the chimera of 2A10 (SEQ ID NO. 9 and 10—the full length chains comprising the 2A10 murine VH (SEQ ID NO. 7) and VL (SEQ ID NO.8) and human IgG constant regions)) was produced.

EXAMPLE 2

Antibody Expression in CHO Cells

Rld and Rln plasmids (or other vectors suitable for use in mammalian cells) encoding the heavy and light chains respectively were transiently co-transfected into CHO cells and expressed at small scale or large scale to produce antibody. Alternatively the same plasmids were co-transfected into DHFR-CHO cells by electroporation and a stable polyclonal population of cells expressing the appropriate antibody were selected using a nucleoside-free media (Rld contains the DHFR gene, Rln contains a neomycin selection marker). In some assays, antibodies were assessed directly from the tissue culture supernatant. In other assays, recombinant antibody was recovered and purified by affinity chromatography on Protein A sepharose.

EXAMPLE 3

Humanised Anti-NOGO Antibody Binds to NOGO

GST-human NOGO-A56 (see example 5) at 0.05-1 µg/ml in PBS was coated onto Nunc Immunosorp plates (100 µl per well) at 4° C. overnight. Wells were rinsed once with TBS+ 0.05% Tween (TBST) then incubated with 2% BSA in TBST to block non-specific binding sites at room temperature for 1 hour. Antibodies were diluted in TBST+2% BSA to 10 µg/ml and 1/2 dilutions made from this. Antibodies were added to wells in duplicate and incubated at room temperature for 1 hour. Wells were washed three times with TBST then incubated with anti-human kappa peroxidase conjugate (1:2000) for 1 hour. The wells were washed three times with TBST and then incubated with 100 µl OPD peroxidase substrate (Sigma) per well for 10 minutes. The colour reaction was stopped by the addition of 25 µl concentrated $H_2SO_4$. Optical density at 490 nm was measured using a plate reader. Background values read from wells with no antibody were subtracted.

FIGS. 1-4 illustrate the dose-dependent binding of humanised antibodies in comparison with the chimera (termed HcLc which is the chimera of 2A10 (comprising the 2A10 murine VH (SEQ ID NO. 7) and VL (SEQ ID NO.8) and human IgG constant regions)) to GST-human NOGO-A56 (see Example 5 for details) in an ELISA assay. The Y-axis shows the measured optical density (OD) at 490 nm, a quantitative measure of antibody captured in the wells. The X-axis shows the concentration of antibody used (mcg/ml) per well at each data point.

The antibody material used in FIGS. 1-4 is purified antibody generated by either the polyclonal expression system or large scale transient transfections. In these cases, IgG levels were quantified by ELISA and optical density.

The results from the experiments shown in FIGS. 1-4 shows that the inclusion of the G95M mutation improves the performance of the antibody. The only exception is H27L16 shown in FIGS. 3 and 4 which performed very poorly. We believe that this data resulted from an unidentified technical problem with the H27L16 assay, since H27L16 has otherwise consistently performed well in other assays (in ELISA shown in FIGS. 1 and 2, and in BIAcore assays (Tables 9 and 10)). H27L16 has also been shown to work very well in later experiments (see FIGS. 11 and 12).

EXAMPLE 4

Antibody Quantification Protocol

Nunc Immunosorp plates were coated with a goat anti-human IgG chain capture antibody (Sigma #13382) at 2 µg/ml in Bicarbonate buffer (Sigma #C3041) and incubated overnight at 4° C. The plates were washed twice with TBS containing 0.05% Tween20 (TBST) and blocked with 200 µl TBST containing 2% (or from 1-3%) BSA (block buffer) for 1 hr at room temperature. The plates were washed twice with TBST. Tissue culture supernatants containing antibody were titrated across the plate in 2-fold dilution steps into block buffer and incubated at room temperature for 1 hr. The plates were washed three times with TBST. HRP conjugated antibody H23 (goat anti-human kappa chain, Sigma #A7164) was diluted 1:2000 in TBST and 100 µl added to each well. The plates were incubated at room temperature for 1 hr. The plates were washed three times with TBST and developed with 100 µl of Fast-OPD substrate (Sigma #P9187). Colour was allowed to develop for 5-10 mins after which time the ELISA was stopped with 25 µl 3M $H_2SO_4$. The absorbance at 490 nM was read plate and antibody concentration determined by reference to a standard curve.

EXAMPLE 5

Production of NOGO-A Fragment (NOGO-A56, SEQ.ID.NO:32)

A cDNA sequence encoding a polypeptide comprising amino acids 586-785 and a GST tag (SEQ.I.D.NO:32) of human NOGO-A was created by cloning a cDNA encoding amino acids 586-785 of human NOGO-A into the BamHI-XhoI sites of pGEX-6P1 to generate a GST-tagged fusion protein designated GST-human-NOGO-A56. Plasmid was expressed in BL21 cells in 2×TY medium with 100 µg/ml ampicillin following induction with IPTG to 0.5 mM at 37C for 3 hours. Cell pellets were lysed by sonication and the fusion protein purified using Glutathione-sepharose (Amersham Pharmacia) following manufacturers instructions. Purified protein was eluted using reduced glutathione and extensively dialysed against PBS, quantitated using BSA standards and a BioRad coomassie based protein assay and then stored in aliquots at –80C.

EXAMPLE 6

BiaCore Analysis of Humanised Anti NOGO Monoclonal Antibodies

The binding kinetics of the anti-NOGO monoclonal antibody (mAb) to recombinantly expressed GST-human NOGO-A was analysed using the Biacore3000 biosensor or BIAcore T100. The hNOGO-A chip was prepared as follows:
Method
GST-human NOGO-A56 was immobilised to a CM5 chip by primary amine coupling using the Biacore Wizard program designed for targeted immobilisation levels. The CM5 sensor surface was activated by passing a solution of 50 mM N-hydroxy-succinimide (NHS) and 200 mM N-ethyl-N'-dimethylaminopropyl carbonide (EDC). Then GST-human NOGO-A56 in sodium acetate buffer, pH5.0 or pH 4.5, was passed over the chip and immobilised. After immobilisation was complete any still activated esters were blocked by an injection of 1M ethanolamine hydrochloride, pH8.5.

The anti-NOGO mAbs were diluted down in HBS-EP (10 mM HEPES, pH 7.4, 150 mM NaCl, 3 mM EDTA, and 0.005% P-20 surfactant) for the BIAcore 3000 or HBS-EP+ (10 mM HEPES, pH 7.4, 150 mM NaCl, 3 mM EDTA, and 0.05% P-20 surfactant) in the case of the T100 and binding studies were carried out at range of defined antibody concentrations. All runs were referenced against a blanked sensor surface (one that had been activated and blocked as described earlier but had no addition of ligand). Analysis of binding was carried out using the BIAevaluation kinetic analysis software version 4.1 for the BIAcore 3000 and T100 kinetic analysis software version 1.0. Biacore analysis of other antibodies of the invention essentially followed the same protocol as described herein. Unless otherwise stated, the BIAcore experiments were performed at 25° C.

In the following Results section each data table represents the results obtained from an individual experiment.

TABLE 9

| Results | | | |
|---|---|---|---|
| Antibody | ka (1/Ms) | kd (1/s) | KD (pM) |
| HcLc | 3.19E6 | 2.49E-3 | 779 |
| H27L13 | 6.2E6 | 1.8E-3 | 291 |
| H26L13 | 3.23E6 | 3.11E-3 | 963 |
| H28L13 | 7.26E6 | 3.3E-3 | 454 |
| H27L16 | 6.24E6 | 1.21E-3 | 194 |
| H28L16 | 7.25E6 | 2.14E-3 | 296 |

TABLE 10

| Results | | | |
|---|---|---|---|
| Antibody | ka (1/Ms) | kd (1/s) | KD (nM) |
| HcLc (25° C.) | 2.66E6 | 3.13E-3 | 1.18 |
| HcLc (37° C.) | 5.08E6 | 7.74E-3 | 1.46 |
| H16L16 (25° C.) | 3.43E6 | 3.72E-3 | 1.08 |
| H16L16 (37° C.) | 5.31E6 | 6.16E-3 | 1.16 |
| H20L16 (25° C.) | 4.69E6 | 5.42E-3 | 1.16 |
| H20L16 (37° C.) | 7.17E6 | 1.08E-3 | 1.51 |
| H27L16 (25° C.) | 3.94E6 | 1.50E-3 | 0.380 |
| H27L16 (37° C.) | 7.18E6 | 3.06E-3 | 0.426 |
| H27L13 (25° C.) | 3.50E6 | 2.13E-3 | 0.606 |
| H27L13 (37° C.) | 6.58E6 | 4.22E-3 | 0.641 |
| H28L16 (25° C.) | 4.33E6 | 2.64E-3 | 0.610 |
| H28L16 (37° C.) | 7.73E6 | 5.24E-3 | 0.678 |
| H28L13 (25° C.) | 4.16E6 | 3.89E-3 | 0.936 |
| H28L13 (37° C.) | 7.43E6 | 7.59E-3 | 1.02 |

TABLE 11

| Results | | | |
|---|---|---|---|
| Antibodies | ka (1/Ms) | Kd (1/s) | KD (nM) |
| HcLc | 3.17E6 | 2.33E-3 | 0.74 |
| H26L13 | 3.45E6 | 2.88E-3 | 0.87 |
| H27L13 | 6.58E6 | 1.83E-3 | 0.28 |
| H28L13 | 6.97E6 | 3.17E-3 | 0.45 |
| H28L16 | 6.89E6 | 1.95E-3 | 0.28 |

EXAMPLE 7

BiaCore Analysis of Humanised Anti NOGO Monoclonal Antibodies Using Off-Rate Ranking The GST-human NOGO-A56 chip was prepared as for kinetic analysis. Cell supernatants where taken directly from transient transfections of CHO-K1 cells. These were passed directly over the sensor surface and the interaction measured. A mock transfected cell supernatant was used for double referencing to remove any artefacts due to the tissue culture media. All runs were referenced against a blanked sensor surface (one that had been activated and blocked as described earlier but had no addition of ligand). Analysis of binding was carried out using the BIAevaluation kinetic analysis software version 4.1.

EXAMPLE 8

Peptide Mapping 47 overlapping peptides spanning the NOGO-A56 portion of GST-human NOGO-A56 domain (SEQ ID NO. 32) were obtained (from Mimotope™). The peptides are 16 amino acids in length with a twelve amino acid overlap with the adjacent peptide (each peptide further comprising a biotin-SGSG sequence at the N-terminus) with the exception of the first peptide which has a GSG-biocytin tag at the C-terminus. The peptides were used to epitope map the binding site of 2A10 and H28L16.
Method for Epitope Mapping:

Streptavidin at 5 µg/ml in sterile water was coated onto Nunc immunosorp plates (100 µl per well) at 37° C. overnight. The plates were rinsed 3 times with PBS containing 0.05% Tween (PBST) then blocked with 3% BSA in PBST at 4° C. overnight. The plates were washed 3 times with PBST. Peptides were then added to the wells at a concentration of approximately 10 µg/ml (diluted in 3% BSA in PBST) and incubated at room temperature for 1 hour. The plates were washed 3 times with PBST then incubated for 1 hour with anti-NOGO antibodies diluted to 5 µg/ml in 3% BSA in PBST. The plates were washed 3 times with PBST then incubated with anti-human or anti-mouse kappa peroxidase conjugate (1:1000, diluted in 3% BSA in PBST) for 1 hour. The plates were washed 3 times with PBST and then incubated with 100 µl OPD peroxidase substrate (Sigma) per well for 10 minutes. The colour reaction was stopped by the addition of 50 µl 3 molar $H_2SO_4$. Absorbance at 490 nm was measured using a plate reader.

Figure 5:
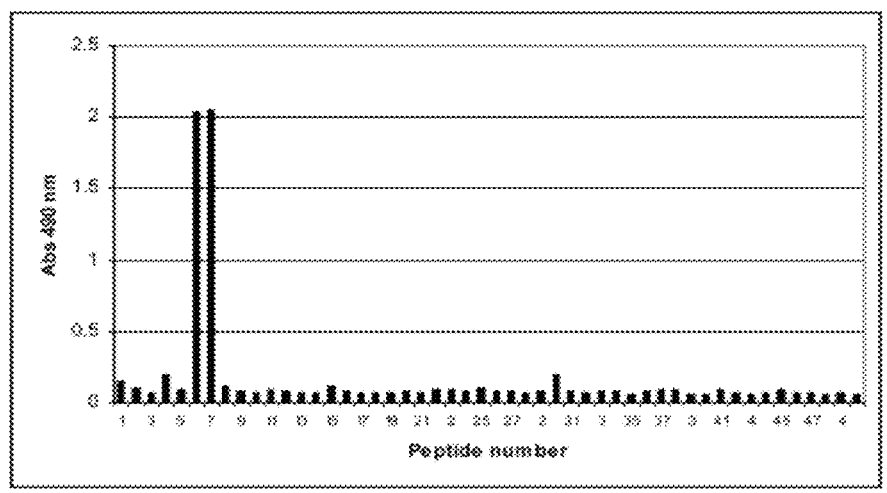
FIG. 5: Epitope mapping using 2A10.
Figure 6:
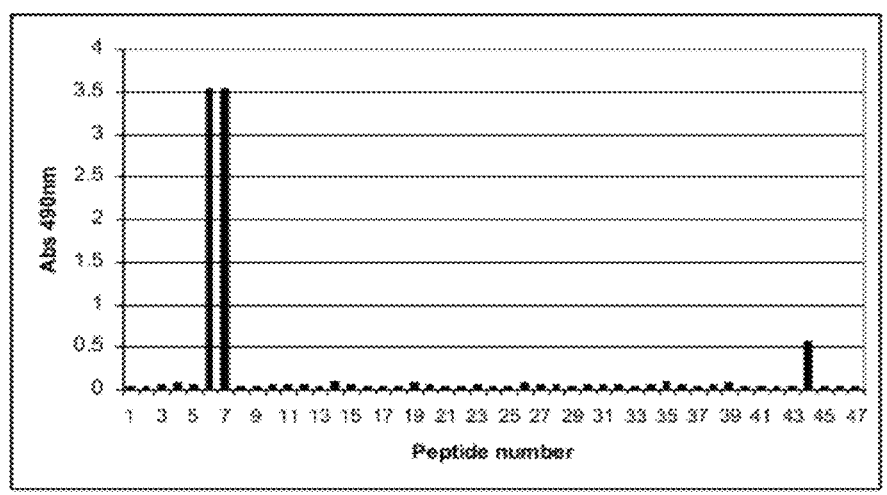
FIG. 6: epitope mapping using H28L16

The results are shown in FIG. 5 (epitope mapping using H28L16), FIG. 6 (epitope mapping using 2A10). FIGS. 5 and 6 show the results of the epitope mapping of 2A10 and H28L16, respectively. The data shown indicates that 2A10 and H28L16 bind to peptides 6 and 7 of which the NOGO specific portion is given in SEQ ID NO. 73 and SEQ ID NO. 74 respectively, both of which contain the sequence VLPDIVMEAPLN. (SEQ ID NO. 60). These results indicate that VLPDIVMEAPLN (SEQ ID NO.60) contains the binding epitope of 2A10 and H28L16.

EXAMPLE 9

Comparison of HcLc and HcLc Containing the G95M Mutation of the CDR H3

A modified variant of HcLc was constructed from existing expression plasmids by introducing a single point mutation, G95M (Kabat numbering), using the Quikchange kit (Stratagene). The protein sequence of the variable heavy domain Hc(G95M) protein is given in SEQ ID 59.

Figure 7:
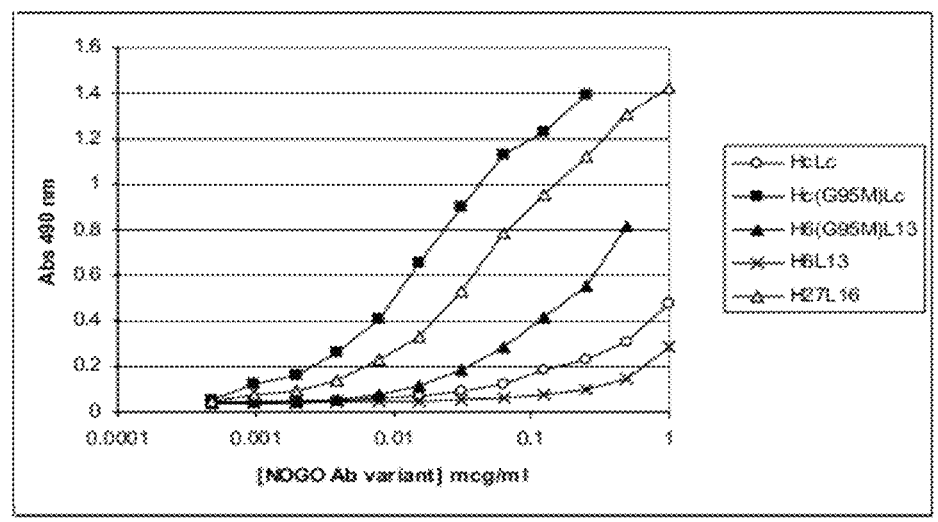
FIG. 7: Comparison of the binding activity of Hc(G95M) Lc and HcLc as determined using a human NOGO-A binding ELISA when NOGO was coated onto Nunc immunosorp plates at 0.05 µg/ml.
Figure 8:
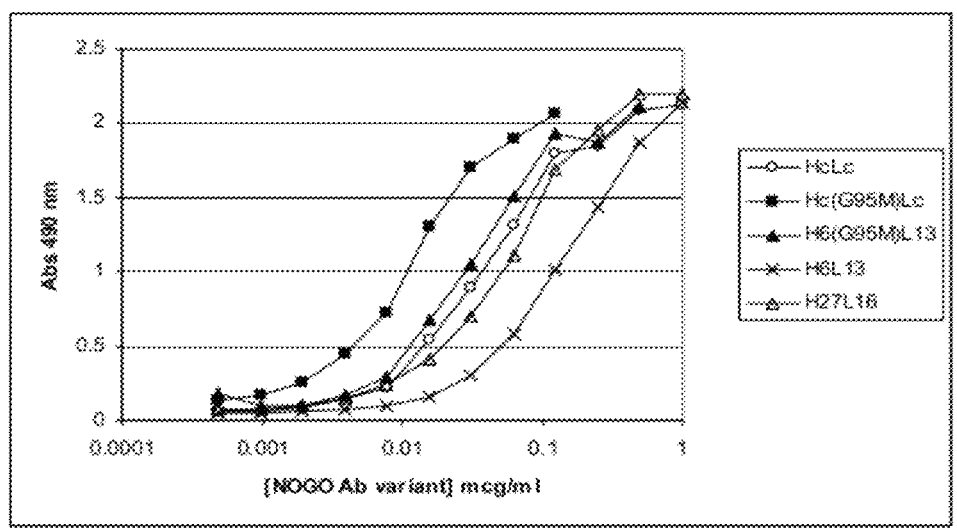
FIG. 8: Comparison of the binding activity of Hc(G95M) Lc and HcLc as determined using a human NOGO-A binding ELISA when NOGO was coated onto Nunc immunosorp plates at 1 µg/ml.

Hc(G95M)Lc was expressed in CHO cells as described previously. The antibody was quantified as described in Example 4. FIG. 7 and FIG. 8 show a comparison of the binding activity of Hc(G95M)Lc and HcLc as determined using a human NOGO-A binding ELISA when NOGO was coated onto Nunc immunosorp plates at 0.05 (FIG. 7) and 1 µg/ml (FIG. 8). Table below shows a comparison of the binding affinities of Hc(G95M)Lc and HcLc.

TABLE 12

| | Off-rate measured by Biacore ranking based on one experiment | |
|---|---|---|
| Antibody | Sequence ID of heavy chain variable region | Off-rate kd (1/s) |
| H6L13 | 11 | 1.38E−2 |
| H6(G95M)L13 | 47 | 4.31E−3 |
| HcLc | 7 | 2.66E−3 |
| Hc(G95M)Lc | 59 | 6.14E−4 |

The data demonstrates that the G95M substitution within CDR H3 not only increases the binding activity of the humanised antibodies (H6L13), but also the murine donor antibody 2A10 (HcLc).

EXAMPLE 10

Construction and Testing of NOGO Antibodies Containing Substitutions in CDR H3

A panel of 90 heavy chain variable regions was created by single point mutations in the residues contained in the CDR H3, or the preceding Leucine. Specifically, vectors encoding a heavy chain (based on H6FL, SEQ ID NO. 15) were made encoding heavy chain variable regions where each amino acid residue in CDR H3 and the preceding Leucine was substituted (using the Quikchange kit (Stratagene)) with all other naturally occurring amino acids, excluding cysteine, and expressed in conjunction with a light chain (L13FL, SEQ ID NO. 17) to give 90 different antibodies. These antibodies were assayed for binding to NOGO in ELISA and Biacore experiments.

Figure 9:
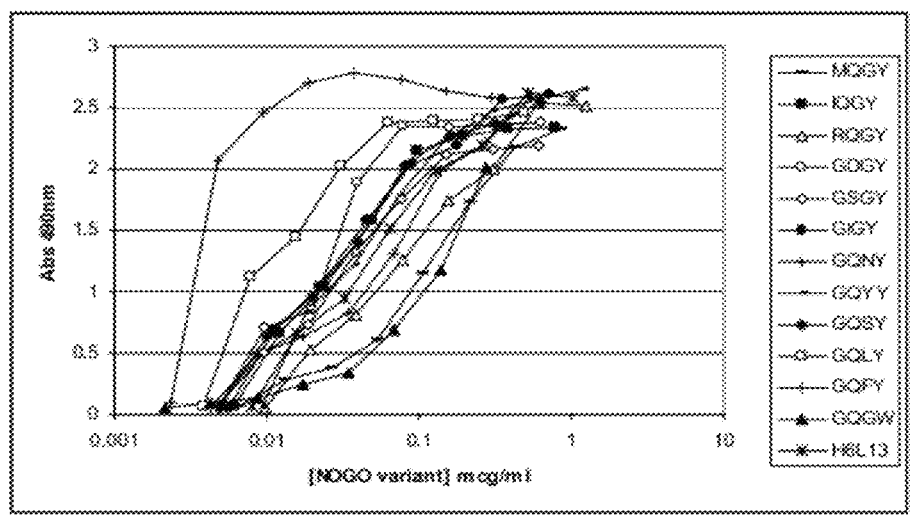
FIG. 9: Comparison of the binding activity of variants of H6FL in comparison to H6FL L13FL.
Figure 10:
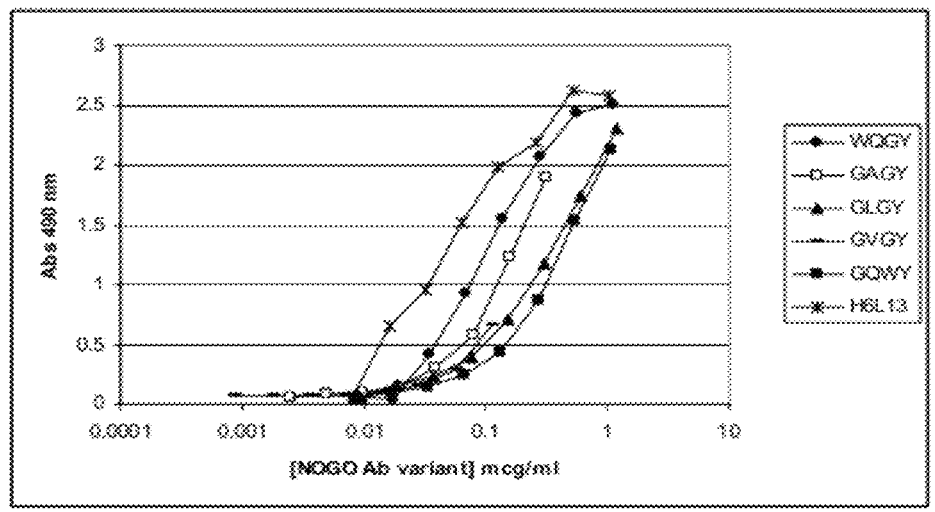
FIG. 10: Comparison of the binding activity of variants of H6FL in comparison to H6FL L13FL.

FIGS. 9 and 10 show a comparison of the binding activity of the variants of H6FL in comparison to $H_6$FL L13FL. Tables 14 and 15 show a comparison of the off-rate kinetics as measured by Biacore—only the results for those antibodies that had a measurable off rate in the Biacore assay and had comparable binding activity to H6L13 in ELISA are shown.

TABLE 14

| Parent Antibody | VH CDR3 | kd (1/s) |
|---|---|---|
| H6L13 | MQGY (SEQ ID NO: 45) | 4.85E−03 |
| HcLc | GQGY (SEQ ID NO: 1) | 5.58E−03 |
| H6L13 | GQNY (SEQ ID NO: 80) | 9.66E−03 |
| H6L13 | GQLY (SEQ ID NO: 82) | 1.32E−02 |
| H6L13 | IQGY (SEQ ID NO: 76) | 1.72E−02 |
| H6L13 | RQGY (SEQ ID NO: 75) | 1.75E−02 |
| H6L13 | GQSY (SEQ ID NO: 62) | 1.86E−02 |
| H6L13 | GQGY (SEQ ID NO: 1) | 1.98E−02 |
| H6L13 | GSGY (SEQ ID NO: 79) | 2.07E−02 |
| H6L13 | GDGY (SEQ ID NO: 77) | 2.12E−02 |
| H6L13 | GQGW (SEQ ID NO: 84) | 2.16E−02 |
| H6L13 | GIGY (SEQ ID NO: 78) | 2.57E−02 |
| H6L13 | GQYY (SEQ ID NO: 81) | 3.28E−02 |
| H6L13 | GQFY (SEQ ID NO: 83) | 3.35E−02 |
| H6L13 | WQGY (SEQ ID NO: 86) | 1.98E−02 |
| H6L13 | GAGY (SEQ ID NO: 87) | 3.15E−02 |
| H6L13 | GLGY (SEQ ID NO: 88) | 1.90E−02 |
| H6L13 | GVGY (SEQ ID NO: 89) | 1.78E−02 |
| H6L13 | GQWY (SEQ ID NO: 90) | 1.77E−02 |

Conclusions The results indicate that the antibodies which retain the binding properties of the murine 2A10, and the GQGY containing antibody H6L13, are those containing following CDR H3: RQGY (SEQ ID NO:75), IQGY (SEQ ID NO:76), MQGY (SEQ ID NO:45), GDGY (SEQ ID NO:77), GIGY (SEQ ID NO:78), GSGY (SEQ ID NO:79), GQNY (SEQ ID NO:80), GQYY (SEQ ID NO:81), GQSY (SEQ ID NO:62), GQLY (SEQ ID NO:82), GQFY (SEQ ID NO:83), GQGW (SEQ ID NO:84), WQGY (SEQ ID NO:86), GAGY (SEQ ID NO:87), GLGY (SEQ ID NO:88), GVGY (SEQ ID NO:89), GQWY (SEQ ID NO:90).

EXAMPLE 11

Comparison of GQGY Containing mab (H20L16) with G95M Variant mabs (H27L16 and H28L13 and H28L16)

The antibodies listed in Table 15 were manufactured as described above.

TABLE 15 humanised 2A10 anti-Nogo-A antibodies giving the total number of back-mutations for the whole antibody (2x heavy chain + 2x light chain).

| Antibody | Total number of back-mutations per whole antibody/tetramer |
|---|---|
| H20L16 | 22 |
| H28L16 | 22 |
| H28L13 | 16 |
| H27L16 | 32 |

In vitro Binding Characteristics

In an attempt to rank the antibodies, their binding properties were investigated in a range of assays including ELISA, reverse format ELISA, competition ELISA, Biacore and by flow cytometry.

11.1 Binding to Recombinant Human NOGO-A in ELISA

Figure 11A:
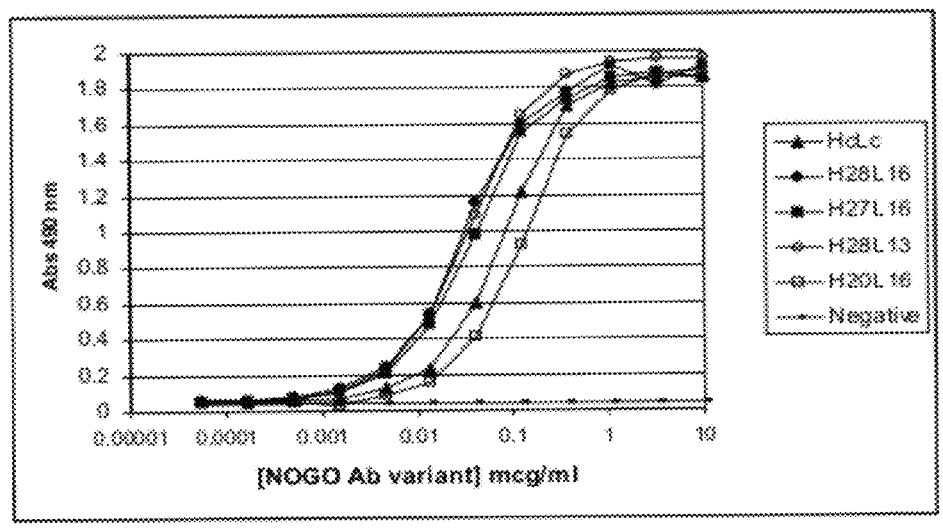
FIG. 11: Direct binding ELISA of the pre-candidate pool antibodies to recombinant human Nogo-A (GST-Nogo-A 5+6). Recombinant GST-Nogo-A 5+6 was coated to the plates at A) 1.0mcg/ml and B) 0.05 mcg/ml. Binding of the antibodies was detected using an anti-human IgG-HRP conjugate (Sigma, #A7340X). The negative control was an anti β-amyloid antibody (H2L1). EC50 values were derived using Robosage. Each of the graphs below show a representative figure from three independent assays.
Figure 11B:
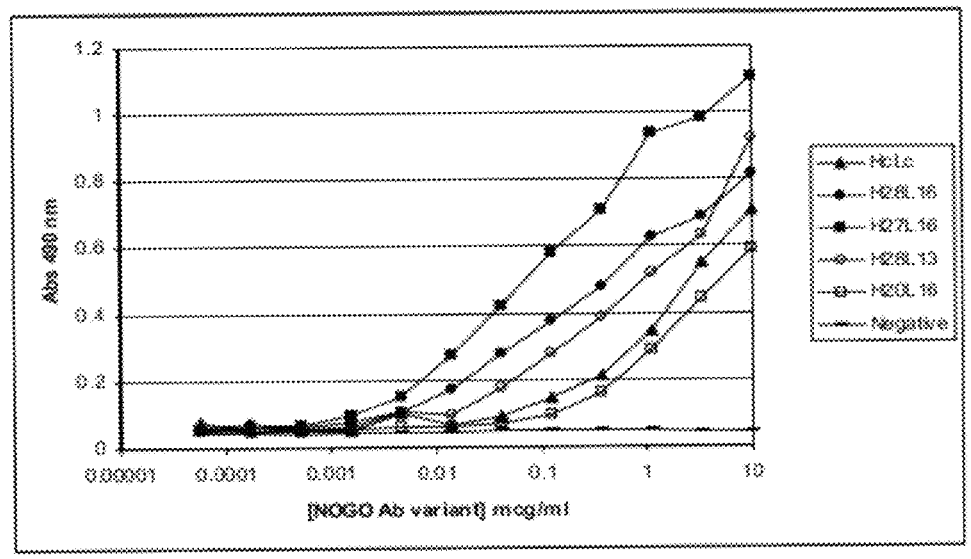

The ability of the antibodies to bind recombinant human Nogo-A (GST-human Nogo-A 56) was investigated by various related ELISA assays (performed in a related, but slightly different, protocol as that described in Example 3). In the first assay, the recombinant Nogo-A is directly coated to the plate at various different antigen concentrations. The results of the direct binding ELISA when the antigen is loaded at 1 mcg/ml or 0.05 mcg/ml are shown in FIG. 11A and FIG. 11B respectively. The data confirms that all the antibodies show comparable binding activity to recombinant human Nogo-A when compared with the chimeric form of the parental antibody (HcLc). At higher antigen coating concentrations, all antibodies yield a similar EC50 value. In contrast, at a lower antigen coating concentration the assay was able to discriminate between the antibodies. Although saturation curves were not obtained, a trend analysis on the lines revealed the following rank order: H27L16>H28L16, H28L13, H20L16.

Figure 12:
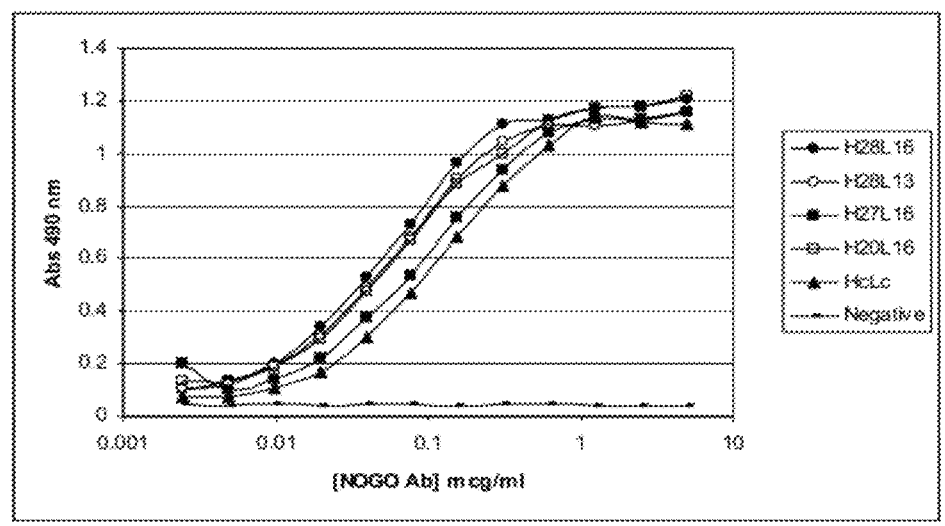
FIG. 12: Reverse format binding ELISA of the pre-candidate pool antibodies to recombinant human Nogo-A (GST-Nogo-A 5+6). The anti-Nogo-A antibodies were captured with anti-human IgG (Sigma, #I9764). The binding of recombinant GST-Nogo-A 5+6 was detected using an anti-GST- HRP conjugate (Sigma, #A7340). The negative control was an irrelevant antibody. EC50 values were derived using Robosage. The graph below shows a representative figure from three independent assays.

In a parallel experiment, the format of the assay was reversed. In this format, the antibody is captured on to the plate and the binding of the recombinant Nogo-A (GST-human Nogo-A-56) detected using the GST tag. The results of the reverse format ELISA are shown in FIG. 12. The data confirms that all the antibodies show comparable binding activity to recombinant human Nogo-A when compared with the chimeric form of the parental antibody (HcLc). This format of the binding ELISA did not distinguish between the antibodies.

11.2 Competition ELISA

Figure 13:
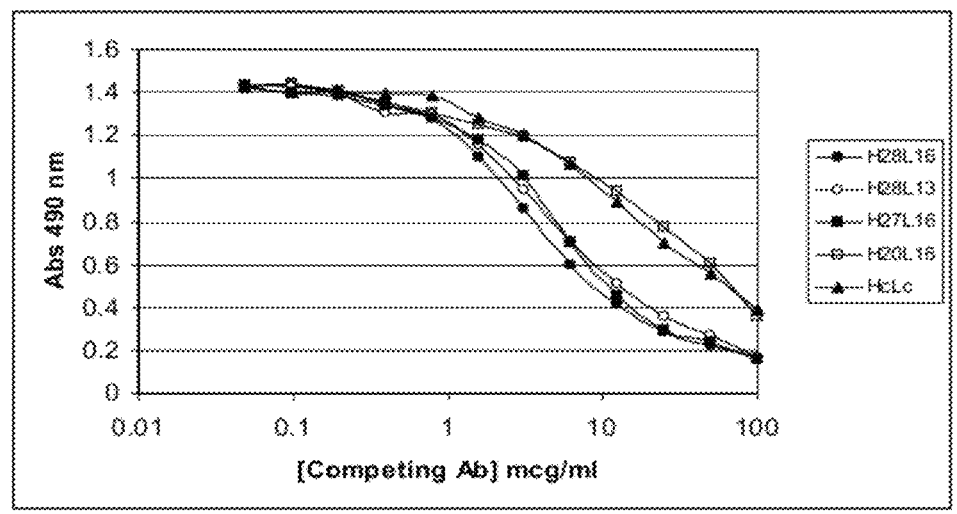
FIG. 13: Competition ELISA of the pre-candidate pool antibodies with the parental antibody 2A10. Recombinant human Nogo-A (GST-Nogo-A 5+6) was coated to the plates. 2A10 and the humanised antibodies pre-mixed and binding of 2A10 determined using an anti-mouse IgG-HRP conjugate (Dakocytomation, #P0260). The positive control was HcLc. IC50 values were derived using Robosage. The graph below shows a representative figure from three independent assays.

The ability of the antibodies to compete directly with the parental antibody for the same epitope on human Nogo-A was assessed using a competition ELISA. The recombinant human Nogo-A (GST-human Nogo-A 56) was coated onto the plates. The parental antibody 2A10 and the humanised antibodies were pre-mixed prior to adding to the plates. The binding of 2A10 was quantified using an anti-mouse IgG-HRP conjugate (Dakocytomation, #P0260). The results shown in FIG. 13 confirm that all four antibodies can compete with 2A10. This suggests that the humanised antibodies and parental antibody recognise an overlapping epitope on human Nogo-A. Furthermore, the activity of the humanised antibodies is comparable or better than the chimera HcLc. The results indicate that H27L16, H28L16 and H28L13 are more potent than H20L16.

11.3 Biacore Affinity Measurements

Biacore was used to determine affinities and rank antibodies using two different methodologies. In the first approach, the recombinant Nogo-A was coupled to the surface of the chip and anti-Nogo-A antibodies passed over this surface. In the second approach, Protein A was used to capture the antibody onto the surface of the chip over which the recombinant GST-human Nogo-A56 was passed. The results shown in Table 16 were obtained by coupling the antigen to the surface and confirm that all four antibodies show comparable/better affinity than the parental antibody (HcLc). Based on the average of six independent runs, the antibodies rank in the following order in terms of overall affinity: H27L16>H28L16>H28L13>H20L16, consistent with the rank order of the direct binding ELISA (FIG. 11B). In the case of H27L16 and H28L16, the humanised antibodies demonstrate 2-3× higher affinity that the parental antibody (HcLc).

TABLE 16

Binding kinetics of the anti-Nogo-A humanised antibodies to recombinant human Nogo-A (GST-human Nogo-A 56) as determined using the Biacore T100. The antigen was bound to the CM5 chip by primary amine coupling. The antibodies were flowed over a various concentrations (0.125-8 nM). The values show the mean and standard deviation (in brackets) of six independent runs carried out in duplicate. Each completed data set was analysed independently prior to the calculation of mean and standard deviation.

| Antibody | Ka | kd | KD (nM) |
|---|---|---|---|
| H20L16** | 5.37E6 (7.65E5) | 9.70E−3 (2.65E−3) | 1.80 (0.31) |
| H27L16 | 3.96E6 (9.93E5) | 2.30E−3 (1.11E−3) | 0.56 (0.15) |
| H28L13 | 8.13E6 (1.35E6) | 9.10E−3 (2.65E−3) | 1.11 (0.18) |
| H28L16 | 6.97E6 (6.62E5) | 4.43E−3 (1.18E−3) | 0.64 (0.15) |
| HcLc | 3.80E6 (7.11E5) | 7.09E−3 (2.22E−3) | 1.86 (0.32) |

**Only 11 sets of data analysed for H20L16 as one set could not be analysed.

In a similar manner to the ELISA, the kinetics of antibody binding to recombinant human Nogo-A (GST-human Nogo-A 56) was also assessed in a reverse format (see Example 11.1). In this assay, the humanised antibodies were captured onto the CM5 chip by Protein A. The averaged results for six independent runs are shown in Table 17. Consistent with the reverse format ELISA, all the humanised Nogo-A antibodies show similar binding kinetics to the chimera (HcLc) in the reverse format Biacore.

TABLE 17

Reverse format binding kinetics of the anti-Nogo-A humanised antibodies to recombinant human Nogo-A (GST Nogo-A 5 + 6) as determined using the Biacore T100. Protein A was immobilised to approximately 4000RUs by primary amine and used to capture 200-300RUs of the sample antibodies. Recombinant human Nogo-A was passed over at various concentrations (0.125-8 nM). The values show the mean and standard deviation (in brackets) of three independent runs in duplicate. Each data set was independently analysed prior to the calculation of the mean and standard deviation.

| Antibody | Ka | kd | KD (nM) |
|---|---|---|---|
| H20L16 | 1.01E6 (1.35E5) | 3.13E-4 (2.79E-5) | 0.31 (0.036) |
| H27L16 | 9.93E5 (2.02E4) | 3.04E-4 (1.83E-5) | 0.31 (0.019) |
| H28L13 | 1.12E6 (1.21E5) | 3.84E-4 (3.24E-5) | 0.34 (0.015) |
| H28L16 | 1.18E6 (8.32E4) | 4.01E-4 (2.48E-5) | 0.34 (0.032) |
| HcLc | 1.38E6 (3.70E5) | 5.69E-4 (1.54E-4) | 0.41 (0.062) |

11.4 Binding to Native Human NOGO

Figure 14:
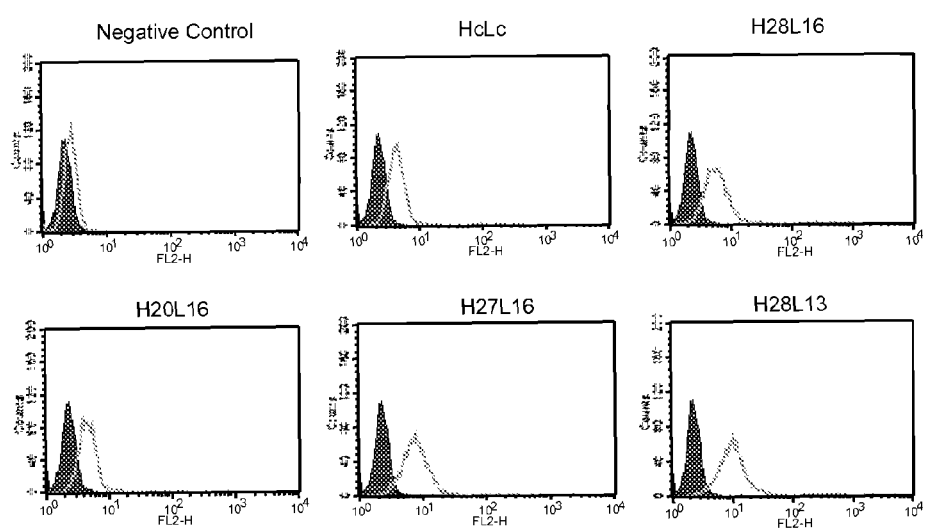
FIG. 14: Binding of the anti-Nogo-A humanised antibodies to cell-surface expressed human Nogo-A. CHO-K1 cells were engineered to express human Nogo-A. The cells were stained in duplicate with 100mcg/ml of the anti-Nogo-A humanised antibodies followed by a 1:100 dilution of the PE-labelled anti-human IgG secondary (Sigma, #P8047). An irrelevant antibody was included as a negative control. The data shown are a representative example of one of the duplicates.

To demonstrate that the humanised antibodies bind to native human Nogo-A with a profile comparable to the parental antibody, two flow cytometry based assays were developed. In the first assay, a CHO-K1-based cell line expressing human Nogo-A extracellular domain on the cell surface was generated. Binding of the humanised anti-Nogo-A antibodies was assessed by flow cytometry using a PE-labelled anti-human IgG (Sigma, #P8047). FIG. 14 below shows a typical profile for the anti-Nogo-A antibodies on the CHO-Nogo-A cell line. Whilst the assay is not sensitive enough to distinguish between the antibodies, the results confirm that all four antibodies can recognise cell surface expressed human Nogo-A at levels comparable to that of the chimera. None of the antibodies recognise the parental cell line (CHO-K1—data not shown).

Figure 15:
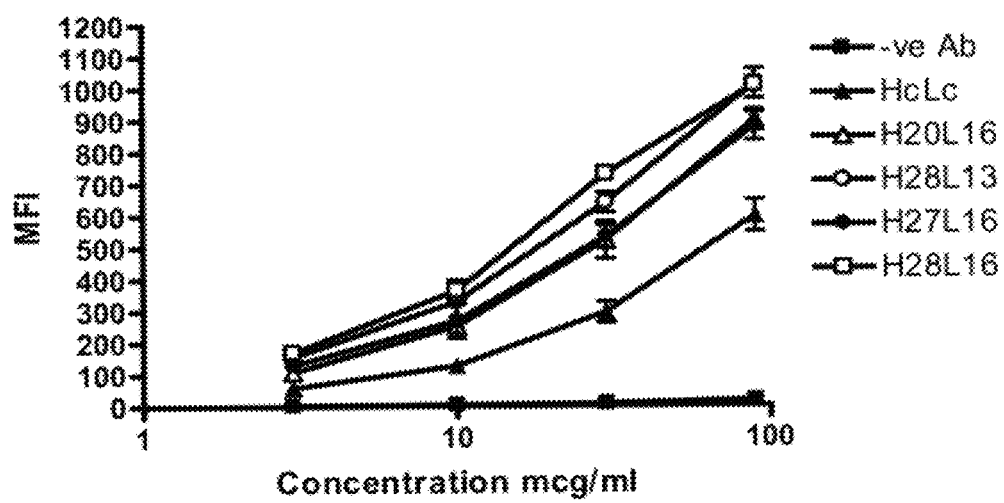
FIG. 15: Binding of the anti-Nogo-A humanised antibodies to intracellular human Nogo-A. IMR32 cells were permeabilised, fixed and stained with 3-90mcg/ml of the anti-Nogo-A humanised antibodies followed by 30 mcg/ml of the PE-labelled anti-human IgG secondary (Sigma P-9047). An irrelevant antibody was included as a negative control (–ve Ab). The data shown below is representative of three independent experiments.

In the second assay, the ability of the humanised antibodies to bind native Nogo-A was assessed using a human neuroblastoma cell line—IMR32. This cell line is characterised by high intracellular/low cell surface levels of Nogo-A protein. In an attempt to increase the binding signal, the assay was set-up to detect intracellular Nogo-A (ER-resident). IMR32 cells were permeabilised and fixed prior to staining with the anti-Nogo-A humanised antibodies. Binding of the antibodies to Nogo-A was detected using an anti-human IgG-PE labelled secondary (Sigma, #P8047). The results, shown in FIG. 15 below, confirm that all the antibodies bind to intracellular Nogo-A at levels comparable or higher than the parental antibody HcLc. These data, in conjunction with the results from the CHO-Nogo-A cell line, confirm that the humanised antibodies can recognise a more native form of the Nogo-A protein at levels comparable or better than the chimera, HcLc. The assays are not sufficiently sensitive to rank the antibody panel.

11.5 Neurite-Outgrowth Assays

Humanised anti-Nogo-A antibodies were tested for their ability to neutralise neurite-outgrowth (NO) inhibitory activity of Nogo-A in an assay that is based on quantifying NO as described previously. Antibodies tested in the assay were selected on the basis of their binding kinetics for Nogo-A. High affinity humanised antibodies namely, H28L16, H27L16, H20L16 and for reference their parental antibodies 2A10 (mouse monoclonal) and HcLc (human mouse chimera) were tested for Nogo-A neutralisation. For comparison, antibody 11C7 (see Example 13) was also tested in the assay.

Figure 16:
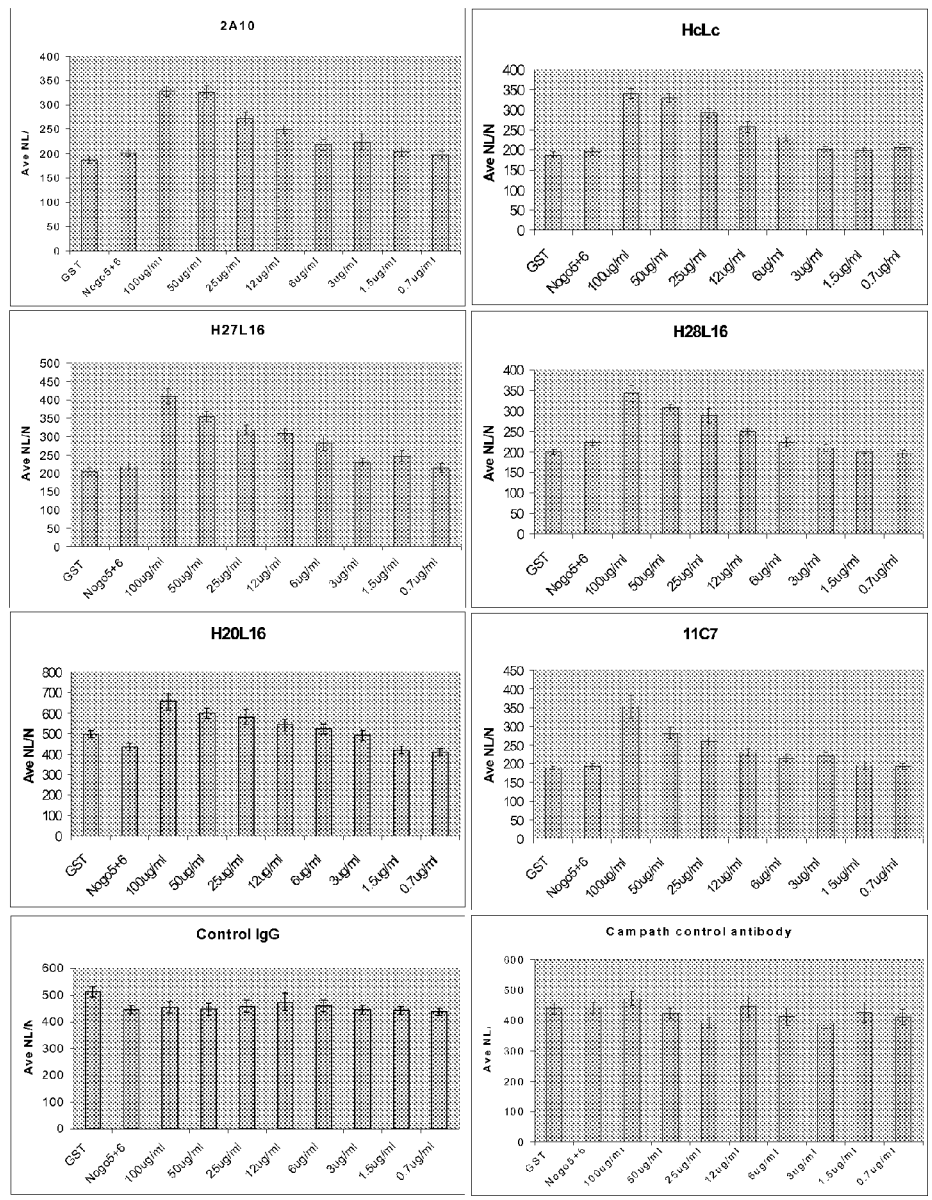
FIG. 16: Comparison of anti-Nogo-A humanised antibodies in the neurite outgrowth assay. H28L16, H27L16 and H20L16 were compared to the parental antibodies (2A10, HcLc), the antibody 11 C7 and various control antibodies (Control IgG and Campath). Increased neurite-outgrowth was only seen with anti-Nogo-A antibodies. The effects were dose-dependent and statistically significant.

In order to test the neutralising activity of selected humanised antibodies, wells coated with human recombinant GST-human Nogo-A56 and treated with varying concentrations of antibodies at 37° C. for 1 h prior to the addition of cerebellum granular neurons (CGNs). Control wells were treated with HBSS. Average neurite length per neurite was measured for each well. FIG. 16 shows the results for the humanised antibodies tested in the assay. A panel of control antibodies (control IgG, purified mouse IgG; Campath and another irrelevant humanised antibodies) used to confirm the specificity of the activity. As a further control, the same humanised antibodies were titrated onto GST coated plates. The results confirm that H28L16, H27L16 and H20L16 reverse Nogo-A-mediated inhibition of neurite outgrowth to a similar degree observed for the parental antibodies (2A10 and HcLc). The effects appear to be robust and stable and were seen with H28L16 in eight out of eleven independent neurite-outgrowth experiments. In contrast, the humanised antibodies do not increase neurite-outgrowth on GST coated plates and the panel of control antibodies do not show any dose dependent reversal of inhibition, confirming that the effect of the humanised antibodies is specific for Nogo-A-mediated inhibition. The data presented for the neurite outgrowth is selected from number of repeat experiments. Whilst a number of the repeats which are not shown appeared to be variable in nature, it is believed that the data shown reflects a true activity of the antibodies of the present invention in reducing the inhibitory effect of NOGO in the neurite outgrowth assay.

EXAMPLE 12

Further characterisation of H28L16

12.1 Binding to Full-Length Recombinant Nogo-A

The ability of the antibodies to bind full-length extracellular domain recombinant human Nogo-A (GST-human Nogo-A-ECD) was investigated by a direct binding ELISA assay. In this case the ECD was a splice variant falling within the region of approximately position 186-1004 of human NOGO A (the portion beginning DETFAL (SEQ ID NO.95) and ending with ELSKTS (SEQ ID NO.96)).

Figure 17:
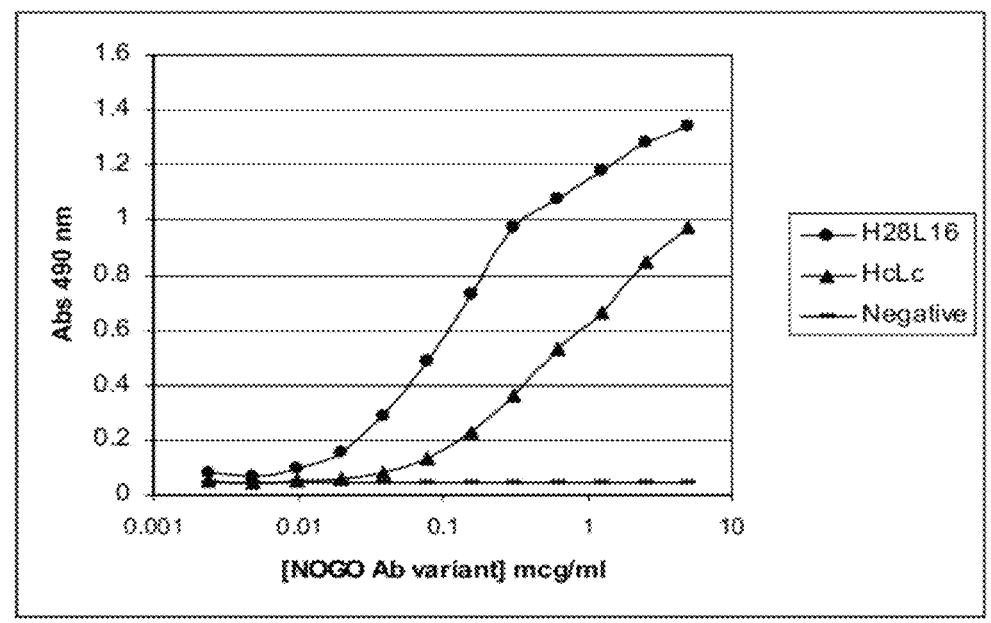
FIG. 17: Direct binding ELISA of H28L16 to recombinant full-length human Nogo-A splice (GST-Nogo-A- Biocat 113015). Recombinant Nogo-A splice was coated to the plates at 1.0mcg/ml. Binding of the antibodies was detected using an anti-human IgG-HRP conjugate (Sigma, #A7340X). The negative control was an anti β-amyloid antibody. EC50 values were derived using Robosage. The graph below shows a representative figure from two independent assays.

The recombinant GST-human Nogo-A-ECD was directly coated to the plate at 1 µg/ml. The data shown in FIG. 17 confirms that H28L16 can recognise GST-human Nogo-A-ECD as levels comparable or better than the parental (HcLc) or H20L16.

12.2 Inhibition of Fc Functionality

Figure 18:
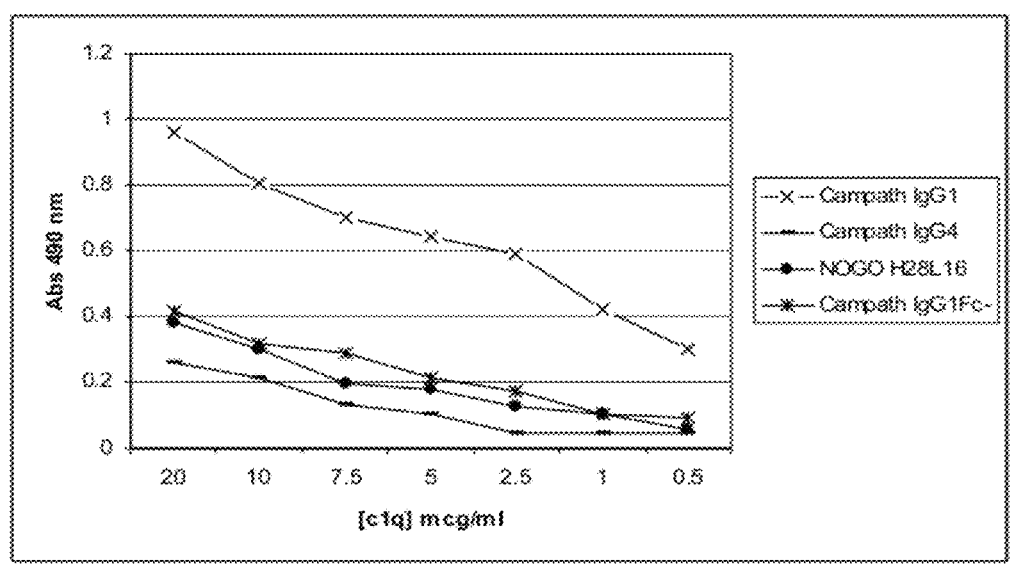
FIG. 18: H28L16 shows reduced C1q binding. ELISA plates were coated with a fixed concentration of the purified humanised and control antibodies (1mcg/ml). Human C1q (Sigma, C0660) was incubated with the antibodies and bound C1q quantified using an anti-human c1q-HRP conjugate (The Binding Site, PP020X). The control antibodies are Campath IgG1, Campath IgG4 and Campath IgG1 Fc-.

To improve the safety profile of the candidate, residues L235 and G237 within the CH2 domain of the heavy chain constant region (EU Index system) were mutated to alanine residues thus reducing the likelihood of triggering antibody-mediated immunological effector functions. Reduced human C1q binding was used as a surrogate for inhibition of Fc functionality. FIG. 18 below shows that H28L16 has significantly reduced C1q binding activity, compared to Campath-IgG1 (wild-type) and comparable to a Campath IgG1 construct bearing the same mutations (Fc-mutated antibody (Fc-)) and Campath IgG4. These data suggest that the CH2-domain mutations present in H28L16 will significantly reduce the likelihood of triggering Fc mediated effector functions.

12.3 Orthologue Binding

Figure 19:
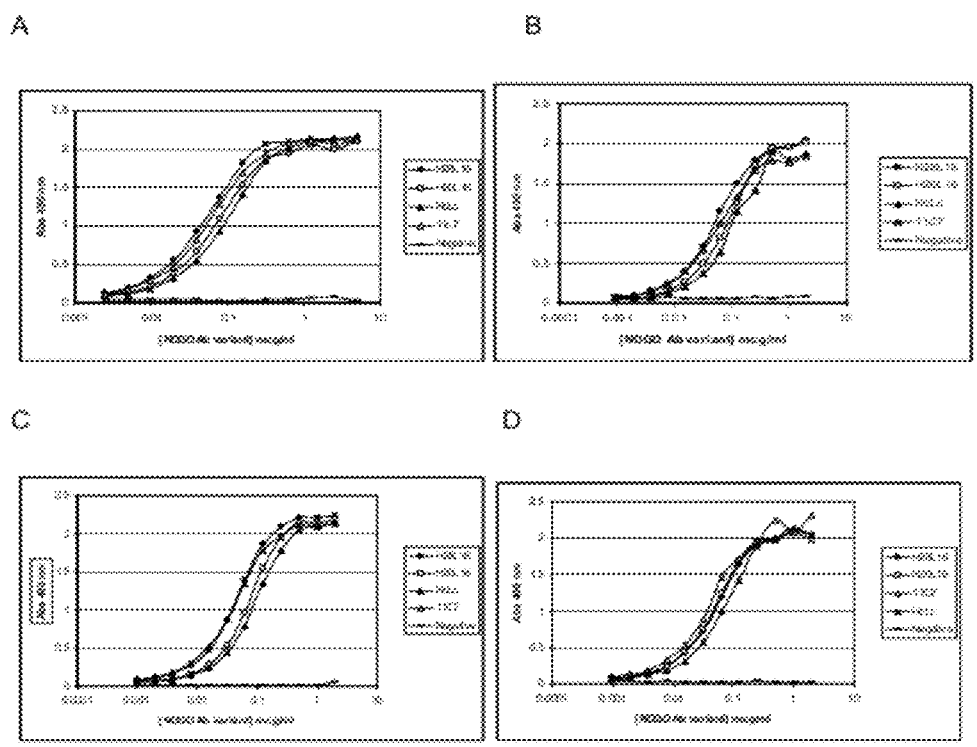
FIG. 19: Direct binding ELISA of H28L16, HcLc and 11 C7 to GST-NOGO-A56 from A) rat B) cynomolgus, C) marmoset and D) squirrel monkey. HcLc was included as a reference. An irrelevant antibody was included as a negative control. The graphs below shows a representative figure from three independent assays.

To confirm that H28L16 shows binding activity to various orthologues of Nogo-A, comparable to that of the parental antibody (HcLc), a series of binding assays were performed. FIG. 19 A-D below shows the results of a direct binding ELISA to recombinant NOGO (GST-human Nogo-A 56) from rat (SEQ ID NO.94), cynomolgus (SEQ ID NO. 92), marmoset (SEQ ID NO. 93) and squirrel monkey respectively (SEQ ID NO. 91). In all cases, H28L16 shows activity comparable or better than the chimeric antibody (HcLc). The calculated EC50 values are very similar to those calculated for binding to human recombinant Nogo-A.

The kinetics of binding of H28L16 to the various orthologues of Nogo-A in comparison to HcLc and 11C7 was determined using the Biacore. Table 18 and Table 19 below show the kinetics of binding in two different formats of the assay. Where the recombinant Nogo-A was coupled directly to the CM5 chip (Table 18), the binding kinetics for rat, cynomolgus monkey, squirrel monkey and marmoset are very similar to that for human (range=0.33-0.67 nM). When the format of the assay was reversed and the antibodies are captured onto the chip using Protein A (Table 19), the binding affinity of H28L16 to rat Nogo-A is approximately 4-fold lower than for human Nogo-A. A similar trend is observed for cynomolgus Nogo-A (8.5× lower affinity than human) and the other primate orthologues (12-17× lower affinity than human). The chimeric antibody HcLc shows a similar profile of binding to the orthologues of Nogo-A in both orientations of the assay. Since it is unclear which assay format best represents the in vivo situation, the primary conclusions that can be drawn from this study are 1) H28L16 has retained the orthologue cross-reactivity profile associated with the chimeric antibody HcLc and 2) the affinity of HcLc for rat and cynomolgus Nogo-A is within 4-fold and 8.5-fold of the affinity for human Nogo-A and under certain conditions may be very similar.

TABLE 18

Binding kinetics of H28L16, 11C7 and HcLc to the recombinant orthologues of human Nogo-A as determined using the Biacore T100. Approximately 140-180RUs of the various Nogo-A orthologues were captured to the CM5 chip by primary amine coupling. The antibodies were flowed over a various concentrations (0.125-8 nM). The values show the mean and standard deviation (in brackets) of 1-2 independent runs carried out in duplicate with each data set independently analysed prior to calculation of the mean and standard deviation.

| | H28L16 | | | 11C7 | | | HcLc | | |
|---|---|---|---|---|---|---|---|---|---|
| Orthologue | Ka | Kd | KD (nM) | Ka | Kd | KD (nM) | Ka | Kd | KD (nM) |
| Cynomolgus | 4.65E6 | 3.07E−3 | 0.67 | 1.47E6 | 3.40E−4 | 0.23 | 2.94E6 | 4.78E−3 | 1.68 |
| (2 runs)* | (7.47E5) | (2.37E−4) | (0.06) | (1.67E5) | (4.45E−5) | (0.01) | (7.13E5) | (6.34E−4) | (0.35) |
| Rat | 4.64E6 | 1.54E−3 | 0.33 | 8.36E5 | 1.20E−4 | 0.11 | 2.53E6 | 2.83E−3 | 1.12 |
| (2 runs) | (2.34E5) | (3.06E−5) | (0.01) | (5.58E5) | (2.14E−5) | (0.03) | (5.32E4) | (2.30E−5) | (0.03) |
| Marmoset | 4.2E6 | 3.02E−3 | 0.626 | 1.16E6 | 2.80E−4 | 0.24 | 3.13E6 | 4.44E−3 | 1.419 |
| (1 run) | (2.47E4) | (5.09E−5) | (0.000) | (5.37E4) | (6.15E−6) | (0.006) | (2.76E4) | (1.41E−4) | (0.03) |
| Squirrel Monkey | 4.46E6 | 2.73E−3 | 0.61 | 1.10E6 | 2.86E−4 | 0.26 | 3.04E6 | 4.68E−3 | 1.54 |
| (1 run) | (6.08E4) | (4.95E−6) | (0.000) | (3.25E4) | (1.87E−5) | (0.010) | (1.64E5) | (2.11E−4) | (0.15) |
| Human | 6.97E6 | 4.43E−3 | 0.64 | 1.58E6 | 2.64E−4 | 0.19 | 3.80E6 | 7.09E−3 | 1.86 |
| | (6.62E5) | (1.18E−3) | (0.15) | (6.42E5) | (5.57E−5) | (7.96E−2) | (7.11E5) | (2.22E−3) | (0.32) |

*One set of curves was discarded due to uninterpretable curves for antibody 11C7.

TABLE 19

Reverse format binding kinetics of H28L16, 11C7 and HcLc to the recombinant orthologues of human Nogo-A as determined on the Biacore T100. Protein A was immobilised on the surface at about 4000RUs and anti-Nogo-A antibodies were captured at approximately 300-400RUs. The recombinant proteins (GST-NOGO-A56) were flowed over a various concentrations (0.125-64 nM) dependent on the construct. All the runs were done in duplicates. The values show the mean and standard deviation (in brackets) of 1-3 independent runs with each run done in duplicate and each data set analysed independently prior to calculation of the mean and standard deviation.

| | H28L16 | | | 11C7 | | | HcLc | | |
|---|---|---|---|---|---|---|---|---|---|
| Orthologue | Ka | Kd | KD (nM) | Ka | Kd | KD (nM) | Ka | Kd | KD (nM) |
| Cynomolgus | 3.26E5 | 1.11E−3 | 3.41 | 4.02E5 | 2.97E−4 | 0.76 | 3.03E5 | 1.41E−3 | 4.66 |
| (3 runs) | (4.06E3) | (2.23E−5) | (0.05) | (6.85E4) | (1.11E−5) | (0.12) | (4.58E3) | (2.84E−5) | (0.08) |
| Rat | 3.80E5 | 6.69E−4 | 1.76 | 2.83E5 | 1.77E−4 | 0.64 | 5.47E5 | 1.10E−3 | 2.01 |
| (3 runs) | (5.68E3) | (1.24E−5) | (0.03) | (4.66E4) | (1.34E−5) | (0.09) | (1.20E4) | (2.86E−5) | (0.07) |
| Marmoset | 2.22E5 | 1.09E−3 | 4.89 | 1.91E5 | 2.54E−4 | 1.33 | 3.02E5 | 1.36E−3 | 4.51 |
| (1 run) | (3.61E3) | (7.35E−5) | (0.25) | (2.90E3) | (3.46E−6) | (0.00) | (9.90E2) | (7.92E−5) | (0.28) |
| Squirrel Monkey | 1.57E5 | 1.08E−3 | 6.86 | 1.03E5 | 2.78E−4 | 2.69 | 1.74E5 | 1.29E−3 | 7.45 |
| (1 run) | (2.69E3) | (5.02E−5) | (0.20) | (2.12E3) | (3.61E−6) | (0.02) | (2.19E3) | (7.64E−5) | (0.34) |
| Human | 1.20E6 | 4.75E−4 | 0.40 | 2.64E5 | 1.49E−4 | 0.57 | 1.32E6 | 7.00E−4 | 0.54 |
| (1 run) | (8.49E4) | (9.97E−6) | (0.02) | (3.32E3) | (1.61E−5) | (0.07) | (2.71E5) | (3.18E−5) | (0.09) |

12.4 Physical Properties

The physicochemical properties of H28L16 and H20L16 were assessed by SEC-HPLC and SDS-PAGE. SEC-HPLC was carried out at 1.0 ml/minute using 100 mM sodium phosphate, 400 mM sodium chloride pH 6.8 and a TSK G3000 SW xl 30 cm×7.8 mm stainless steel column with detection at 214 nm and 280 nm. SDS-PAGE was carried out on a 4-20% Novex Tris-HCL gel loading 10 μg product and staining with Sypro Ruby. C-IEF was carried out on a Beckman MDQ using pH 3.5-10 ampholines.

The following results were obtained:

TABLE 20

Size exclusion chromatography (SEC) HPLC analysis of the anti-Nogo-A antibodies. The values shown are percentages of the antibody assigned to each of the three different species.

| Antibody | Aggregate % | Monomer % | Fragment % |
|---|---|---|---|
| H28L16 | 0.50 | 99.50 | 0.00 |
| H20L16 | 14.21 | 85.75 | 0.05 |

TABLE 21

SDS-PAGE analysis of the anti-Nogo-A antibodies. The values shown are percentages of the antibody found in the major bands.

| Antibody | Non-reduced | Reduced |
|---|---|---|
| H28L16 | 82.4% | HC: 67.2% |
|  |  | LC: 27.7% |
|  |  | H + L: 94.9% |
| H20L16 | 84.6% | HC: 69.3% |
|  |  | LC: 26.4% |
|  |  | H + L: 95.7% |

The SEC-HPLC data suggests that H20L16 is more susceptible to aggregation than H28L16 (H28L16). If the data reported here were to be repeated at large scale, this could impact the ability of the manufacturing process to produce material of acceptable quality for clinical use (>95% monomer). The SDS-PAGE data shows both candidates are acceptable with both showing a typical profile.

EXAMPLE 13

Comparison of H28L16 with 11C7

Figure 20:
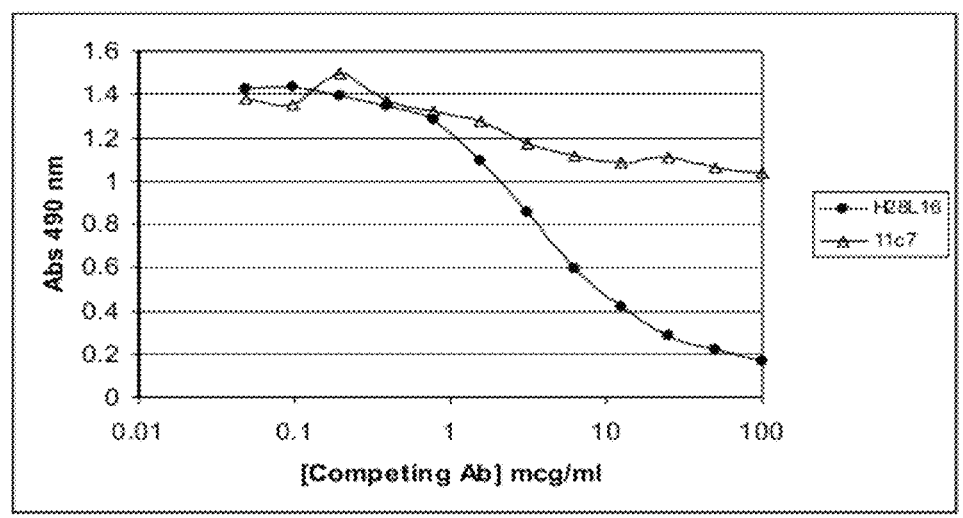
FIG. 20: Competition ELISA to compare the binding epitopes of H28L16 and 11 C7. Recombinant human Nogo-A (GST-Nogo-A 5+6) was coated to the plates. 2A10 and either 11 C7 or H28L16 were pre-mixed and binding of 2A10 determined using an anti-mouse IgG-HRP conjugate (Dakocytomation, #P0260). IC50 values were derived using Robosage. The graph below shows a representative figure from three independent assays.

A murine anti-Nogo-A antibody designated 11C7 is described in WO2004052932, which was raised to a peptide epitope. A chimeric 11C7 was made based on the sequence information provided in WO2004052932. To compare the binding epitopes of 2A10 and 11C7, a competition ELISA was established to investigate if 11C7 and 2A10 recognise an overlapping epitope on Nogo-A. As shown in FIG. 20 below, HcLc (the chimeric form of 2A10) was able to compete with 2A10 for binding to human recombinant Nogo-A whereas 11C7 showed no competition with 2A10, even at concentrations of up to 100 mcg/ml.

EXAMPLE 14

Competition ELISA to Demonstrate the Ability of Peptides to Compete Directly with Human NOGO-5+6 for Binding to NOGO H28L16

Method for competition ELISA

The ability of peptides to compete directly with NOGO-A (GST-human Nogo-A56) for binding to NOGO H28L16 was assessed using a competition ELISA. Rabbit anti-human IgG (Sigma, #I-9764) at 5 g/ml in bicarbonate buffer was coated onto Nunc immunosorp plates (100 ul per well) at 4° C. overnight. The plates were rinsed 3 times with TBS containing 0.05% Tween (TBST) then blocked with 1% BSA in TBST at room temperature for 1 hour. H28L16 was then captured onto the plate (1 ug/ml, diluted in 1% BSA in TBST, 50 ul per well) at room temperature for 1 hour. The plates were washed 3 times with TBST. Peptides (from 0 to 100 g/ml) and GST-human NOGO-A56 at a concentration of 1 ug/ml (diluted in 1% BSA in TBST) were pre-mixed prior to addition into the wells and incubated at room temperature for 1 hour. The plates were washed 3 times with TBST then incubated for 1 hour with rabbit anti-GST peroxidase conjugate (Sigma, #A7340, 1:2000, diluted in 1% BSA in TBST) for 1 hour. The plates were washed 3 times with TBST and then incubated with 50 I OPD peroxidase substrate (Sigma) per well for 10 minutes. The colour reaction was stopped by the addition of 25 I concentrated $H_2SO_4$. Absorbance at 490 nm was measured using a plate reader.

Figure 21:
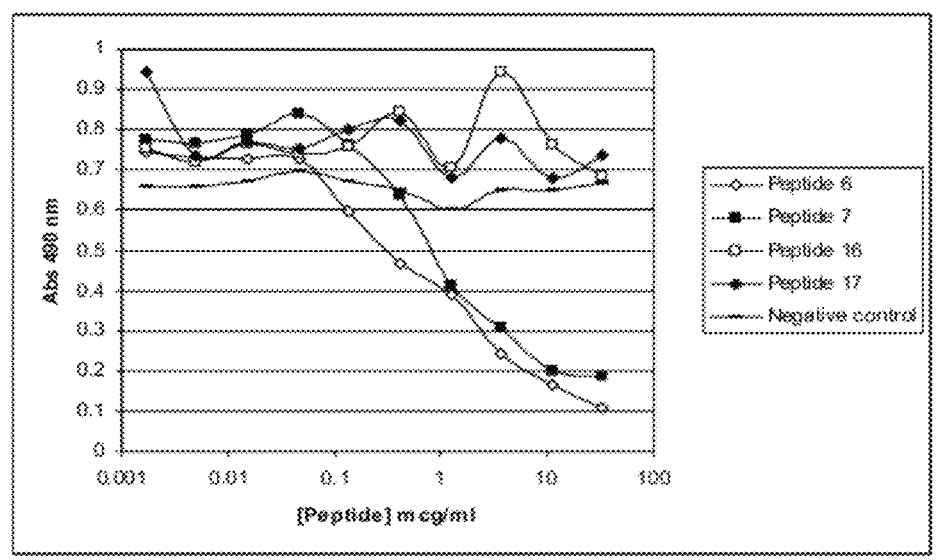
FIG. 21: Competition ELISA to compare the binding of NOGO-5+6 (GST-Nogo-A 5+6) and peptide fragments to H28L16. The graph below shows a representative figure from two independent assays.

The results shown in FIG. 21 confirm that peptides 6 and 7, which were positive in the epitope mapping ELISA (Example 8) can compete with GST-human NOGO-A56 binding to H28L16. This suggests that the peptides which were positive in the epitope mapping study contain an epitope for H28L16 binding. Peptides 16 and 17 (which contain NOGO peptides, but not overlapping with peptides 6 or 7), which do not contain the proposed epitope, do not compete with NOGO-5+6.

EXAMPLE 15

ELISA analysis of a humanised Anti NOGO Monoclonal Antibody Based on the NOGO Antibody Variant G101S/Q37R G101S (also known as H100 (SEQ ID NO.63)), a modified variant of the heavy chain variable region of H6 (SEQ ID NO.11) was generated by introducing a single substitution, G101S (Kabat numbering) into CDR H3 as described above. Similarly, Q37R, a modified variant of the light chain variable region of L13 (SEQ ID NO. 13) were generated by introducing a single substitution (Kabat numbering Q37R) into the framework region (to form L100). The protein sequence of the variable light domain Q37R is given in SEQ ID NO. 67.

Genes encoding full length versions of the heavy and light chains containing the G101S/Q37R substitutions were expressed in CHO cells as described previously and assayed in a direct binding ELISA as described previously.

Figure 22:
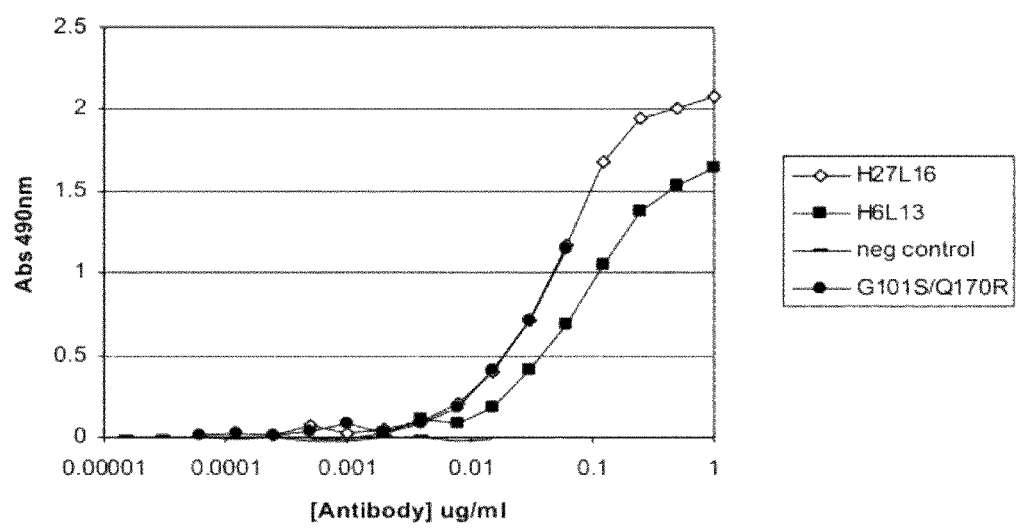
FIG. 22: ELISA data for the G101S/Q37R variant in comparison with H6L13 and H27L16.

The results of the direct binding ELISA when the antigen is loaded at 0.05 ug/ml are shown in FIG. 22. The data confirms that antibody H100L100 shows comparable binding activity to recombinant GST-human NOGO-A56 when compared with H27L16 and that H100L100 has an improved binding profile when compared to H6L13. Corresponding EC50 values are shown in the table below:

TABLE 22

EC50 measurements for the G101S/Q37R variant in comparison with H6L13 and H27L16

| Antibody | EC50 value |
|---|---|
| H6L13 | 0.086 |
| H27L16 | 0.052 |
| H100/L100 | 0.048 |

EXAMPLE 16

BiaCore Analysis of Humanised Anti NOGO Monoclonal Antibodies Based on the CDR H3 Variant G101S H100, A modified variant of the heavy chain variable region of H6 (SEQ ID NO.11) was generated by introducing a single substitution, G101S (Kabat numbering) into CDR H3. The protein sequence of the variable heavy domain H100 protein is given in SEQ ID NO.63. Similarly, L100 and L101, modified variants of the light chain variable region of L13 (SEQ ID NO. 13) were generated by introducing a single substitution (Kabat numbering Q37R and Q45R respectively) into the framework region. The protein sequences of the variable light domains L100 and L101 proteins are given in SEQ ID NO.67 and SEQ ID NO.68 respectively.

Full length versions of H100L100 and H100L101 were expressed in CHO cells as described previously. Table 23 shows a comparison of the binding affinities of H6L13 with H100L100 and H100L101 and indicates that H100L100 and H100L101 have an improved binding affinity when compared with H6L13. In this example, the method was performed essentially as described in Example 6 where the CM5 chip was activated by passing the NHS and EDC solutions over the chip at 5 µl/ml for 7 minutes and the NOGO was suspended in 10 nM sodium acetate buffer (pH 4.5) before passing over the chip.

TABLE 23

Biacore measurements for the G101S variants of the H6 variable heavy chain in combination with variants of the L13 variable light chain in comparison with H6L13.

| Antibody | On rate ka (1/Ms) | Off-rate kd (1/s) | Affinity (KD, nM) |
|---|---|---|---|
| H6L13 | 1.04E+06 | 7.22E−03 | 6.97 |
| H100L100 | 1.28E+07 | 5.07E−03 | 0.396 |
| H100L101 | 1.30E+07 | 4.29E−03 | 0.329 |

TABLE 24

NOGO antibody sequences Summary (Table 24)

| Description | amino acid sequence | Polynucleotide sequence |
|---|---|---|
| 2A10, CDR-H1 | 1 | — |
| 2A10, CDR-H2 | 2 | — |
| 2A10, CDR-H3 | 3 | — |
| 2A10, CDR-L1 | 4 | — |
| 2A10, CDR-L2 | 5 | — |
| 2A10, CDR-L3 | 6 | — |
| 2A10, VH (murine) | 7 | 19 |
| 2A10, VL (murine) | 8 | 20 |
| Chimeric heavy chain Hc | 9 | 21 |
| Chimeric light chain Lc | 10 | 22 |
| 2A10 VH humanised construct H6 | 11 | 23 |
| 2A10 VH humanised construct H16 | 12 | 24 |
| 2A10 VL humanised construct L13 | 13 | 25 |
| 2A10 VL humanised construct L16 | 14 | 26 |
| 2A10 heavy chain humanised construct H6 | 15 | 27 |
| 2A10 heavy chain humanised construct H16 | 16 | 28 |
| 2A10 light chain humanised construct L13 | 17 | 29 |
| 2A10 light chain humanised construct L16 | 18 | 30 |
| Campath leader sequence | 31 | — |
| Amino acids 586-785 of human NOGO A (NOGO-A56) fused to GST | 32 | — |
| 2A10 VH humanised construct H1 | 33 | 37 |
| 2A10 VL humanised construct L11 | 34 | 38 |
| 2A10 heavy chain humanised construct H1 | 35 | 39 |
| 2A10 light chain humanised construct L11 | 36 | 40 |
| 2A10 VH humanised construct H20 | 41 | 43 |
| 2A10 heavy chain humanised construct H20 | 42 | 44 |
| 2A10, CDR-H3 (G95M) | 45 | |
| Sequence of Marmoset NOGO-A fragment | 46 | |
| VH humanised construct H26 | 47 | 50 |
| VH humanised construct H27 | 48 | 51 |
| VH humanised construct H28 | 49 | 52 |
| Heavy chain humanised construct H26 | 53 | 56 |
| Heavy chain humanised construct H27 | 54 | 57 |
| Heavy chain humanised construct H28 | 55 | 58 |
| Chimeric heavy chain Hc (G95M) | 59 | |
| Epitope | 60 | |
| 2A10 VH humanised construct H99 | 61 | |
| CDR (G101S) | 62 | |
| VH humanised construct H100 | 63 | |
| VH humanised construct H101 | 64 | |
| VH humanised construct H102 | 65 | |
| VH humanised construct H98 | 66 | |
| L100 (L13 + Q37R) | 67 | |
| L101 (L13 + Q45R) | 68 | |
| L102 (L13 + Q37R/Q45R) | 69 | |
| L103 (L16 + Q37R) | 70 | |
| L104 (L16 + Q45R) | 71 | |
| L105 (L16 + Q37R/Q45R) | 72 | |
| Peptide | 73 | |
| peptide | 74 | |
| CDR H3 analogue | 75 | |
| CDR H3 analogue | 76 | |
| CDR H3 analogue | 77 | |
| CDR H3 analogue | 78 | |
| CDR H3 analogue | 79 | |
| CDR H3 analogue | 80 | |
| CDR H3 analogue | 81 | |
| CDR H3 analogue | 82 | |
| CDR H3 analogue | 83 | |
| CDR H3 analogue | 84 | |
| NOGO peptide | 85 | |
| CDR H3 analogue | 86 | |
| CDR H3 analogue | 87 | |
| CDR H3 analogue | 88 | |
| CDR H3 analogue | 89 | |
| CDR H3 analogue | 90 | |
| Squirrel monkey NOGO (A56) plus GST tag | 91 | |
| Cynomolgus monkey NOGO (A56) plus GST tag | 92 | |
| Marmoset NOGO (A56) plus GST tag | 93 | |
| Rat NOGO (A56) plus GST tag | 94 | |
| Human NOGO peptide | 95 | |
| Human NOGO peptide | 96 | |

Sequences
SEQ ID NO. 1: 2A10 CDR-H1
SYWMH

SEQ ID NO. 2: 2A10 CDR-H2
NINPSNGGTNYNEKFKS

SEQ ID NO. 3: 2A10 CDR-H3
GQGY

SEQ ID NO. 4: 2A10 CDR-L1
RSSKSLLYKDGKTYLN

SEQ ID NO. 5: 2A10 CDR-L2
LMSTRAS

SEQ ID NO. 6: 2A10 CDR-L3
QQLVEYPLT

SEQ ID NO. 7: 2A10, VH (murine)
QVQLQQPGTELVKPGASVKLSCKASGYTFTSYWMHWVKQRPGQGLEWIGNINPSNGGTNYNEKFKSKATLTV

DKSSSTAYMQLSSLTSEDSAVYYCELGQGYWGQGTTLTVSS

SEQ ID NO. 8: 2A10, VL (murine)
DIVITQDELSNPVTSGESVSISCRSSKSLLYKDGKTYLNWFLQRPGQSPQLLIYLMSTRASGVSDRFSGSGS

GTDFTLEISRVKAEDVGVYYCQQLVEYPLTFGAGTKLELK

SEQ ID NO. 9: Chimeric heavy chain Hc
MGWSCIILFLVAAATGVHSQVQLQQPGTELVKPGASVKLSCKASGYTFTSYWMHWVKQRPGQGLEWIGNINP

SNGGTNYNEKFKSKATLTVDKSSSTAYMQLSSLTSEDSAVYYCELGQGYWGQGTLVTVSSASTKGPSVFPLA

PSSKSTSGGTAALGCLVKDYFPEPVTVSWNSGALTSGVHTFPAVLQSSGLYSLSSVVTVPSSSLGTQTYICN

VNHKPSNTKVDKKVEPKSCDKTHTCPPCPAPELAGAPSVFLFPPKPKDTLMISRTPEVTCVVVDVSHEDPEV

KFNWYVDGVEVHNAKTKPREEQYNSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTTPPVLDSDGSFFLYSKLTVDKSRW

QQGNVFSCSVMHEALHNHYTQKSLSLSPGK

SEQ ID NO. 10: Chimeric light chain Lc
MRCSLQFLGVLMFWISGVSGDIVITQDELSNPVTSGESVSISCRSSKSLLYKDGKTYLNWFLQRPGQSPQLL

IYLMSTRASGVSDRFSGSGSGTDFTLEISRVKAEDVGVYYCQQLVEYPLTFGAGTKLELKRTVAAPSVFIFP

PSDEQLKSGTASVVCLLNNFYPREAKVQWKVDNALQSGNSQESVTEQDSKDSTYSLSSTLTLSKADYEKHKV

YACEVTHQGLSSPVTKSFNRGEC

SEQ ID 11: 2A10 VH humanised construct H6
QVQLVQSGAEVKKPGASVKVSCKASGYTFTSYWMHWVRQAPGQGLEWIGNINPSNGGTNYNEKFKSRATMTR

DTSTSTAYMELSSLRSEDTAVYYCELGQGYWGQGTLVTVSS

SEQ ID NO. 12 2A10 VH humanised construct H16
QVQLVQSGAEVKKPGASVKVSCKASGYTFTSYWMHWVKQRPGQGLEWIGNINPSNGGTNYNEKFKSKATLTV

DKSTSTAYMELSSLRSEDTAVYYCELGQGYWGQGTLVTVSS

SEQ ID NO. 13: 2A10 VL humanised construct L13
DIVMTQSPLSLPVTLGQPASISCRSSKSLLYKDGKTYLNWFQQRPGQSPQLLIYLMSTRASGVPDRFSGGGS

GTDFTLKISRVEAEDVGVYYCQQLVEYPLTFGQGTKLEIK

SEQ ID NO. 14: 2A10 VL humanised construct L16
DIVMTQSPLSNPVTLGQPVSISCRSSKSLLYKDGKTYLNWFLQRPGQSPQLLIYLMSTRASGVPDRFSGGGS

GTDFTLKISRVEAEDVGVYYCQQLVEYPLTFGQGTKLEIK

SEQ ID NO. 15: 2A10 heavy chain humanised construct H6
MGWSCIILFLVATATGVHSQVQLVQSGAEVKKPGASVKVSCKASGYTFTSYWMHWVRQAPGQGLEWIGNINP

SNGGTNYNEKFKSRATMTRDTSTSTAYMELSSLRSEDTAVYYCELGQGYWGQGTLVTVSSASTKGPSVFPLA

PSSKSTSGGTAALGCLVKDYFPEPVTVSWNSGALTSGVHTFPAVLQSSGLYSLSSVVTVPSSSLGTQTYICN

VNHKPSNTKVDKKVEPKSCDKTHTCPPCPAPELAGAPSVFLFPPKPKDTLMISRTPEVTCVVVDVSHEDPEV

KFNWYVDGVEVHNAKTKPREEQYNSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTTPPVLDSDGSFFLYSKLTVDKSRW

QQGNVFSCSVMHEALHNHYTQKSLSLSPGK

SEQ ID NO. 16: 2A10 heavy chain humanised construct H16
MGWSCIILFLVATATGVHSQVQLVQSGAEVKKPGASVKVSCKASGYTFTSYWMHWVKQRPGQGLEWIGNINP

SNGGTNYNEKFKSKATLTVDKSTSTAYMELSSLRSEDTAVYYCELGQGYWGQGTLVTVSSASTKGPSVFPLA

PSSKSTSGGTAALGCLVKDYFPEPVTVSWNSGALTSGVHTFPAVLQSSGLYSLSSVVTVPSSSLGTQTYICN

VNHKPSNTKVDKKVEPKSCDKTHTCPPCPAPELAGAPSVFLFPPKPKDTLMISRTPEVTCVVVDVSHEDPEV

KFNWYVDGVEVHNAKTKPREEQYNSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTTPPVLDSDGSFFLYSKLTVDKSRW

QQGNVFSCSVMHEALHNHYTQKSLSLSPGK

SEQ ID NO. 17: 2A10 light chain humanised construct L13
MGWSCIILFLVATATGVHSDIVMTQSPLSLPVTLGQPASISCRSSKSLLYKDGKTYLNWFQQRPGQSPQLLI

YLMSTRASGVPDRFSGGGSGTDFTLKISRVEAEDVGVYYCQQLVEYPLTFGQGTKLEIKRTVAAPSVFIFPP

SDEQLKSGTASVVCLLNNFYPREAKVQWKVDNALQSGNSQESVTEQDSKDSTYSLSSTLTLSKADYEKHKVY

ACEVTHQGLSSPVTKSFNRGEC

SEQ ID NO. 18: 2A10 light chain humanised construct L16
MGWSCIILFLVATATGVHSDIVMTQSPLSNPVTLGQPVSISCRSSKSLLYKDGKTYLNWFLQRPGQSPQLLI

YLMSTRASGVPDRFSGGGSGTDFTLKISRVEAEDVGVYYCQQLVEYPLTFGQGTKLEIKRTVAAPSVFIFPP

SDEQLKSGTASVVCLLNNFYPREAKVQWKVDNALQSGNSQESVTEQDSKDSTYSLSSTLTLSKADYEKHKVY

ACEVTHQGLSSPVTKSFNRGEC

SEQ ID NO. 19: PN encoding 2A10, VH (murine) SEQ ID: 7
CAGGTCCAACTGCAGCAGCCTGGGACTGAACTGGTGAAGCCTGGGGCTTCAGTGAAGCTGTCCTGCAAGGCT

TCTGGCTACACCTTCACCAGCTACTGGATGCACTGGGTGAAGCAGAGGCCTGGACAAGGCCTTGAGTGGATT

GGAAATATTAATCCTAGCAATGGTGGTACTAACTACAATGAGAAGTTCAAGAGCAAGGCCACACTGACTGTA

GACAAATCCTCCAGCACAGCCTACATGCAGCTCAGCAGCCTGACATCTGAGGACTCTGCGGTCTATTATTGT

GAACTGGGACAGGGCTACTGGGGCCAAGGCACCACTCTCACAGTCTCCTCA

SEQ ID NO. 20: PN encoding 2A10, VL (murine) SEQ ID: 8
GATATTGTGATAACCCAGGATGAACTCTCCAATCCTGTCACTTCTGGAGAATCAGTTTCCATCTCCTGCAGG

TCTAGTAAGAGTCTCCTATATAAGGATGGGAAGACATACTTGAATTGGTTTCTGCAGAGACCAGGACAATCT

CCTCAGCTCCTGATCTATTTGATGTCCACCCGTGCATCAGGAGTCTCAGACCGGTTTAGTGGCAGTGGGTCA

GGAACAGATTTCACCCTGGAAATCAGTAGAGTGAAGGCTGAGGATGTGGGTGTGTATTACTGTCAACAACTT

GTAGAGTATCCGCTCACGTTCGGTGCTGGGACCAAGCTGGAGCTGAAA

SEQ ID NO. 21: PN encoding Chimeric heavy chain Hc SEQ ID: 9
ATGGGATGGAGCTGTATCATCCTCTTTTTGGTAGCAGCAGCTACAGGTGTCCACTCCCAGGTCCAACTGCAG

CAGCCTGGGACTGAACTGGTGAAGCCTGGGGCTTCAGTGAAGCTGTCCTGCAAGGCTTCTGGCTACACCTTC

ACCAGCTACTGGATGCACTGGGTGAAGCAGAGGCCTGGACAAGGCCTTGAGTGGATTGGAAATATTAATCCT

AGCAATGGTGGTACTAACTACAATGAGAAGTTCAAGAGCAAGGCCACACTGACTGTAGACAAATCCTCCAGC

ACAGCCTACATGCAGCTCAGCAGCCTGACATCTGAGGACTCTGCGGTCTATTATTGTGAACTGGGACAGGGC

TACTGGGGCCAAGGCACACTAGTCACAGTCTCCTCAGCCTCCACCAAGGGCCCATCGGTCTTCCCCCTGGCA

CCCTCCTCCAAGAGCACCTCTGGGGGCACAGCGGCCCTGGGCTGCCTGGTCAAGGACTACTTCCCCGAACCG

GTGACGGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCTGCAAC

GTGAATCACAAGCCCAGCAACACCAAGGTGGACAAGAAAGTTGAGCCCAAATCTTGTGACAAAACTCACACA

TGCCCACCGTGCCCAGCACCTGAACTCGCGGGGGCACCGTCAGTCTTCCTCTTCCCCCCAAAACCCAAGGAC

ACCCTCATGATCTCCCGGACCCCTGAGGTCACATGCGTGGTGGTGGACGTGAGCCACGAAGACCCTGAGGTC

AAGTTCAACTGGTACGTGGACGGCGTGGAGGTGCATAATGCCAAGACAAAGCCGCGGGAGGAGCAGTACAAC

AGCACGTACCGTGTGGTCAGCGTCCTCACCGTCCTGCACCAGGACTGGCTGAATGGCAAGGAGTACAAGTGC

AAGGTCTCCAACAAAGCCCTCCCAGCCCCCATCGAGAAAACCATCTCCAAAGCCAAAGGGCAGCCCCGAGAA

CCACAGGTGTACACCCTGCCCCCATCCCGGGATGAGCTGACCAAGAACCAGGTCAGCCTGACCTGCCTGGTC

AAAGGCTTCTATCCCAGCGACATCGCCGTGGAGTGGGAGAGCAATGGGCAGCCGGAGAACAACTACAAGACC

ACGCCTCCCGTGCTGGACTCCGACGGCTCCTTCTTCCTCTACAGCAAGCTCACCGTGGACAAGAGCAGGTGG

CAGCAGGGGAACGTCTTCTCATGCTCCGTGATGCATGAGGCTCTGCACAACCACTACACGCAGAAGAGCCTC

TCCCTGTCTCCGGGTAAATGA

SEQ ID NO. 22: PN encoding Chimeric light chain Lc SEQ ID: 10
ATGAGGTGCTCTCTTCAGTTTCTGGGGGTGCTTATGTTCTGGATCTCTGGAGTCAGTGGGGATATTGTGATA

ACCCAGGATGAACTCTCCAATCCTGTCACTTCTGGAGAATCAGTTTCCATCTCCTGCAGGTCTAGTAAGAGT

CTCCTATATAAGGATGGGAAGACATACTTGAATTGGTTTCTGCAGAGACCAGGACAATCCCTCAGCTCCTG

ATCTATTTGATGTCCACCCGTGCATCAGGAGTCTCAGACCGGTTTAGTGGCAGTGGGTCAGGAACAGATTTC

ACCCTGGAAATCAGTAGAGTGAAGGCTGAGGATGTGGGTGTGTATTACTGTCAACAACTTGTAGAGTATCCG

CTCACGTTCGGTGCTGGGACCAAGCTGGAGCTGAAACGTACGGTGGCTGCACCATCTGTCTTCATCTTCCCG

CCATCTGATGAGCAGTTGAAATCTGGAACTGCCTCTGTTGTGTGCCTGCTGAATAACTTCTATCCCAGAGAG

GCCAAAGTACAGTGGAAGGTGGACAACGCCCTCCAATCGGGTAACTCCCAGGAGAGTGTCACAGAGCAGGAC

AGCAAGGACAGCACCTACAGCCTCAGCAGCACCCTGACGCTGAGCAAAGCAGACTACGAGAAACACAAAGTC

TACGCCTGCGAAGTCACCCATCAGGGCCTGAGCTCGCCCGTCACAAAGAGCTTCAACAGGGGAGAGTGTTAG

SEQ ID NO. 23: PN encoding 2A10 VH humanised construct H6 SEQ ID: 11
CAGGTGCAGCTGGTGCAGTCTGGGGCTGAGGTGAAGAAGCCTGGGGCCTCAGTGAAGGTTTCCTGCAAGGCA

TCTGGATACACCTTCACCAGCTACTGGATGCACTGGGTGCGACAGGCCCCTGGACAAGGGCTTGAGTGGATC

GGAAATATTAATCCTAGCAATGGTGGTACTAACTACAATGAGAAGTTCAAGAGCAGAGCCACCATGACCAGG

GACACGTCCACGAGCACAGCCTACATGGAGCTGAGCAGCCTGAGATCTGAGGACACGGCCGTGTATTACTGT

GAACTGGGACAGGGCTACTGGGGCCAGGGAACACTAGTCACAGTCTCCTCA

SEQ ID NO. 24: PN encoding 2A10 VH humanised construct H16 SEQ ID: 12
CAGGTGCAGCTGGTGCAGTCTGGGGCTGAGGTGAAGAAGCCTGGGGCCTCAGTGAAGGTTTCCTGCAAGGCA

TCTGGATACACCTTCACCAGCTACTGGATGCACTGGGTGAAACAGCGACCTGGACAAGGGCTTGAGTGGATC

GGAAATATTAATCCTAGCAATGGTGGTACTAACTACAATGAGAAGTTCAAGAGCAAAGCCACCCTCACCGTC

GACAAATCCACGAGCACAGCCTACATGGAGCTGAGCAGCCTGAGATCTGAGGACACGGCCGTGTATTACTGT

GAACTGGGACAGGGCTACTGGGGCCAGGGAACACTAGTCACAGTCTCCTCA

SEQ ID NO. 25: PN encoding 2A10 VL humanised construct L13 SEQ ID: 13
GATATTGTGATGACCCAGTCTCCACTCTCCCTGCCCGTCACCCTTGGACAGCCGGCCTCCATCTCCTGCAGG

TCTAGTAAGAGTCTCCTATATAAGGATGGGAAGACATACTTGAATTGGTTTCAGCAGAGGCCAGGCCAATCT

CCACAGCTCCTAATTTATTTGATGTCCACCCGTGCATCTGGGGTCCCAGACAGATTCAGCGGCGGTGGGTCA

GGCACTGATTTCACACTGAAAATCAGCAGGGTGGAGGCTGAGGATGTTGGGGTTTATTACTGCCAACAACTT

GTAGAGTATCCGCTCACGTTTGGCCAGGGGACCAAGCTGGAGATCAAA

SEQ ID NO. 26: PN encoding 2A10 VL humanised construct L16 SEQ ID: 14
GATATTGTGATGACCCAGTCTCCACTCTCCAACCCCGTCACCCTTGGACAGCCGGTCTCCATCTCCTGCAGG

TCTAGTAAGAGTCTCCTATATAAGGATGGGAAGACATACTTGAATTGGTTTCTCCAGAGGCCAGGCCAATCT

-continued

CCACAGCTCCTAATTTATTTGATGTCCACCCGTGCATCTGGGGTCCCAGACAGATTCAGCGGCGGTGGGTCA

GGCACTGATTTCACACTGAAAATCAGCAGGGTGGAGGCTGAGGATGTTGGGGTTTATTACTGCCAACAACTT

GTAGAGTATCCGCTCACGTTTGGCCAGGGGACCAAGCTGGAGATCAAA

SEQ ID NO. 27: PN encoding 2A10 heavy chain humanised construct H6 SEQ
ID: 15
ATGGGATGGAGCTGTATCATCCTCTTCTTGGTAGCAACAGCTACAGGTGTCCACTCCCAGGTGCAGCTGGTG

CAGTCTGGGGCTGAGGTGAAGAAGCCTGGGGCCTCAGTGAAGGTTTCCTGCAAGGCATCTGGATACACCTTC

ACCAGCTACTGGATGCACTGGGTGCGACAGGCCCCTGGACAAGGGCTTGAGTGGATCGGAAATATTAATCCT

AGCAATGGTGGTACTAACTACAATGAGAAGTTCAAGAGCAGAGCCACCATGACCAGGGACACGTCCACGAGC

ACAGCCTACATGGAGCTGAGCAGCCTGAGATCTGAGGACACGGCCGTGTATTACTGTGAACTGGGACAGGGC

TACTGGGGCCAGGGAACACTAGTCACAGTCTCCTCAGCCTCCACCAAGGGCCCATCGGTCTTCCCCCTGGCA

CCCTCCTCCAAGAGCACCTCTGGGGGCACAGCGGCCCTGGGCTGCCTGGTCAAGGACTACTTCCCCGAACCG

GTGACGGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCTGCAAC

GTGAATCACAAGCCCAGCAACACCAAGGTGGACAAGAAAGTTGAGCCCAAATCTTGTGACAAAACTCACACA

TGCCCACCGTGCCCAGCACCTGAACTCGCGGGGGCACCGTCAGTCTTCCTCTTCCCCCCAAAACCCAAGGAC

ACCCTCATGATCTCCCGGACCCCTGAGGTCACATGCGTGGTGGTGGACGTGAGCCACGAAGACCCTGAGGTC

AAGTTCAACTGGTACGTGGACGGCGTGGAGGTGCATAATGCCAAGACAAAGCCGCGGGAGGAGCAGTACAAC

AGCACGTACCGTGTGGTCAGCGTCCTCACCGTCCTGCACCAGGACTGGCTGAATGGCAAGGAGTACAAGTGC

AAGGTCTCCAACAAAGCCCTCCCAGCCCCCATCGAGAAAACCATCTCCAAAGCCAAAGGGCAGCCCCGAGAA

CCACAGGTGTACACCCTGCCCCCATCCCGGGATGAGCTGACCAAGAACCAGGTCAGCCTGACCTGCCTGGTC

AAAGGCTTCTATCCCAGCGACATCGCCGTGGAGTGGGAGAGCAATGGGCAGCCGGAGAACAACTACAAGACC

ACGCCTCCCGTGCTGGACTCCGACGGCTCCTTCTTCCTCTACAGCAAGCTCACCGTGGACAAGAGCAGGTGG

CAGCAGGGGAACGTCTTCTCATGCTCCGTGATGCATGAGGCTCTGCACAACCACTACACGCAGAAGAGCCTC

TCCCTGTCTCCGGGTAAATGA

SEQ ID NO. 28: PN encoding 2A10 heavy chain humanised construct H16 SEQ
ID: 16
ATGGGATGGAGCTGTATCATCCTCTTCTTGGTAGCAACAGCTACAGGTGTCCACTCCCAGGTGCAGCTGGTG

CAGTCTGGGGCTGAGGTGAAGAAGCCTGGGGCCTCAGTGAAGGTTTCCTGCAAGGCATCTGGATACACCTTC

ACCAGCTACTGGATGCACTGGGTGAAACAGCGACCTGGACAAGGGCTTGAGTGGATCGGAAATATTAATCCT

AGCAATGGTGGTACTAACTACAATGAGAAGTTCAAGAGCAAAGCCACCCTCACCGTCGACAAATCCACGAGC

ACAGCCTACATGGAGCTGAGCAGCCTGAGATCTGAGGACACGGCCGTGTATTACTGTGAACTGGGACAGGGC

TACTGGGGCCAGGGAACACTAGTCACAGTCTCCTCAGCCTCCACCAAGGGCCCATCGGTCTTCCCCCTGGCA

CCCTCCTCCAAGAGCACCTCTGGGGGCACAGCGGCCCTGGGCTGCCTGGTCAAGGACTACTTCCCCGAACCG

GTGACGGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCTGCAAC

GTGAATCACAAGCCCAGCAACACCAAGGTGGACAAGAAAGTTGAGCCCAAATCTTGTGACAAAACTCACACA

TGCCCACCGTGCCCAGCACCTGAACTCGCGGGGGCACCGTCAGTCTTCCTCTTCCCCCCAAAACCCAAGGAC

ACCCTCATGATCTCCCGGACCCCTGAGGTCACATGCGTGGTGGTGGACGTGAGCCACGAAGACCCTGAGGTC

AAGTTCAACTGGTACGTGGACGGCGTGGAGGTGCATAATGCCAAGACAAAGCCGCGGGAGGAGCAGTACAAC

AGCACGTACCGTGTGGTCAGCGTCCTCACCGTCCTGCACCAGGACTGGCTGAATGGCAAGGAGTACAAGTGC

AAGGTCTCCAACAAAGCCCTCCCAGCCCCCATCGAGAAAACCATCTCCAAAGCCAAAGGGCAGCCCCGAGAA

CCACAGGTGTACACCCTGCCCCCATCCCGGGATGAGCTGACCAAGAACCAGGTCAGCCTGACCTGCCTGGTC

-continued

AAAGGCTTCTATCCCAGCGACATCGCCGTGGAGTGGGAGAGCAATGGGCAGCCGGAGAACAACTACAAGACC

ACGCCTCCCGTGCTGGACTCCGACGGCTCCTTCTTCCTCTACAGCAAGCTCACCGTGGACAAGAGCAGGTGG

CAGCAGGGGAACGTCTTCTCATGCTCCGTGATGCATGAGGCTCTGCACAACCACTACACGCAGAAGAGCCTC

TCCCTGTCTCCGGGTAAATGA

SEQ ID NO. 29: PN encoding 2A10 light chain humanised construct L13 SEQ ID: 17
ATGGGATGGAGCTGTATCATCCTCTTCTTGGTAGCAACAGCTACAGGTGTCCACTCCGATATTGTGATGACC

CAGTCTCCACTCTCCCTGCCCGTCACCCTTGGACAGCCGGCCTCCATCTCCTGCAGGTCTAGTAAGAGTCTC

CTATATAAGGATGGAAGACATACTTGAATTGGTTTCAGCAGAGGCCAGGCCAATCTCCACAGCTCCTAATT

TATTTGATGTCCACCCGTGCATCTGGGGTCCCAGACAGATTCAGCGGCGGTGGGTCAGGCACTGATTTCACA

CTGAAAATCAGCAGGGTGGAGGCTGAGGATGTTGGGGTTTATTACTGCCAACAACTTGTAGAGTATCCGCTC

ACGTTTGGCCAGGGGACCAAGCTGGAGATCAAACGTACGGTGGCTGCACCATCTGTCTTCATCTTCCCGCCA

TCTGATGAGCAGTTGAAATCTGGAACTGCCTCTGTTGTGTGCCTGCTGAATAACTTCTATCCCAGAGAGGCC

AAAGTACAGTGGAAGGTGGACAACGCCCTCCAATCGGGTAACTCCCAGGAGAGTGTCACAGAGCAGGACAGC

AAGGACAGCACCTACGCCTCAGCAGCACCCTGACGCTGAGCAAAGCAGACTACGAGAAACACAAAGTCTAC

GCCTGCGAAGTCACCCATCAGGGCCTGAGCTCGCCCGTCACAAAGAGCTTCAACAGGGGAGAGTGTTAG

SEQ ID NO. 30: PN encoding 2A10 light chain humanised construct L16 SEQ ID: 18
ATGGGATGGAGCTGTATCATCCTCTTCTTGGTAGCAACAGCTACAGGTGTCCACTCCGATATTGTGATGACC

CAGTCTCCACTCTCCAACCCCGTCACCCTTGGACAGCCGGTCTCCATCTCCTGCAGGTCTAGTAAGAGTCTC

CTATATAAGGATGGAAGACATACTTGAATTGGTTTCTCCAGAGGCCAGGCCAATCTCCACAGCTCCTAATT

TATTTGATGTCCACCCGTGCATCTGGGGTCCCAGACAGATTCAGCGGCGGTGGGTCAGGCACTGATTTCACA

CTGAAAATCAGCAGGGTGGAGGCTGAGGATGTTGGGGTTTATTACTGCCAACAACTTGTAGAGTATCCGCTC

ACGTTTGGCCAGGGGACCAAGCTGGAGATCAAACGTACGGTGGCTGCACCATCTGTCTTCATCTTCCCGCCA

TCTGATGAGCAGTTGAAATCTGGAACTGCCTCTGTTGTGTGCCTGCTGAATAACTTCTATCCCAGAGAGGCC

AAAGTACAGTGGAAGGTGGACAACGCCCTCCAATCGGGTAACTCCCAGGAGAGTGTCACAGAGCAGGACAGC

AAGGACAGCACCTACAGCCTCAGCAGCACCCTGACGCTGAGCAAAGCAGACTACGAGAAACACAAAGTCTAC

GCCTGCGAAGTCACCCATCAGGGCCTGAGCTCGCCCGTCACAAAGAGCTTCAACAGGGGAGAGTGTTAG

SEQ ID NO. 31: Campath leader sequence
MGWSCIILFLVATATGVHS

SEQ ID NO. 32: Amino acids 586-785 of human NOGO A (NOGO-A56)fused to GST
MSPILGYWKIKGLVQPTRLLLEYLEEKYEEHLYERDEGDKWRNKKFELGLEFPNLPYYIDGDVKLTQSMAII

RYIADKHNMLGGCPKERAEISMLEGAVLDIRYGVSRIAYSKDFETLKVDFLSKLPEMLKMFEDRLCHKTYLN

GDHVTHPDFMLYDALDVVLYMDPMCLDAFPKLVCFKKRIEAIPQIDKYLKSSKYIAWPLQGWQATFGGGDHP

PKSDLEVLFQGPLGSMQESLYPAAQLCPSFEESEATPSPVLPDIVMEAPLNSAVPSAGASVIQPSSSPLEAS

SVNYESIKHEPENPPPYEEAMSVSLKKVSGIKEEIKEPENINAALQETEAPYISIACDLIKETKLSAEPAPD

FSDYSEMAKVEQPVPDHSELVEDSSPDSEPVDLFSDDSIPDVPQKQDETVMLVKESLTETSFESMIEYENKE

LERPHRD

SEQ ID NO. 33: 2A10 VH humanised construct H1
QVQLVQSGAEVKKPGASVKVSCKASGYTFTSYWMHWVRQAPGQGLEWMGNINPSNGGTNYNEKFKSRVTMTR

DTSTSTVYMELSSLRSEDTAVYYCELGQGYWGQGTLVTVSS

SEQ ID NO. 34: 2A10 VL humanised construct L11
DIVITQSPLSLPVTLGQPASISCRSSKSLLYKDGKTYLNWFQQRPGQSPQLLIYLMSTRASGVPDRFSGGGS

GTDFTLKISRVEAEDVGVYYCQQLVEYPLTFGQGTKLEIK

SEQ ID NO. 35: 2A10 heavy chain humanised construct H1
MGWSCIILFLVATATGVHSQVQLVQSGAEVKKPGASVKVSCKASGYTFTSYWMHWVRQAPGQGLEWMGNINP

SNGGTNYNEKFKSRVTMTRDTSTSTVYMELSSLRSEDTAVYYCELGQGYWGQGTLVTVSSASTKGPSVFPLA

PSSKSTSGGTAALGCLVKDYFPEPVTVSWNSGALTSGVHTFPAVLQSSGLYSLSSVVTVPSSSLGTQTYICN

VNHKPSNTKVDKKVEPKSCDKTHTCPPCPAPELAGAPSVFLFPPKPKDTLMISRTPEVTCVVVDVSHEDPEV

KFNWYVDGVEVHNAKTKPREEQYNSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTTPPVLDSDGSFFLYSKLTVDKSRW

QQGNVFSCSVMHEALHNHYTQKSLSLSPGK

SEQ ID NO. 36: 2A10 light chain humanised construct L11
MGWSCIILFLVATATGVHSDIVITQSPLSLPVTLGQPASISCRSSKSLLYKDGKTYLNWFQQRPGQSPQLLI

YLMSTRASGVPDRFSGGGSGTDFTLKISRVEAEDVGVYYCQQLVEYPLTFGQGTKLEIKRTVAAPSVFIFPP

SDEQLKSGTASVVCLLNNFYPREAKVQWKVDNALQSGNSQESVTEQDSKDSTYSLSSTLTLSKADYEKHKVY

ACEVTHQGLSSPVTKSFNRGEC

SEQ ID NO. 37: PN encoding 2A10 VH humanised construct H1 SEQ ID: 33
CAGGTGCAGCTGGTGCAGTCTGGGGCTGAGGTGAAGAAGCCTGGGGCCTCAGTGAAGGTTTCCTGCAAGGCA

TCTGGATACACCTTCACCAGCTACTGGATGCACTGGGTGCGACAGGCCCCTGGACAAGGGCTTGAGTGGATG

GGAAATATTAATCCTAGCAATGGTGGTACTAACTACAATGAGAAGTTCAAGAGCAGAGTCACCATGACCAGG

GACACGTCCACGAGCACAGTCTACATGGAGCTGAGCAGCCTGAGATCTGAGGACACGGCCGTGTATTACTGT

GAACTGGGACAGGGCTACTGGGGCCAGGGAACACTAGTCACAGTCTCCTCA

SEQ ID NO. 38: PN encoding 2A10 VL humanised construct L11 SEQ ID: 34
GATATTGTGATAACCCAGTCTCCACTCTCCCTGCCCGTCACCCTTGGACAGCCGGCCTCCATCTCCTGCAGG

TCTAGTAAGAGTCTCCTATATAAGGATGGGAAGACATACTTGAATTGGTTTCAGCAGAGGCCAGGCCAATCT

CCACAGCTCCTAATTTATTTGATGTCCACCCGTGCATCTGGGGTCCCAGACAGATTCAGCGGCGGTGGGTCA

GGCACTGATTTCACACTGAAAATCAGCAGGGTGGAGGCTGAGGATGTTGGGGTTTATTACTGCCAACAACTT

GTAGAGTATCCGCTCACGTTTGGCCAGGGGACCAAGCTGGAGATCAAA

SEQ ID NO. 39: PN encoding 2A10 humanised heavy chain H1 SEQ ID: 35
ATGGGATGGAGCTGTATCATCCTCTTCTTGGTAGCAACAGCTACAGGTGTCCACTCCCAGGTGCAGCTGGTG

CAGTCTGGGGCTGAGGTGAAGAAGCCTGGGGCCTCAGTGAAGGTTTCCTGCAAGGCATCTGGATACACCTTC

ACCAGCTACTGGATGCACTGGGTGCGACAGGCCCCTGGACAAGGGCTTGAGTGGATGGGAAATATTAATCCT

AGCAATGGTGGTACTAACTACAATGAGAAGTTCAAGAGCAGAGTCACCATGACCAGGGACACGTCCACGAGC

ACAGTCTACATGGAGCTGAGCAGCCTGAGATCTGAGGACACGGCCGTGTATTACTGTGAACTGGGACAGGGC

TACTGGGGCCAGGGAACACTAGTCACAGTCTCCTCAGCCTCCACCAAGGGCCCATCGGTCTTCCCCCTGGCA

CCCTCCTCCAAGAGCACCTCTGGGGGCACAGCGGCCCTGGGCTGCCTGGTCAAGGACTACTTCCCCGAACCG

GTGACGGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCTGCAAC

GTGAATCACAAGCCCAGCAACACCAAGGTGGACAAGAAAGTTGAGCCCAAATCTTGTGACAAAACTCACACA

TGCCCACCGTGCCCAGCACCTGAACTCGCGGGGGCACCGTCAGTCTTCCTCTTCCCCCCAAAACCCAAGGAC

ACCCTCATGATCTCCCGGACCCCTGAGGTCACATGCGTGGTGGTGGACGTGAGCCACGAAGACCCTGAGGTC

AAGTTCAACTGGTACGTGGACGGCGTGGAGGTGCATAATGCCAAGACAAAGCCGCGGGAGGAGCAGTACAAC

AGCACGTACCGTGTGGTCAGCGTCCTCACCGTCCTGCACCAGGACTGGCTGAATGGCAAGGAGTACAAGTGC

AAGGTCTCCAACAAAGCCCTCCCAGCCCCCATCGAGAAAACCATCTCCAAAGCCAAAGGGCAGCCCCGAGAA

CCACAGGTGTACACCCTGCCCCCATCCCGGGATGAGCTGACCAAGAACCAGGTCAGCCTGACCTGCCTGGTC

AAAGGCTTCTATCCCAGCGACATCGCCGTGGAGTGGGAGAGCAATGGGCAGCCGGAGAACAACTACAAGACC

-continued

ACGCCTCCCGTGCTGGACTCCGACGGCTCCTTCTTCCTCTACAGCAAGCTCACCGTGGACAAGAGCAGGTGG

CAGCAGGGGAACGTCTTCTCATGCTCCGTGATGCATGAGGCTCTGCACAACCACTACACGCAGAAGAGCCTC

TCCCTGTCTCCGGGTAAATGA

SEQ ID NO. 40: PN encoding 2A10 humanised light chain construct L11 SEQ
ID: 36
ATGGGATGGAGCTGTATCATCCTCTTCTTGGTAGCAACAGCTACAGGTGTCCACTCCGATATTGTGATAACC

CAGTCTCCACTCTCCCTGCCCGTCACCCTTGGACAGCCGGCCTCCATCTCCTGCAGGTCTAGTAAGAGTCTC

CTATATAAGGATGGGAAGACATACTTGAATTGGTTTCAGCAGAGGCCAGGCCAATCTCCACAGCTCCTAATT

TATTTGATGTCCACCCGTGCATCTGGGGTCCCAGACAGATTCAGCGGCGGTGGGTCAGGCACTGATTTCACA

CTGAAAATCAGCAGGGTGGAGGCTGAGGATGTTGGGGTTTATTACTGCCAACAACTTGTAGAGTATCCGCTC

ACGTTTGGCCAGGGGACCAAGCTGGAGATCAAACGTACGGTGGCTGCACCATCTGTCTTCATCTTCCCGCCA

TCTGATGAGCAGTTGAAATCTGGAACTGCCTCTGTTGTGTGCCTGCTGAATAACTTCTATCCCAGAGAGGCC

AAAGTACAGTGGAAGGTGGACAACGCCCTCCAATCGGGTAACTCCCAGGAGAGTGTCACAGAGCAGGACAGC

AAGGACAGCACCTACAGCCTCAGCAGCACCCTGACGCTGAGCAAAGCAGACTACGAGAAACACAAAGTCTAC

GCCTGCGAAGTCACCCATCAGGGCCTGAGCTCGCCCGTCACAAAGAGCTTCAACAGGGGAGAGTGTTAG

SEQ ID NO. 41: 2A10 VH humanised construct H20
QVQLVQSGAEVKKPGASVKVSCKASGYTFTSYWMHWVRQAPGQGLEWIGNINPSNGGTNYNEKFKSKATMTR

DTSTSTAYMELSSLRSEDTAVYYCELGQGYWGQGTLVTVSS

SEQ ID NO. 42: 2A10 heavy chain humanised construct H20
MGWSCIILFLVATATGVHSQVQLVQSGAEVKKPGASVKVSCKASGYTFTSYWMHWVRQAPGQGLEWIGNINP

SNGGTNYNEKFKSKATMTRDTSTSTAYMELSSLRSEDTAVYYCELGQGYWGQGTLVTVSSASTKGPSVFPLA

PSSKSTSGGTAALGCLVKDYFPEPVTVSWNSGALTSGVHTFPAVLQSSGLYSLSSVVTVPSSSLGTQTYICN

VNHKPSNTKVDKKVEPKSCDKTHTCPPCPAPELAGAPSVFLFPPKPKDTLMISRTPEVTCVVVDVSHEDPEV

KFNWYVDGVEVHNAKTKPREEQYNSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTTPPVLDSDGSFFLYSKLTVDKSRW

QQGNVFSCSVMHEALHNHYTQKSLSLSPGK

SEQ ID NO. 43: PN encoding 2A10 VH humanised construct H20 SEQ ID: 41
CAGGTGCAGCTGGTGCAGTCTGGGGCTGAGGTGAAGAAGCCTGGGGCCTCAGTGAAGGTTTCCTGCAAGGCA

TCTGGATACACCTTCACCAGCTACTGGATGCACTGGGTGCGACAGGCCCCTGGACAAGGGCTTGAGTGGATC

GGAAATATTAATCCTAGCAATGGTGGTACTAACTACAATGAGAAGTTCAAGAGCAAGGCCACCATGACCAGG

GACACGTCCACGAGCACAGCCTACATGGAGCTGAGCAGCCTGAGATCTGAGGACACGGCCGTGTATTACTGT

GAACTGGGACAGGGCTACTGGGGCCAGGGAACACTAGTCACAGTCTCCTCA

SEQ ID NO. 44: PN encoding 2A10 heavy chain humanised construct H20 SEQ
ID: 42
ATGGGATGGAGCTGTATCATCCTCTTCTTGGTAGCAACAGCTACAGGTGTCCACTCCCAGGTGCAGCTGGTG

CAGTCTGGGGCTGAGGTGAAGAAGCCTGGGGCCTCAGTGAAGGTTTCCTGCAAGGCATCTGGATACACCTTC

ACCAGCTACTGGATGCACTGGGTGCGACAGGCCCCTGGACAAGGGCTTGAGTGGATCGGAAATATTAATCCT

AGCAATGGTGGTACTAACTACAATGAGAAGTTCAAGAGCAAGGCCACCATGACCAGGGACACGTCCACGAGC

ACAGCCTACATGGAGCTGAGCAGCCTGAGATCTGAGGACACGGCCGTGTATTACTGTGAACTGGGACAGGGC

TACTGGGGCCAGGGAACACTAGTCACAGTCTCCTCAGCCTCCACCAAGGGCCCATCGGTCTTCCCCCTGGCA

CCCTCCTCCAAGAGCACCTCTGGGGGCACAGCGGCCCTGGGCTGCCTGGTCAAGGACTACTTCCCCGAACCG

GTGACGGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCTGCAAC

GTGAATCACAAGCCCAGCAACACCAAGGTGGACAAGAAAGTTGAGCCCAAATCTTGTGACAAAACTCACACA

```
TGCCCACCGTGCCCAGCACCTGAACTCGCGGGGGCACCGTCAGTCTTCCTCTTCCCCCCAAAACCCAAGGAC

ACCCTCATGATCTCCCGGACCCCTGAGGTCACATGCGTGGTGGTGGACGTGAGCCACGAAGACCCTGAGGTC

AAGTTCAACTGGTACGTGGACGGCGTGGAGGTGCATAATGCCAAGACAAAGCCGCGGGAGGAGCAGTACAAC

AGCACGTACCGTGTGGTCAGCGTCCTCACCGTCCTGCACCAGGACTGGCTGAATGGCAAGGAGTACAAGTGC

AAGGTCTCCAACAAAGCCCTCCCAGCCCCCATCGAGAAAACCATCTCCAAAGCCAAAGGGCAGCCCCGAGAA

CCACAGGTGTACACCCTGCCCCCATCCCGGGATGAGCTGACCAAGAACCAGGTCAGCCTGACCTGCCTGGTC

AAAGGCTTCTATCCCAGCGACATCGCCGTGGAGTGGGAGAGCAATGGGCAGCCGGAGAACAACTACAAGACC

ACGCCTCCCGTGCTGGACTCCGACGGCTCCTTCTTCCTCTACAGCAAGCTCACCGTGGACAAGAGCAGGTGG

CAGCAGGGGAACGTCTTCTCATGCTCCGTGATGCATGAGGCTCTGCACAACCACTACACGCAGAAGAGCCTC

TCCCTGTCTCCGGGTAAATGA

SEQ ID NO. 45: 2A10 CDR-H3 (G95M)
MQGY

SEQ ID NO. 46: Amino acid sequence of Marmoset NOGO-A fragment
VQDSLCPVAQLCPSFEESEATPSPVLPDIVMEAPLNSAVPSAGASAVQPSSSPLEASSVNFESVKHEPENPP

PYEEAMNVSRKKVSGIKEEIKEPESINAAVQETEAPYISIACDLIKETKLSAEPTPDFSSYSEMAKVEQPLP

DHSELVEDSSPDSEPVDLFSDDSIPDVPQKQDEAVILVKETLTETSFESMIEHENK

SEQ ID NO. 47: VH humanised construct H26
QVQLVQSGAEVKKPGASVKVSCKASGYTFTSYWMHWVRQAPGQGLEWIGNINPSNGGTNYNEKFKSRATMTR

DTSTSTAYMELSSLRSEDTAVYYCELMQGYWGQGTLVTVSS

SEQ ID NO. 48: VH humanised construct H27
QVQLVQSGAEVKKPGASVKVSCKASGYTFTSYWMHWVKQRPGQGLEWIGNINPSNGGTNYNEKFKSKATLTV

DKSTSTAYMELSSLRSEDTAVYYCELMQGYWGQGTLVTVSS

SEQ ID NO. 49: VH humanised construct H28
QVQLVQSGAEVKKPGASVKVSCKASGYTFTSYWMHWVRQAPGQGLEWIGNINPSNGGTNYNEKFKSKATMTR

DTSTSTAYMELSSLRSEDTAVYYCELMQGYWGQGTLVTVSS

SEQ ID NO. 50: PN encoding VH humanised construct H26 SEQ ID: 47
CAGGTGCAGCTGGTGCAGTCTGGGGCTGAGGTGAAGAAGCCTGGGGCCTCAGTGAAGGTTTCCTGCAAGGCA

TCTGGATACACCTTCACCAGCTACTGGATGCACTGGGTGCGACAGGCCCCTGGACAAGGGCTTGAGTGGATC

GGAAATATTAATCCTAGCAATGGTGGTACTAACTACAATGAGAAGTTCAAGAGCAGAGCCACCATGACCAGG

GACACGTCCACGAGCACAGCCTACATGGAGCTGAGCAGCCTGAGATCTGAGGACACGGCCGTGTATTACTGT

GAACTGATGCAGGGCTACTGGGGCCAGGGAACACTAGTCACAGTCTCCTCA

SEQ ID NO. 51: PN encoding VH humanised construct H27 SEQ ID: 48
CAGGTGCAGCTGGTGCAGTCTGGGGCTGAGGTGAAGAAGCCTGGGGCCTCAGTGAAGGTTTCCTGCAAGGCA

TCTGGATACACCTTCACCAGCTACTGGATGCACTGGGTGAAACAGCGACCTGGACAAGGGCTTGAGTGGATC

GGAAATATTAATCCTAGCAATGGTGGTACTAACTACAATGAGAAGTTCAAGAGCAAAGCCACCCTCACCGTC

GACAAATCCACGAGCACAGCCTACATGGAGCTGAGCAGCCTGAGATCTGAGGACACGGCCGTGTATTACTGT

GAACTGATGCAGGGCTACTGGGGCCAGGGAACACTAGTCACAGTCTCCTCA

SEQ ID NO. 52: PN encoding VH humanised construct H28 SEQ ID: 49
CAGGTGCAGCTGGTGCAGTCTGGGGCTGAGGTGAAGAAGCCTGGGGCCTCAGTGAAGGTTTCCTGCAAGGCA

TCTGGATACACCTTCACCAGCTACTGGATGCACTGGGTGCGACAGGCCCCTGGACAAGGGCTTGAGTGGATC

GGAAATATTAATCCTAGCAATGGTGGTACTAACTACAATGAGAAGTTCAAGAGCAAGGCCACCATGACCAGG

GACACGTCCACGAGCACAGCCTACATGGAGCTGAGCAGCCTGAGATCTGAGGACACGGCCGTGTATTACTGT

GAACTGATGCAGGGCTACTGGGGCCAGGGAACACTAGTCACAGTCTCCTCA
```

-continued

SEQ ID NO. 53: Heavy chain humanised construct H26
MGWSCIILFLVATATGVHSQVQLVQSGAEVKKPGASVKVSCKASGYTFTSYWMHWVRQAPGQGLEWIGNINP

SNGGTNYNEKFKSRATMTRDTSTSTAYMELSSLRSEDTAVYYCELMQGYWGQGTLVTVSSASTKGPSVFPLA

PSSKSTSGGTAALGCLVKDYFPEPVTVSWNSGALTSGVHTFPAVLQSSGLYSLSSVVTVPSSSLGTQTYICN

VNHKPSNTKVDKKVEPKSCDKTHTCPPCPAPELAGAPSVFLFPPKPKDTLMISRTPEVTCVVVDVSHEDPEV

KFNWYVDGVEVHNAKTKPREEQYNSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTTPPVLDSDGSFFLYSKLTVDKSRW

QQGNVFSCSVMHEALHNHYTQKSLSLSPGK.

SEQ ID NO. 54: Heavy chain humanised construct H27
MGWSCIILFLVATATGVHSQVQLVQSGAEVKKPGASVKVSCKASGYTFTSYWMHWVKQRPGQGLEWIGNINP

SNGGTNYNEKFKSKATLTVDKSTSTAYMELSSLRSEDTAVYYCELMQGYWGQGTLVTVSSASTKGPSVFPLA

PSSKSTSGGTAALGCLVKDYFPEPVTVSWNSGALTSGVHTFPAVLQSSGLYSLSSVVTVPSSSLGTQTYICN

VNHKPSNTKVDKKVEPKSCDKTHTCPPCPAPELAGAPSVFLFPPKPKDTLMISRTPEVTCVVVDVSHEDPEV

KFNWYVDGVEVHNAKTKPREEQYNSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTTPPVLDSDGSFFLYSKLTVDKSRW

QQGNVFSCSVMHEALHNHYTQKSLSLSPGK

SEQ ID NO. 55: Heavy chain humanised construct H28
MGWSCIILFLVATATGVHSQVQLVQSGAEVKKPGASVKVSCKASGYTFTSYWMHWVRQAPGQGLEWIGNINP

SNGGTNYNEKFKSKATMTRDTSTSTAYMELSSLRSEDTAVYYCELMQGYWGQGTLVTVSSASTKGPSVFPLA

PSSKSTSGGTAALGCLVKDYFPEPVTVSWNSGALTSGVHTFPAVLQSSGLYSLSSVVTVPSSSLGTQTYICN

VNHKPSNTKVDKKVEPKSCDKTHTCPPCPAPELAGAPSVFLFPPKPKDTLMISRTPEVTCVVVDVSHEDPEV

KFNWYVDGVEVHNAKTKPREEQYNSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTTPPVLDSDGSFFLYSKLTVDKSRW

QQGNVFSCSVMHEALHNHYTQKSLSLSPGK

SEQ ID NO. 56: PN encoding Heavy chain humanised construct H26 SEQ ID:
53
ATGGGATGGAGCTGTATCATCCTCTTCTTGGTAGCAACAGCTACAGGTGTCCACTCCCAGGTGCAGCTGGTG

CAGTCTGGGGCTGAGGTGAAGAAGCCTGGGGCCTCAGTGAAGGTTTCCTGCAAGGCATCTGGATACACCTTC

ACCAGCTACTGGATGCACTGGGTGCGACAGGCCCCTGGACAAGGGCTTGAGTGGATCCGAAATATTAATCCT

AGCAATGGTGGTACTAACTACAATGAGAAGTTCAAGAGCAGAGCCACCATGACCAGGGACACGTCCACGAGC

ACAGCCTACATGGAGCTGAGCAGCCTGAGATCTGAGGACACGGCCGTGTATTACTGTGAACTGATGCAGGGC

TACTGGGGCCAGGGAACACTAGTCACAGTCTCCTCAGCCTCCACCAAGGGCCCATCGGTCTTCCCCCTGGCA

CCCTCCTCCAAGAGCACCTCTGGGGGCACAGCGGCCCTGGGCTGCCTGGTCAAGGACTACTTCCCCGAACCG

GTGACGGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCTGCAAC

GTGAATCACAAGCCCAGCAACACCAAGGTGGACAAGAAAGTTGAGCCCAAATCTTGTGACAAAACTCACACA

TGCCCACCGTGCCCAGCACCTGAACTCGCGGGGGCACCGTCAGTCTTCCTCTTCCCCCCAAAACCCAAGGAC

ACCCTCATGATCTCCCGGACCCCTGAGGTCACATGCGTGGTGGTGGACGTGAGCCACGAAGACCCTGAGGTC

AAGTTCAACTGGTACGTGGACGGCGTGGAGGTGCATAATGCCAAGACAAAGCCGCGGGAGGAGCAGTACAAC

AGCACGTACCGTGTGGTCAGCGTCCTCACCGTCCTGCACCAGGACTGGCTGAATGGCAAGGAGTACAAGTGC

AAGGTCTCCAACAAAGCCCTCCCAGCCCCCATCGAGAAAACCATCTCCAAAGCCAAAGGGCAGCCCCGAGAA

CCACAGGTGTACACCCTGCCCCCATCCCGGGATGAGCTGACCAAGAACCAGGTCAGCCTGACCTGCCTGGTC

AAAGGCTTCTATCCCAGCGACATCGCCGTGGAGTGGGAGAGCAATGGGCAGCCGGAGAACAACTACAAGACC

-continued

ACGCCTCCCGTGCTGGACTCCGACGGCTCCTTCTTCCTCTACAGCAAGCTCACCGTGGACAAGAGCAGGTGG

CAGCAGGGGAACGTCTTCTCATGCTCCGTGATGCATGAGGCTCTGCACAACCACTACACGCAGAAGAGCCTC

TCCCTGTCTCCGGGTAAATGA

SEQ ID NO. 57: PN encoding Heavy chain humanised construct H27 SEQ ID: 54

ATGGGATGGAGCTGTATCATCCTCTTCTTGGTAGCAACAGCTACAGGTGTCCACTCCCAGGTGCAGCTGGTG

CAGTCTGGGGCTGAGGTGAAGAAGCCTGGGGCCTCAGTGAAGGTTTCCTGCAAGGCATCTGGATACACCTTC

ACCAGCTACTGGATGCACTGGGTGAAACAGCGACCTGGACAAGGGCTTGAGTGGATCGGAAATATTAATCCT

AGCAATGGTGGTACTAACTACAATGAGAAGTTCAAGAGCAAAGCCACCCTCACCGTCGACAAATCCACGAGC

ACAGCCTACATGGAGCTGAGCAGCCTGAGATCTGAGGACACGGCCGTGTATTACTGTGAACTGATGCAGGGC

TACTGGGGCCAGGGAACACTAGTCACAGTCTCCTCAGCCTCCACCAAGGGCCCATCGGTCTTCCCCCTGGCA

CCCTCCTCCAAGAGCACCTCTGGGGGCACAGCGGCCCTGGGCTGCCTGGTCAAGGACTACTTCCCCGAACCG

GTGACGGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCTGCAAC

GTGAATCACAAGCCCAGCAACACCAAGGTGGACAAGAAAGTTGAGCCCAAATCTTGTGACAAAACTCACACA

TGCCCACCGTGCCCAGCACCTGAACTCGCGGGGGCACCGTCAGTCTTCCTCTTCCCCCCAAAACCCAAGGAC

ACCCTCATGATCTCCCGGACCCCTGAGGTCACATGCGTGGTGGTGGACGTGAGCCACGAAGACCCTGAGGTC

AAGTTCAACTGGTACGTGGACGGCGTGGAGGTGCATAATGCCAAGACAAAGCCGCGGGAGGAGCAGTACAAC

AGCACGTACCGTGTGGTCAGCGTCCTCACCGTCCTGCACCAGGACTGGCTGAATGGCAAGGAGTACAAGTGC

AAGGTCTCCAACAAAGCCCTCCCAGCCCCCATCGAGAAAACCATCTCCAAAGCCAAAGGGCAGCCCCGAGAA

CCACAGGTGTACACCCTGCCCCCATCCCGGGATGAGCTGACCAAGAACCAGGTCAGCCTGACCTGCCTGGTC

AAAGGCTTCTATCCCAGCGACATCGCCGTGGAGTGGGAGAGCAATGGGCAGCCGGAGAACAACTACAAGACC

ACGCCTCCCGTGCTGGACTCCGACGGCTCCTTCTTCCTCTACAGCAAGCTCACCGTGGACAAGAGCAGGTGG

CAGCAGGGGAACGTCTTCTCATGCTCCGTGATGCATGAGGCTCTGCACAACCACTACACGCAGAAGAGCCTC

TCCCTGTCTCCGGGTAAATGA

SEQ ID NO. 58: PN encoding Heavy chain humanised construct H28 SEQ ID: 55

ATGGGATGGAGCTGTATCATCCTCTTCTTGGTAGCAACAGCTACAGGTGTCCACTCCCAGGTGCAGCTGGTG

CAGTCTGGGGCTGAGGTGAAGAAGCCTGGGGCCTCAGTGAAGGTTTCCTGCAAGGCATCTGGATACACCTTC

ACCAGCTACTGGATGCACTGGGTGCGACAGGCCCCTGGACAAGGGCTTGAGTGGATCGGAAATATTAATCCT

AGCAATGGTGGTACTAACTACAATGAGAAGTTCAAGAGCAAGGCCACCATGACCAGGGACACGTCCACGAGC

ACAGCCTACATGGAGCTGAGCAGCCTGAGATCTGAGGACACGGCCGTGTATTACTGTGAACTGATGCAGGGC

TACTGGGGCCAGGGAACACTAGTCACAGTCTCCTCAGCCTCCACCAAGGGCCCATCGGTCTTCCCCCTGGCA

CCCTCCTCCAAGAGCACCTCTGGGGGCACAGCGGCCCTGGGCTGCCTGGTCAAGGACTACTTCCCCGAACCG

GTGACGGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCTGCAAC

GTGAATCACAAGCCCAGCAACACCAAGGTGGACAAGAAAGTTGAGCCCAAATCTTGTGACAAAACTCACACA

TGCCCACCGTGCCCAGCACCTGAACTCGCGGGGGCACCGTCAGTCTTCCTCTTCCCCCCAAAACCCAAGGAC

ACCCTCATGATCTCCCGGACCCCTGAGGTCACATGCGTGGTGGTGGACGTGAGCCACGAAGACCCTGAGGTC

AAGTTCAACTGGTACGTGGACGGCGTGGAGGTGCATAATGCCAAGACAAAGCCGCGGGAGGAGCAGTACAAC

AGCACGTACCGTGTGGTCAGCGTCCTCACCGTCCTGCACCAGGACTGGCTGAATGGCAAGGAGTACAAGTGC

AAGGTCTCCAACAAAGCCCTCCCAGCCCCCATCGAGAAAACCATCTCCAAAGCCAAAGGGCAGCCCCGAGAA

CCACAGGTGTACACCCTGCCCCCATCCCGGGATGAGCTGACCAAGAACCAGGTCAGCCTGACCTGCCTGGTC

```
AAAGGCTTCTATCCCAGCGACATCGCCGTGGAGTGGGAGAGCAATGGGCAGCCGGAGAACAACTACAAGACC

ACGCCTCCCGTGCTGGACTCCGACGGCTCCTTCTTCCTCTACAGCAAGCTCACCGTGGACAAGAGCAGGTGG

CAGCAGGGGAACGTCTTCTCATGCTCCGTGATGCATGAGGCTCTGCACAACCACTACACGCAGAAGAGCCTC

TCCCTGTCTCCGGGTAAATGA

SEQ ID NO. 59: Heavy chain Hc (G95M)
MGWSCIILFLVAAATGVHSQVQLQQPGTELVKPGASVKLSCKASGYTFTSYWMHWVKQRPGQGLEWIGNINP

SNGGTNYNEKFKSKATLTVDKSSSTAYMQLSSLTSEDSAVYYCELMQGYWGQGTLVTVSSASTKGPSVFPLA

PSSKSTSGGTAALGCLVKDYFPEPVTVSWNSGALTSGVHTFPAVLQSSGLYSLSSVVTVPSSSLGTQTYICN

VNHKPSNTKVDKKVEPKSCDKTHTCPPCPAPELAGAPSVFLFPPKPKDTLMISRTPEVTCVVVDVSHEDPEV

KFNWYVDGVEVHNAKTKPREEQYNSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKTTPPVLDSDGSFFLYSKLTVDKSRW

QQGNVFSCSVMHEALHNHYTQKSLSLSPGK

SEQ ID 60: Epitope
VLPDIVMEAPLN

SEQ ID 61: 2A10 VH humanised construct H99
QVQLVQSGAEVKKPGASVKVSCKASGYTFTSYWMHWVRQAPGQGLEWMGNINPSNGGTNYNEKFKSRVTMTR

DTSTSTVYMELSSLRSEDTAVYYCELGQSYWGQGTLVTVSS

SEQ ID NO. 62: CDR H3
GQSY

SEQ ID NO. 63: VH humanised construct H100
QVQLVQSGAEVKKPGASVKVSCKASGYTFTSYWMHWVRQAPGQGLEWIGNINPSNGGTNYNEKFKSRATMTR

DTSTSTAYMELSSLRSEDTAVYYCELGQSYWGQGTLVTVSS

SEQ ID NO. 64: VH humanised construct H101
QVQLVQSGAEVKKPGASVKVSCKASGYTFTSYWMHWVKQRPGQGLEWIGNINPSNGGTNYNEKFKSKATLTV

DKSTSTAYMELSSLRSEDTAVYYCELGQSYWGQGTLVTVSS

SEQ ID NO. 65: VH humanised construct H102
QVQLVQSGAEVKKPGASVKVSCKASGYTFTSYWMHWVRQAPGQGLEWIGNINPSNGGTNYNEKFKSKATMTR

DTSTSTAYMELSSLRSEDTAVYYCELGQSYWGQGTLVTVSS

SEQ ID NO. 66 2A10 VH humanised construct H98
QVQLVQSGAEVKKPGASVKVSCKASGYTFTSYWMHWVRQAPGQGLEWMGNINPSNGGTNYNEKFKSRVTMTR

DTSTSTVYMELSSLRSEDTAVYYCELMQGYWGQGTLVTVSS

SEQ ID NO. 67
DIVMTQSPLSLPVTLGQPASISCRSSKSLLYKDGKTYLNWFRQRPGQSPQLLIYLMSTRASGVPDRFSGGGS

GTDFTLKISRVEAEDVGVYYCQQLVEYPLTFGQGTKLEIK

SEQ ID NO. 68
DIVMTQSPLSLPVTLGQPASISCRSSKSLLYKDGKTYLNWFQQRPGQSPRLLIYLMSTRASGVPDRFSGGGS

GTDFTLKISRVEAEDVGVYYCQQLVEYPLTFGQGTKLEIK

SEQ ID NO. 69
DIVMTQSPLSLPVTLGQPASISCRSSKSLLYKDGKTYLNWFRQRPGQSPRLLIYLMSTRASGVPDRFSGGGS

GTDFTLKISRVEAEDVGVYYCQQLVEYPLTFGQGTKLEIK

SEQ ID NO. 70
DIVMTQSPLSNPVTLGQPVSISCRSSKSLLYKDGKTYLNWFRQRPGQSPQLLIYLMSTRASGVPDRFSGGGS

GTDFTLKISRVEAEDVGVYYCQQLVEYPLTFGQGTKLEIK

SEQ ID NO. 71
DIVMTQSPLSNPVTLGQPVSISCRSSKSLLYKDGKTYLNWFLQRPGQSPRLLIYLMSTRASGVPDRFSGGGS

GTDFTLKISRVEAEDVGVYYCQQLVEYPLTFGQGTKLEIK
```

SEQ ID NO. 72
DIVMTQSPLSNPVTLGQPVSISCRSSKSLLYKDGKTYLNWFRQRPGQSPRLLIYLMSTRASGVPDRFSGGGS

GTDFTLKISRVEAEDVGVYYCQQLVEYPLTFGQGTKLEIK

SEQ ID NO. 73
TPSPVLPDIVMEAPLN

SEQ ID NO. 74
VLPDIVMEAPLNSAVP

SEQ ID NO. 75
RQGY

SEQ ID NO. 76
IQGY

SEQ ID NO. 77
GDGY

SEQ ID NO. 78
GIGY

SEQ ID NO. 79
GSGY

SEQ ID NO. 80
GQNY

SEQ ID NO. 81
GQYY

SEQ ID NO. 82
GQLY

SEQ ID NO. 83
GQFY

SEQ ID NO. 84
GQGW

SEQ ID NO. 85
YESIKHEPENPPPYEE

SEQ ID NO. 86
WQGY

SEQ ID NO. 87
GAGY

SEQ ID NO. 88
GLGY

SEQ ID NO. 89
GVGY

SEQ ID NO. 90
GQWY

SEQ ID NO. 91
MSPILGYWKIKGLVQPTRLLLEYLEEKYEEHLYERDEGDKWRNKKFELGLEFPNLPYYIDGDVKLTQSMAII

RYIADKHNMLGGCPKEPAEISMLEGAVLDIRYGVSRIAYSKDFETLKVDFLSKLPEMLKMFEDRLCHKTYLN

GDHVTHPDFMLYDALDVVLYMDPMCLDAFPKLVCFKKRIEAIPQIDKYLKSSKYIAWPLQGWQATFGGGDHP

PKSDLEVLFQGPLGSMQESLYPVAQLCPSFEESEATPSPVLPDIVMEAPLNSAVPSAVASAVQPSLSPLEAS

SVNYESVKHEPENPPPYEEANNVSLKKVSGIKEEIKEPESIKAAVQETEAPYISIACDLIKETKLSAEPTPD

FSNYSEMAKVEQPLPDHSEIVEDSSPDSEPVDLFSDDSIPDVPQKQDEAVILVKENLTETSFESMIEHENKL

ERPHRD

SEQ ID NO. 92
MSPILGYWKIKGLVQPTRLLLEYLEEKYEEHLYERDEGDKWRNKKFELGLEFPNLPYYIDGDVKLTQSMAII

RYIADKHNMLGGCPKERAEISMLEGAVLDIRYGVSRIAYSKDFETLKVDFLSKLPEMLKMFEDRLCHKTYLN

GDHVTHPDFMLYDALDVVLYMDPMCLDAFPKLVCFKKRIEAIPQIDKYLKSSKYIAWPLQGWQATFGGGDHP

-continued

PKSDLEVLFQGPLGSKMDLVQTSEVMQESLYPAAQLCPSFEESEATPSPVLPDIVMEAPLNSAVPSAGASAV

QPSSSPLEASSVNYESIIHEPENPPPYEEAMSVSLKKVSGIKEEIKEPESINAAVQETEAPYISIACDLIKE

TKLSAEPTPDFSDYSEMAKVEQPVPDHSELVEDSSPDSEPVDLFSDDSIPDVPQKQDEAVMLVKENLPETSF

ESMIEHENKEKLSALPPEGGSSGRIVTD

SEQ ID NO. 93
MSPILGYWKIKGLVQPTRLLLEYLEEKYEEHLYERDEGDKWRNKKFELGLEFPNLPYYIDGDVKLTQSMAII

RYIADKHNMLGGCPKERAEISMLEGAVLDIRYGVSRIAYSKDFETLKVDFLSKLPEMLKMFEDRLCHKTYLN

GDHVTHPDFMLYDALDVVLYMDPMCLDAFPKLVCFKKRIEAIPQIDKYLKSSKYIAWPLQGWQATFGGGDHP

PKSDLEVLFQGPLGSVQDSLCPVAQLCPSFEESEATPSPVLPDIVMEAPLNSAVPSAGASAVQPSSSPLEAS

SVNFESVKHEPENPPPYEEAMNVSRKKVSGIKEEIKEPESINAAVQETEAPYISIACDLIKETKLSAEPTPD

FSSYSEMAKVEQPLPDHSELVEDSSPDSEPVDLFSDDSIPDVPQKQDEAVILVKETLTETSFESMIEHENKL

ERPHRD

SEQ ID NO. 94
MSPILGYWKIKGLVQPTRLLLEYLEEKYEEHLYERDEGDKWRNKKFELGLEFPNLPYYIDGDVKLTQSMAII

RYIADKHNMLGGCPKERAEISMLEGAVLDIRYGVSRIAYSKDFETLKVDFLSKLPEMLKMFEDRLCHKTYLN

GDHVTHPDFMLYDALDVVLYMDPMCLDAFPKLVCFKKRIEAIPQIDKYLKSSKYIAWPLQGWQATFGGGDHP

PKSDLEVLFQGPLGSIQESLYPTAQLCPSFEEAEATPSPVLPDIVMEAPLNSLLPSAGASVVQPSVSPLEAP

PPVSYDSIKLEPENPPPYEEAMNVALKALGTKEGIKEPESFNAAVQETEAPYISIACDLIKETKLSTEPSPD

FSNYSEIAKFEKSVPEHAELVEDSSPESEPVDLFSDDSIPEVPQTQEEAVMLMKESLTEVSETVAQHKEERL

SEQ ID NO. 95
DETFAL

SEQ ID NO. 96
ELSKTS

---

The invention claimed is:

1. An isolated antibody or fragment thereof, capable of binding to human NOGO-A, comprising the heavy chain and light chain variable region pair H28L16 SEQ ID NO: 49 + SEQ ID NO:14.

2. A pharmaceutical composition comprising an anti-NOGO antibody or fragment thereof of claim 1 and a pharmaceutically acceptable diluent or carrier.

* * * * *

SEQUENCE LISTING

<160> NUMBER OF SEQ ID NOS: 96

<210> SEQ ID NO 1
<211> LENGTH: 5
<212> TYPE: PRT
<213> ORGANISM: Mus musculus

<400> SEQUENCE: 1

Ser Tyr Trp Met His
 1               5

<210> SEQ ID NO 2
<211> LENGTH: 17
<212> TYPE: PRT
<213> ORGANISM: Mus musculus

<400> SEQUENCE: 2

Asn Ile Asn Pro Ser Asn Gly Gly Thr Asn Tyr Asn Glu Lys Phe Lys
 1               5                  10                  15

Ser

<210> SEQ ID NO 3
<211> LENGTH: 4
<212> TYPE: PRT
<213> ORGANISM: Mus musculus

<400> SEQUENCE: 3

Gly Gln Gly Tyr
 1

<210> SEQ ID NO 4
<211> LENGTH: 16
<212> TYPE: PRT
<213> ORGANISM: Mus musculus

<400> SEQUENCE: 4

Arg Ser Ser Lys Ser Leu Leu Tyr Lys Asp Gly Lys Thr Tyr Leu Asn
 1               5                  10                  15

<210> SEQ ID NO 5
<211> LENGTH: 7
<212> TYPE: PRT
<213> ORGANISM: Mus musculus

<400> SEQUENCE: 5

Leu Met Ser Thr Arg Ala Ser
 1               5

<210> SEQ ID NO 6
<211> LENGTH: 9
<212> TYPE: PRT
<213> ORGANISM: Mus musculus

<400> SEQUENCE: 6

Gln Gln Leu Val Glu Tyr Pro Leu Thr
 1               5

<210> SEQ ID NO 7
<211> LENGTH: 113
<212> TYPE: PRT
<213> ORGANISM: Mus musculus

<400> SEQUENCE: 7

Gln Val Gln Leu Gln Gln Pro Gly Thr Glu Leu Val Lys Pro Gly Ala
 1               5                  10                  15

Ser Val Lys Leu Ser Cys Lys Ala Ser Gly Tyr Thr Phe Thr Ser Tyr
             20                  25                  30

Trp Met His Trp Val Lys Gln Arg Pro Gly Gln Gly Leu Glu Trp Ile
         35                  40                  45

Gly Asn Ile Asn Pro Ser Asn Gly Gly Thr Asn Tyr Asn Glu Lys Phe
     50                  55                  60

Lys Ser Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Glu Leu Gly Gln Gly Tyr Trp Gly Gln Gly Thr Thr Leu Thr Val Ser
            100                 105                 110

Ser

<210> SEQ ID NO 8
<211> LENGTH: 112
<212> TYPE: PRT
<213> ORGANISM: Mus musculus

<400> SEQUENCE: 8

Asp Ile Val Ile Thr Gln Asp Glu Leu Ser Asn Pro Val Thr Ser Gly
 1               5                  10                  15

Glu Ser Val Ser Ile Ser Cys Arg Ser Ser Lys Ser Leu Leu Tyr Lys

```
                    20                  25                  30
Asp Gly Lys Thr Tyr Leu Asn Trp Phe Leu Gln Arg Pro Gly Gln Ser
             35                  40                  45

Pro Gln Leu Leu Ile Tyr Leu Met Ser Thr Arg Ala Ser Gly Val Ser
 50                  55                  60

Asp Arg Phe Ser Gly Ser Gly Ser Gly Thr Asp Phe Thr Leu Glu Ile
 65                  70                  75                  80

Ser Arg Val Lys Ala Glu Asp Val Gly Val Tyr Tyr Cys Gln Gln Leu
                 85                  90                  95

Val Glu Tyr Pro Leu Thr Phe Gly Ala Gly Thr Lys Leu Glu Leu Lys
            100                 105                 110

<210> SEQ ID NO 9
<211> LENGTH: 462
<212> TYPE: PRT
<213> ORGANISM: Artificial Sequence
<220> FEATURE:
<223> OTHER INFORMATION: Chimeric Ab comprising sequences from mus
      musculus and homo sapiens

<400> SEQUENCE: 9

Met Gly Trp Ser Cys Ile Ile Leu Phe Leu Val Ala Ala Ala Thr Gly
 1               5                  10                  15

Val His Ser Gln Val Gln Leu Gln Gln Pro Gly Thr Glu Leu Val Lys
             20                  25                  30

Pro Gly Ala Ser Val Lys Leu Ser Cys Lys Ala Ser Gly Tyr Thr Phe
         35                  40                  45

Thr Ser Tyr Trp Met His Trp Val Lys Gln Arg Pro Gly Gln Gly Leu
 50                  55                  60

Glu Trp Ile Gly Asn Ile Asn Pro Ser Asn Gly Gly Thr Asn Tyr Asn
 65                  70                  75                  80

Glu Lys Phe Lys Ser Lys Ala Thr Leu Thr Val Asp Lys Ser Ser Ser
                 85                  90                  95

Thr Ala Tyr Met Gln Leu Ser Ser Leu Thr Ser Glu Asp Ser Ala Val
            100                 105                 110

Tyr Tyr Cys Glu Leu Gly Gln Gly Tyr Trp Gly Gln Gly Thr Leu Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
```

```
                275                 280                 285
Lys Phe Asn Trp Tyr Val Asp Gly Val Glu Val His Asn Ala Lys Thr
290                 295                 300
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
                325                 330                 335
Lys Val Ser Asn Lys Ala Leu Pro Ala Pro Ile Glu Lys Thr Ile Ser
                340                 345                 350
Lys Ala Lys Gly Gln Pro Arg Glu Pro Gln Val Tyr Thr Leu Pro Pro
                355                 360                 365
Ser Arg Asp Glu Leu Thr Lys Asn Gln Val Ser Leu Thr Cys Leu Val
370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                405                 410                 415
Gly Ser Phe Phe Leu Tyr Ser Lys Leu Thr Val Asp Lys Ser Arg Trp
                420                 425                 430
Gln Gln Gly Asn Val Phe Ser Cys Ser Val Met His Glu Ala Leu His
                435                 440                 445
Asn His Tyr Thr Gln Lys Ser Leu Ser Leu Ser Pro Gly Lys
                450                 455                 460

<210> SEQ ID NO 10
<211> LENGTH: 239
<212> TYPE: PRT
<213> ORGANISM: Artificial Sequence
<220> FEATURE:
<223> OTHER INFORMATION: Chimeric Ab comprising sequences from mus
      musculus and homo sapiens

<400> SEQUENCE: 10

Met Arg Cys Ser Leu Gln Phe Leu Gly Val Leu Met Phe Trp Ile Ser
1               5                   10                  15
Gly Val Ser Gly Asp Ile Val Ile Thr Gln Asp Glu Leu Ser Asn Pro
                20                  25                  30
Val Thr Ser Gly Glu Ser Val Ser Ile Ser Cys Arg Ser Ser Lys Ser
                35                  40                  45
Leu Leu Tyr Lys Asp Gly Lys Thr Tyr Leu Asn Trp Phe Leu Gln Arg
                50                  55                  60
Pro Gly Gln Ser Pro Gln Leu Leu Ile Tyr Leu Met Ser Thr Arg Ala
65                  70                  75                  80
Ser Gly Val Ser Asp Arg Phe Ser Gly Ser Gly Ser Gly Thr Asp Phe
                85                  90                  95
Thr Leu Glu Ile Ser Arg Val Lys Ala Glu Asp Val Gly Val Tyr Tyr
                100                 105                 110
Cys Gln Gln Leu Val Glu Tyr Pro Leu Thr Phe Gly Ala Gly Thr Lys
                115                 120                 125
Leu Glu Leu Lys Arg Thr Val Ala Ala Pro Ser Val Phe Ile Phe Pro
                130                 135                 140
Pro Ser Asp Glu Gln Leu Lys Ser Gly Thr Ala Ser Val Val Cys Leu
145                 150                 155                 160
Leu Asn Asn Phe Tyr Pro Arg Glu Ala Lys Val Gln Trp Lys Val Asp
                165                 170                 175
Asn Ala Leu Gln Ser Gly Asn Ser Gln Glu Ser Val Thr Glu Gln Asp
```

```
                       180                 185                 190
Ser Lys Asp Ser Thr Tyr Ser Leu Ser Ser Thr Leu Thr Leu Ser Lys
            195                 200                 205

Ala Asp Tyr Glu Lys His Lys Val Tyr Ala Cys Glu Val Thr His Gln
            210                 215                 220

Gly Leu Ser Ser Pro Val Thr Lys Ser Phe Asn Arg Gly Glu Cys
225                 230                 235

<210> SEQ ID NO 11
<211> LENGTH: 113
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Asn Ile Asn Pro Ser Asn Gly Gly Thr Asn Tyr Asn Glu Lys Phe
    50                  55                  60

Lys Ser Arg Ala Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Glu Leu Gly Gln Gly Tyr Trp Gly Gln Gly Thr Leu Val Thr Val Ser
            100                 105                 110

Ser

<210> SEQ ID NO 12
<211> LENGTH: 113
<212> TYPE: PRT
<213> ORGANISM: Artificial Sequence
<220> FEATURE:
<223> OTHER INFORMATION: Humanized Ab construct comprising sequences
      from mus musculus and homo sapiens

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Asn Pro Ser Asn Gly Gly Thr Asn Tyr Asn Glu Lys Phe
    50                  55                  60

Lys Ser Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Glu Leu Gly Gln Gly Tyr Trp Gly Gln Gly Thr Leu Val Thr Val Ser
            100                 105                 110

Ser
```

-continued

```
<210> SEQ ID NO 13
<211> LENGTH: 112
<212> TYPE: PRT
<213> ORGANISM: Artificial Sequence
<220> FEATURE:
<223> OTHER INFORMATION: Humanized Ab construct comprising sequences
      from mus musculus and homo sapiens

<400> SEQUENCE: 13

Asp Ile Val Met Thr Gln Ser Pro Leu Ser Leu Pro Val Thr Leu Gly
 1               5                  10                  15

Gln Pro Ala Ser Ile Ser Cys Arg Ser Ser Lys Ser Leu Leu Tyr Lys
             20                  25                  30

Asp Gly Lys Thr Tyr Leu Asn Trp Phe Gln Gln Arg Pro Gly Gln Ser
         35                  40                  45

Pro Gln Leu Leu Ile Tyr Leu Met Ser Thr Arg Ala Ser Gly Val Pro
     50                  55                  60

Asp Arg Phe Ser Gly Gly Gly Ser Gly Thr Asp Phe Thr Leu Lys Ile
 65                  70                  75                  80

Ser Arg Val Glu Ala Glu Asp Val Gly Val Tyr Tyr Cys Gln Gln Leu
                 85                  90                  95

Val Glu Tyr Pro Leu Thr Phe Gly Gln Gly Thr Lys Leu Glu Ile Lys
            100                 105                 110

<210> SEQ ID NO 14
<211> LENGTH: 112
<212> TYPE: PRT
<213> ORGANISM: Artificial Sequence
<220> FEATURE:
<223> OTHER INFORMATION: Humanized Ab construct comprising sequences
      from mus musculus and homo sapiens

<400> SEQUENCE: 14

Asp Ile Val Met Thr Gln Ser Pro Leu Ser Asn Pro Val Thr Leu Gly
 1               5                  10                  15

Gln Pro Val Ser Ile Ser Cys Arg Ser Ser Lys Ser Leu Leu Tyr Lys
             20                  25                  30

Asp Gly Lys Thr Tyr Leu Asn Trp Phe Leu Gln Arg Pro Gly Gln Ser
         35                  40                  45

Pro Gln Leu Leu Ile Tyr Leu Met Ser Thr Arg Ala Ser Gly Val Pro
     50                  55                  60

Asp Arg Phe Ser Gly Gly Gly Ser Gly Thr Asp Phe Thr Leu Lys Ile
 65                  70                  75                  80

Ser Arg Val Glu Ala Glu Asp Val Gly Val Tyr Tyr Cys Gln Gln Leu
                 85                  90                  95

Val Glu Tyr Pro Leu Thr Phe Gly Gln Gly Thr Lys Leu Glu Ile Lys
            100                 105                 110

<210> SEQ ID NO 15
<211> LENGTH: 462
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 15

Met Gly Trp Ser Cys Ile Ile Leu Phe Leu Val Ala Thr Ala Thr Gly
 1               5                  10                  15

Val His Ser Gln Val Gln Leu Val Gln Ser Gly Ala Glu Val Lys Lys
             20                  25                  30
```

-continued

```
Pro Gly Ala Ser Val Lys Val Ser Cys Lys Ala Ser Gly Tyr Thr Phe
            35                  40                  45
Thr Ser Tyr Trp Met His Trp Val Arg Gln Ala Pro Gly Gln Gly Leu
 50                  55                  60
Glu Trp Ile Gly Asn Ile Asn Pro Ser Asn Gly Gly Thr Asn Tyr Asn
 65                  70                  75                  80
Glu Lys Phe Lys Ser Arg Ala Thr Met Thr Arg Asp Thr Ser Thr Ser
                 85                  90                  95
Thr Ala Tyr Met Glu Leu Ser Ser Leu Arg Ser Glu Asp Thr Ala Val
                100                 105                 110
Tyr Tyr Cys Glu Leu Gly Gln Gly Tyr Trp Gly Gln Gly Thr Leu Val
            115                 120                 125
Thr Val Ser Ser Ala Ser Thr Lys Gly Pro Ser Val Phe Pro Leu Ala
130                 135                 140
Pro Ser Ser Lys Ser Thr Ser Gly Gly Thr Ala Ala Leu Gly Cys Leu
145                 150                 155                 160
Val Lys Asp Tyr Phe Pro Glu Pro Val Thr Val Ser Trp Asn Ser Gly
                165                 170                 175
Ala Leu Thr Ser Gly Val His Thr Phe Pro Ala Val Leu Gln Ser Ser
            180                 185                 190
Gly Leu Tyr Ser Leu Ser Ser Val Val Thr Val Pro Ser Ser Ser Leu
        195                 200                 205
Gly Thr Gln Thr Tyr Ile Cys Asn Val Asn His Lys Pro Ser Asn Thr
210                 215                 220
Lys Val Asp Lys Lys Val Glu Pro Lys Ser Cys Asp Lys Thr His Thr
225                 230                 235                 240
Cys Pro Pro Cys Pro Ala Pro Glu Leu Ala Gly Ala Pro Ser Val Phe
                245                 250                 255
Leu Phe Pro Pro Lys Pro Lys Asp Thr Leu Met Ile Ser Arg Thr Pro
            260                 265                 270
Glu Val Thr Cys Val Val Val Asp Val Ser His Glu Asp Pro Glu Val
        275                 280                 285
Lys Phe Asn Trp Tyr Val Asp Gly Val Glu Val His Asn Ala Lys Thr
290                 295                 300
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
                325                 330                 335
Lys Val Ser Asn Lys Ala Leu Pro Ala Pro Ile Glu Lys Thr Ile Ser
            340                 345                 350
Lys Ala Lys Gly Gln Pro Arg Glu Pro Gln Val Tyr Thr Leu Pro Pro
        355                 360                 365
Ser Arg Asp Glu Leu Thr Lys Asn Gln Val Ser Leu Thr Cys Leu Val
370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
        435                 440                 445
Asn His Tyr Thr Gln Lys Ser Leu Ser Leu Ser Pro Gly Lys
450                 455                 460
```

<210> SEQ ID NO 16
<211> LENGTH: 462
<212> TYPE: PRT
<213> ORGANISM: Artificial Sequence
<220> FEATURE:
<223> OTHER INFORMATION: Humanized antibody construct comprising sequences from mus musculus and homo sapiens

<400> SEQUENCE: 16

```
Met Gly Trp Ser Cys Ile Ile Leu Phe Leu Val Ala Thr Ala Thr Gly
  1               5                  10                  15

Val His Ser Gln Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
         35                  40                  45

Thr Ser Tyr Trp Met His Trp Val Lys Gln Arg Pro Gly Gln Gly Leu
     50                  55                  60

Glu Trp Ile Gly Asn Ile Asn Pro Ser Asn Gly Thr Asn Tyr Asn
 65                  70                  75                  80

Glu Lys Phe Lys Ser Lys Ala Thr Leu Thr Val Asp Lys Ser Thr Ser
                 85                  90                  95

Thr Ala Tyr Met Glu Leu Ser Ser Leu Arg Ser Glu Asp Thr Ala Val
            100                 105                 110

Tyr Tyr Cys Glu Leu Gly Gln Gly Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365
```

```
Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
            450                 455                 460

<210> SEQ ID NO 17
<211> LENGTH: 238
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 17

Met Gly Trp Ser Cys Ile Ile Leu Phe Leu Val Ala Thr Ala Thr Gly
  1               5                  10                  15

Val His Ser Asp Ile Val Met Thr Gln Ser Pro Leu Ser Leu Pro Val
                 20                  25                  30

Thr Leu Gly Gln Pro Ala Ser Ile Ser Cys Arg Ser Ser Lys Ser Leu
             35                  40                  45

Leu Tyr Lys Asp Gly Lys Thr Tyr Leu Asn Trp Phe Gln Gln Arg Pro
 50                  55                  60

Gly Gln Ser Pro Gln Leu Leu Ile Tyr Leu Met Ser Thr Arg Ala Ser
 65                  70                  75                  80

Gly Val Pro Asp Arg Phe Ser Gly Gly Ser Gly Thr Asp Phe Thr
                 85                  90                  95

Leu Lys Ile Ser Arg Val Glu Ala Glu Asp Val Gly Val Tyr Tyr Cys
                100                 105                 110

Gln Gln Leu Val Glu Tyr Pro Leu Thr Phe Gly Gln Gly Thr Lys Leu
                115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
                180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
            210                 215                 220

Leu Ser Ser Pro Val Thr Lys Ser Phe Asn Arg Gly Glu Cys
225                 230                 235

<210> SEQ ID NO 18
<211> LENGTH: 238
<212> TYPE: PRT
<213> ORGANISM: Artificial Sequence
```

<220> FEATURE:
<223> OTHER INFORMATION: Humanized antibody construct comprising
     sequences from mus musculus and homo sapiens

<400> SEQUENCE: 18

Met Gly Trp Ser Cys Ile Ile Leu Phe Leu Val Ala Thr Ala Thr Gly
1               5                   10                  15

Val His Ser Asp Ile Val Met Thr Gln Ser Pro Leu Ser Asn Pro Val
            20                  25                  30

Thr Leu Gly Gln Pro Val Ser Ile Ser Cys Arg Ser Ser Lys Ser Leu
        35                  40                  45

Leu Tyr Lys Asp Gly Lys Thr Tyr Leu Asn Trp Phe Leu Gln Arg Pro
    50                  55                  60

Gly Gln Ser Pro Gln Leu Leu Ile Tyr Leu Met Ser Thr Arg Ala Ser
65                  70                  75                  80

Gly Val Pro Asp Arg Phe Ser Gly Gly Ser Gly Thr Asp Phe Thr
                85                  90                  95

Leu Lys Ile Ser Arg Val Glu Ala Glu Asp Val Gly Val Tyr Tyr Cys
            100                 105                 110

Gln Gln Leu Val Glu Tyr Pro Leu Thr Phe Gly Gln Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 19
<211> LENGTH: 339
<212> TYPE: DNA
<213> ORGANISM: Mus musculus

<400> SEQUENCE: 19
caggtccaac tgcagcagcc tgggactgaa ctggtgaagc ctggggcttc agtgaagctg      60
tcctgcaagg cttctggcta caccttcacc agctactgga tgcactgggt gaagcagagg     120
cctggacaag ccttgagtg gattggaaat attaatccta gcaatggtgg tactaactac      180
aatgagaagt tcaagagcaa ggccacactg actgtagaca atcctccag cacagcctac      240 atgcagctca gcagcctgac atctgaggac tctgcggtct attattgtga actgggacag     300
ggctactggg gccaaggcac cactctcaca gtctcctca                            339

<210> SEQ ID NO 20
<211> LENGTH: 336
<212> TYPE: DNA
<213> ORGANISM: Mus musculus

<400> SEQUENCE: 20
gatattgtga taacccagga tgaactctcc aatcctgtca cttctggaga atcagtttcc      60

```
atctcctgca ggtctagtaa gagtctccta tataaggatg ggaagacata cttgaattgg    120
tttctgcaga gaccaggaca atctcctcag ctcctgatct atttgatgtc cacccgtgca    180
tcaggagtct cagaccggtt tagtggcagt gggtcaggaa cagatttcac cctggaaatc    240
agtagagtga aggctgagga tgtgggtgtg tattactgtc aacaacttgt agagtatccg    300
ctcacgttcg gtgctgggac caagctggag ctgaaa                              336
```

<210> SEQ ID NO 21
<211> LENGTH: 1389
<212> TYPE: DNA
<213> ORGANISM: Artificial Sequence
<220> FEATURE:
<223> OTHER INFORMATION: Chimaeric antibody construct comprising
      sequences from mus musculus and homo sapiens

<400> SEQUENCE: 21

```
atgggatgga gctgtatcat cctctttttg gtagcagcag ctacaggtgt ccactcccag     60
gtccaactgc agcagcctgg gactgaactg gtgaagcctg ggcttcagt gaagctgtcc    120 tgcaaggctt ctggctacac cttcaccagc tactggatgc actgggtgaa gcagaggcct    180
ggacaaggcc ttgagtggat tggaaatatt aatcctagca atggtggtac taactacaat    240
gagaagttca gagcaaggc cacactgact gtagacaaat cctccagcac agcctacatg    300
cagctcagca gcctgacatc tgaggactct gcggtctatt attgtgaact gggacagggc    360
tactggggcc aaggcacact agtcacagtc tcctcagcct ccaccaaggg cccatcggtc    420
ttccccctgg cacctcctc aagagcacc tctggggca cagcggccct gggctgcctg    480
gtcaaggact acttccccga accggtgacg gtgtcgtgga actcaggcgc cctgaccagc    540
ggcgtgcaca ccttcccggc tgtcctacag tcctcaggac tctactccct cagcagcgtg    600
gtgaccgtgc cctccagcag cttgggcacc cagacctaca tctgcaacgt gaatcacaag    660
cccagcaaca ccaaggtgga caagaaagtt gagcccaaat cttgtgacaa aactcacaca    720
tgcccaccgt gcccagcacc tgaactcgcg ggggcaccgt cagtcttcct cttcccccca    780
aaacccaagg acaccctcat gatctcccgg acccctgagg tcacatgcgt ggtggtggac    840
gtgagccacg aagaccctga ggtcaagttc aactggtacg tggacggcgt ggaggtgcat    900
aatgccaaga caaagccgcg ggaggagcag tacaacagca cgtaccgtgt ggtcagcgtc    960
ctcaccgtcc tgcaccagga ctggctgaat ggcaaggagt acaagtgcaa ggtctccaac   1020
aaagccctcc cagcccccat cgagaaaacc atctccaaag ccaagggca gccccgagaa   1080 ccacaggtgt acaccctgcc cccatcccgg gatgagctga ccaagaacca ggtcagcctg   1140
acctgcctgg tcaaaggctt ctatcccagc gacatcgccg tggagtggga gagcaatggg   1200
cagccggaga caactacaa gaccacgcct cccgtgctgg actccgacgg ctccttcttc   1260
ctctacagca agctcaccgt ggacaagagc aggtggcagc aggggaacgt cttctcatgc   1320
tccgtgatgc atgaggctct gcacaaccac tacacgcaga gagcctctc cctgtctccg   1380 ggtaaatga                                                          1389
```

<210> SEQ ID NO 22
<211> LENGTH: 720
<212> TYPE: DNA
<213> ORGANISM: Artificial Sequence
<220> FEATURE:
<223> OTHER INFORMATION: Chimaeric antibody construct comprising
      sequences from mus musculus and homo sapiens

<400> SEQUENCE: 22

```
atgaggtgct ctcttcagtt tctgggggtg cttatgttct ggatctctgg agtcagtggg      60
gatattgtga taacccagga tgaactctcc aatcctgtca cttctggaga atcagtttcc     120
atctcctgca ggtctagtaa gagtctccta tataaggatg gaagacata cttgaattgg     180 tttctgcaga gaccaggaca atctcctcag ctcctgatct atttgatgtc cacccgtgca     240
tcaggagtct cagaccggtt tagtggcagt gggtcaggaa cagatttcac cctgaaatc     300 agtagagtga aggctgagga tgtggtgtg tattactgtc aacaacttgt agagtatccg      360
ctcacgttcg gtgctgggac caagctgag ctgaaacgta cggtggctgc accatctgtc     420
ttcatcttcc cgccatctga tgagcagttg aaatctggaa ctgcctctgt tgtgtgcctg     480
ctgaataact ctatcccag agaggccaaa gtacagtgga aggtggacaa cgccctccaa      540
tcgggtaact cccaggagag tgtcacagag caggacagca aggacagcac ctacagcctc     600
agcagcaccc tgacgctgag caaagcagac tacgagaaac acaaagtcta cgcctgcgaa     660
gtcacccatc agggcctgag ctcgcccgtc acaaagagct caacagggg agagtgttag      720
```

<210> SEQ ID NO 23
<211> LENGTH: 339
<212> TYPE: DNA
<213> ORGANISM: Artificial Sequence
<220> FEATURE:
<223> OTHER INFORMATION: Humanized antibody construct comprising
      sequences from mus musculus and homo sapiens

<400> SEQUENCE: 23

```
caggtgcagc tggtgcagtc tggggctgag gtgaagaagc ctggggcctc agtgaaggtt      60
tcctgcaagg catctggata caccttcacc agctactgga tgcactgggt gcgacaggcc     120
cctggacaag gcttgagtg gatcggaaat attaatccta gcaatggtgg tactaactac     180
aatgagaagt tcaagagcag agccaccatg accaggaca cgtccacgag cacagcctac      240
atggagctga gcagcctgag atctgaggac acggccgtgt attactgtga actgggacag     300
ggctactggg gccagggaac actagtcaca gtctcctca                             339
```

<210> SEQ ID NO 24
<211> LENGTH: 339
<212> TYPE: DNA
<213> ORGANISM: Artificial Sequence
<220> FEATURE:
<223> OTHER INFORMATION: Humanized antibody construct comprising
      sequences from mus musculus and homo sapiens

<400> SEQUENCE: 24

```
caggtgcagc tggtgcagtc tggggctgag gtgaagaagc ctggggcctc agtgaaggtt      60
tcctgcaagg catctggata caccttcacc agctactgga tgcactggt gaaacagcga     120 cctggacaag gcttgagtg gatcggaaat attaatccta gcaatggtgg tactaactac     180
aatgagaagt tcaagagcaa agccaccctc accgtcgaca aatccacgag cacagcctac     240
atggagctga gcagcctgag atctgaggac acggccgtgt attactgtga actgggacag     300
ggctactggg gccagggaac actagtcaca gtctcctca                             339
```

<210> SEQ ID NO 25
<211> LENGTH: 336
<212> TYPE: DNA
<213> ORGANISM: Artificial Sequence
<220> FEATURE:
<223> OTHER INFORMATION: Humanized antibody construct comprising
      sequences from mus musculus and homo sapiens

```
<400> SEQUENCE: 25
gatattgtga tgacccagtc tccactctcc ctgcccgtca cccttggaca gccggcctcc      60
atctcctgca ggtctagtaa gagtctccta tataaggatg gaagacata cttgaattgg     120 tttcagcaga ggccaggcca atctccacag ctcctaattt atttgatgtc cacccgtgca    180
tctggggtcc cagacagatt cagcggcggt gggtcaggca ctgatttcac actgaaaatc    240
agcagggtgg aggctgagga tgttggggtt tattactgcc aacaacttgt agagtatccg    300
ctcacgtttg gccaggggac caagctggag atcaaa                              336

<210> SEQ ID NO 26
<211> LENGTH: 336
<212> TYPE: DNA
<213> ORGANISM: Artificial Sequence
<220> FEATURE:
<223> OTHER INFORMATION: Humanized antibody construct comprising
      sequences from mus musculus and homo sapiens

<400> SEQUENCE: 26
gatattgtga tgacccagtc tccactctcc aaccccgtca cccttggaca gccggtctcc     60
atctcctgca ggtctagtaa gagtctccta tataaggatg gaagacata cttgaattgg    120 tttctccaga ggccaggcca atctccacag ctcctaattt atttgatgtc cacccgtgca   180
tctggggtcc cagacagatt cagcggcggt gggtcaggca ctgatttcac actgaaaatc   240
agcagggtgg aggctgagga tgttggggtt tattactgcc aacaacttgt agagtatccg   300
ctcacgtttg gccaggggac caagctggag atcaaa                             336

<210> SEQ ID NO 27
<211> LENGTH: 1389
<212> TYPE: DNA
<213> ORGANISM: Artificial Sequence
<220> FEATURE:
<223> OTHER INFORMATION: Humanized antibody construct comprising
      sequences from mus musculus and homo sapiens

<400> SEQUENCE: 27
atgggatgga gctgtatcat cctcttcttg gtagcaacag ctacaggtgt ccactcccag     60
gtgcagctgg tgcagtctgg ggctgaggtg aagaagcctg ggcctcagt gaaggtttcc    120 tgcaaggcat ctggatacac cttcaccagc tactggatgc actgggtgcg acaggcccct   180
ggacaagggc ttgagtggat cggaaatatt aatcctagca atggtggtac taactacaat   240
gagaagttca agagcagagc caccatgacc agggacacgt ccacgagcac agcctacatg   300
gagctgagca gcctgagatc tgaggacacg gccgtgtatt actgtgaact gggacagggc   360
tactggggcc aggaacact agtcacagtc tcctcagcct ccaccaaggg cccatcggtc    420
ttccccctgg cacctcctc caagagcacc tctggggca gcggccct gggctgcctg     480 gtcaaggact acttccccga accggtgacg gtgtcgtgga actcaggcgc cctgaccagc   540
ggcgtgcaca ccttcccggc tgtcctacag tcctcaggac tctactccct cagcagcgtg   600
gtgaccgtgc cctccagcag cttgggcacc cagacctaca tctgcaacgt gaatcacaag   660
cccagcaaca ccaaggtgga caagaaagtt gagcccaaat cttgtgacaa aactcacaca   720
tgcccaccgt gcccagcacc tgaactcgcg ggggcaccgt cagtcttcct cttcccccca   780
aaacccaagg acaccctcat gatctcccgg acccctgagg tcacatgcgt ggtggtggac   840
gtgagccacg aagaccctga ggtcaagttc aactggtacg tggacggcgt ggaggtgcat   900
aatgccaaga caaagccgcg ggaggagcag tacaacagca cgtaccgtgt ggtcagcgtc   960
```

```
ctcaccgtcc tgcaccagga ctggctgaat ggcaaggagt acaagtgcaa ggtctccaac    1020
aaagccctcc cagcccccat cgagaaaacc atctccaaag ccaaagggca gccccgagaa    1080
ccacaggtgt acaccctgcc cccatcccgg gatgagctga ccaagaacca ggtcagcctg    1140
acctgcctgg tcaaaggctt ctatcccagc gacatcgccg tggagtggga gagcaatggg    1200
cagccggaga acaactacaa gaccacgcct cccgtgctgg actccgacgg ctccttcttc    1260
ctctacagca agctcaccgt ggacaagagc aggtggcagc aggggaacgt cttctcatgc    1320
tccgtgatgc atgaggctct gcacaaccac tacacgcaga agagcctctc cctgtctccg    1380
ggtaaatga                                                            1389
```

<210> SEQ ID NO 28
<211> LENGTH: 1389
<212> TYPE: DNA
<213> ORGANISM: Artificial Sequence
<220> FEATURE:
<223> OTHER INFORMATION: Humanized antibody construct comprising
      sequences from mus musculus and homo sapiens

<400> SEQUENCE: 28

```
atgggatgga gctgtatcat cctcttcttg gtagcaacag ctacaggtgt ccactcccag     60
gtgcagctgg tgcagtctgg ggctgaggtg aagaagcctg ggcctcagt gaaggtttcc     120 tgcaaggcat ctggatacac cttcaccagc tactggatgc actgggtgaa acagcgacct    180
ggacaagggc ttgagtggat cggaaatatt aatcctagca atggtggtac taactacaat    240
gagaagttca gagcaaagc caccctcacc gtcgacaaat ccacgagcac agcctacatg    300
gagctgagca gcctgagatc tgaggacacg gccgtgtatt actgtgaact gggacagggc    360
tactggggcc aggaaacact agtcacagtc tcctcagcct ccaccaaggg cccatcggtc    420
ttccccctgg caccctcctc caagagcacc tctgggggca cagcggccct gggctgcctg    480
gtcaaggact acttccccga accggtgacg gtgtcgtgga actcaggcgc cctgaccagc    540
ggcgtgcaca ccttcccggc tgtcctacag tcctcaggac tctactccct cagcagcgtg    600
gtgaccgtgc cctccagcag cttgggcacc cagacctaca tctgcaacgt gaatcacaag    660
cccagcaaca ccaaggtgga caagaaagtt gagcccaaat cttgtgacaa aactcacaca    720
tgcccaccgt gcccagcacc tgaactcgcg ggggcaccgt cagtcttcct cttccccca    780 aaacccaagg acaccctcat gatctcccgg acccctgagg tcacatgcgt ggtggtggac    840
gtgagccacg aagaccctga ggtcaagttc aactggtacg tggacggcgt ggaggtgcat    900
aatgccaaga caaagccgcg ggaggagcag tacaacagca cgtaccgtgt ggtcagcgtc    960
ctcaccgtcc tgcaccagga ctggctgaat ggcaaggagt acaagtgcaa ggtctccaac    1020
aaagccctcc cagcccccat cgagaaaacc atctccaaag ccaaagggca gccccgagaa    1080
ccacaggtgt acaccctgcc cccatcccgg gatgagctga ccaagaacca ggtcagcctg    1140
acctgcctgg tcaaaggctt ctatcccagc gacatcgccg tggagtggga gagcaatggg    1200
cagccggaga acaactacaa gaccacgcct cccgtgctgg actccgacgg ctccttcttc    1260
ctctacagca agctcaccgt ggacaagagc aggtggcagc aggggaacgt cttctcatgc    1320
tccgtgatgc atgaggctct gcacaaccac tacacgcaga agagcctctc cctgtctccg    1380
ggtaaatga                                                            1389
```

<210> SEQ ID NO 29
<211> LENGTH: 717
<212> TYPE: DNA
<213> ORGANISM: Artificial Sequence

```
<220> FEATURE:
<223> OTHER INFORMATION: Humanized antibody construct comprising
      sequences from mus musculus and homo sapiens

<400> SEQUENCE: 29
atgggatgga gctgtatcat cctcttcttg gtagcaacag ctacaggtgt ccactccgat    60
attgtgatga cccagtctcc actctccctg cccgtcaccc ttggacagcc ggcctccatc   120
tcctgcaggt ctagtaagag tctcctatat aaggatggga agacatactt gaattggttt   180
cagcagaggc caggccaatc tccacagctc ctaatttatt tgatgtccac ccgtgcatct   240
ggggtcccag acagattcag cggcggtggg tcaggcactg atttcacact gaaaatcagc   300
agggtggagg ctgaggatgt tggggtttat tactgccaac aacttgtaga gtatccgctc   360
acgtttggcc aggggaccaa gctggagatc aaacgtacgg tggctgcacc atctgtcttc   420
atcttcccgc catctgatga gcagttgaaa tctggaactg cctctgttgt gtgcctgctg   480
aataacttct atcccagaga ggccaaagta cagtggaagg tggacaacgc cctccaatcg   540
ggtaactccc aggagagtgt cacagagcag gacagcaagg acagcaccta cagcctcagc   600
agcaccctga cgctgagcaa agcagactac gagaaacaca agtctacgc ctgcgaagtc   660 acccatcagg gcctgagctc gcccgtcaca aagagcttca caggggaga gtgttag     717

<210> SEQ ID NO 30
<211> LENGTH: 717
<212> TYPE: DNA
<213> ORGANISM: Artificial Sequence
<220> FEATURE:
<223> OTHER INFORMATION: Humanized antibody construct comprising
      sequences from mus musculus and homo sapiens

<400> SEQUENCE: 30
atgggatgga gctgtatcat cctcttcttg gtagcaacag ctacaggtgt ccactccgat    60
attgtgatga cccagtctcc actctccaac cccgtcaccc ttggacagcc ggtctccatc   120
tcctgcaggt ctagtaagag tctcctatat aaggatggga agacatactt gaattggttt   180
ctccagaggc caggccaatc tccacagctc ctaatttatt tgatgtccac ccgtgcatct   240
ggggtcccag acagattcag cggcggtggg tcaggcactg atttcacact gaaaatcagc   300
agggtggagg ctgaggatgt tggggtttat tactgccaac aacttgtaga gtatccgctc   360
acgtttggcc aggggaccaa gctggagatc aaacgtacgg tggctgcacc atctgtcttc   420
atcttcccgc catctgatga gcagttgaaa tctggaactg cctctgttgt gtgcctgctg   480
aataacttct atcccagaga ggccaaagta cagtggaagg tggacaacgc cctccaatcg   540
ggtaactccc aggagagtgt cacagagcag gacagcaagg acagcaccta cagcctcagc   600
agcaccctga cgctgagcaa agcagactac gagaaacaca agtctacgc ctgcgaagtc   660 acccatcagg gcctgagctc gcccgtcaca aagagcttca caggggaga gtgttag     717

<210> SEQ ID NO 31
<211> LENGTH: 19
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 31

Met Gly Trp Ser Cys Ile Ile Leu Phe Leu Val Ala Thr Ala Thr Gly
 1               5                  10                  15

Val His Ser
```

<210> SEQ ID NO 32
<211> LENGTH: 439
<212> TYPE: PRT
<213> ORGANISM: Homo Sapiens

<400> SEQUENCE: 32

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
    210                 215                 220

Phe Gln Gly Pro Leu Gly Ser Met Gln Glu Ser Leu Tyr Pro Ala Ala
225                 230                 235                 240

Gln Leu Cys Pro Ser Phe Glu Glu Ser Glu Ala Thr Pro Ser Pro Val
                245                 250                 255

Leu Pro Asp Ile Val Met Glu Ala Pro Leu Asn Ser Ala Val Pro Ser
            260                 265                 270

Ala Gly Ala Ser Val Ile Gln Pro Ser Ser Ser Pro Leu Glu Ala Ser
        275                 280                 285

Ser Val Asn Tyr Glu Ser Ile Lys His Glu Pro Glu Asn Pro Pro Pro
    290                 295                 300

Tyr Glu Glu Ala Met Ser Val Ser Leu Lys Lys Val Ser Gly Ile Lys
305                 310                 315                 320

Glu Glu Ile Lys Glu Pro Glu Asn Ile Asn Ala Ala Leu Gln Glu Thr
                325                 330                 335

Glu Ala Pro Tyr Ile Ser Ile Ala Cys Asp Leu Ile Lys Glu Thr Lys
            340                 345                 350

Leu Ser Ala Glu Pro Ala Pro Asp Phe Ser Asp Tyr Ser Glu Met Ala
        355                 360                 365

Lys Val Glu Gln Pro Val Pro Asp His Ser Glu Leu Val Glu Asp Ser
    370                 375                 380

```
Ser Pro Asp Ser Glu Pro Val Asp Leu Phe Ser Asp Ser Ile Pro
385                 390                 395                 400

Asp Val Pro Gln Lys Gln Asp Glu Thr Val Met Leu Val Lys Glu Ser
            405                 410                 415

Leu Thr Glu Thr Ser Phe Glu Ser Met Ile Glu Tyr Glu Asn Lys Glu
            420                 425                 430

Leu Glu Arg Pro His Arg Asp
            435

<210> SEQ ID NO 33
<211> LENGTH: 113
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Asn Ile Asn Pro Ser Asn Gly Gly Thr Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Glu Leu Gly Gln Gly Tyr Trp Gly Gln Gly Thr Leu Val Thr Val Ser
            100                 105                 110

Ser

<210> SEQ ID NO 34
<211> LENGTH: 112
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 34

Asp Ile Val Ile Thr Gln Ser Pro Leu Ser Leu Pro Val Thr Leu Gly
1               5                   10                  15

Gln Pro Ala Ser Ile Ser Cys Arg Ser Ser Lys Ser Leu Leu Tyr Lys
            20                  25                  30

Asp Gly Lys Thr Tyr Leu Asn Trp Phe Gln Gln Arg Pro Gly Gln Ser
            35                  40                  45

Pro Gln Leu Leu Ile Tyr Leu Met Ser Thr Arg Ala Ser Gly Val Pro
    50                  55                  60

Asp Arg Phe Ser Gly Gly Gly Ser Gly Thr Asp Phe Thr Leu Lys Ile
65                  70                  75                  80

Ser Arg Val Glu Ala Glu Asp Val Gly Val Tyr Tyr Cys Gln Gln Leu
                85                  90                  95

Val Glu Tyr Pro Leu Thr Phe Gly Gln Gly Thr Lys Leu Glu Ile Lys
            100                 105                 110
```

```
<210> SEQ ID NO 35
<211> LENGTH: 462
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 35

Met Gly Trp Ser Cys Ile Ile Leu Phe Leu Val Ala Thr Ala Thr Gly
 1               5                  10                  15

Val His Ser Gln Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
         35                  40                  45

Thr Ser Tyr Trp Met His Trp Val Arg Gln Ala Pro Gly Gln Gly Leu
     50                  55                  60

Glu Trp Met Gly Asn Ile Asn Pro Ser Asn Gly Gly Thr Asn Tyr Asn
65                  70                  75                  80

Glu Lys Phe Lys Ser Arg Val Thr Met Thr Arg Asp Thr Ser Thr Ser
                 85                  90                  95

Thr Val Tyr Met Glu Leu Ser Ser Leu Arg Ser Glu Asp Thr Ala Val
            100                 105                 110

Tyr Tyr Cys Glu Leu Gly Gln Gly Tyr Trp Gly Gln Gly Thr Leu Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
```

```
                370             375             380
Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
                435                 440                 445

Asn His Tyr Thr Gln Lys Ser Leu Ser Leu Ser Pro Gly Lys
            450                 455                 460

<210> SEQ ID NO 36
<211> LENGTH: 238
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 36

Met Gly Trp Ser Cys Ile Ile Leu Phe Leu Val Ala Thr Ala Thr Gly
1               5                   10                  15

Val His Ser Asp Ile Val Ile Thr Gln Ser Pro Leu Ser Leu Pro Val
                20                  25                  30

Thr Leu Gly Gln Pro Ala Ser Ile Ser Cys Arg Ser Ser Lys Ser Leu
            35                  40                  45

Leu Tyr Lys Asp Gly Lys Thr Tyr Leu Asn Trp Phe Gln Gln Arg Pro
    50                  55                  60

Gly Gln Ser Pro Gln Leu Leu Ile Tyr Leu Met Ser Thr Arg Ala Ser
65                  70                  75                  80

Gly Val Pro Asp Arg Phe Ser Gly Gly Ser Gly Thr Asp Phe Thr
                85                  90                  95

Leu Lys Ile Ser Arg Val Glu Ala Glu Asp Val Gly Val Tyr Tyr Cys
                100                 105                 110

Gln Gln Leu Val Glu Tyr Pro Leu Thr Phe Gly Gln Gly Thr Lys Leu
            115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 37
<211> LENGTH: 339
<212> TYPE: DNA
<213> ORGANISM: Artificial Sequence
<220> FEATURE:
<223> OTHER INFORMATION: Humanized antibody construct comprising
``` sequences from mus musculus and homo sapiens

<400> SEQUENCE: 37

| caggtgcagc tggtgcagtc tggggctgag gtgaagaagc ctggggcctc agtgaaggtt | 60 |
| tcctgcaagg catctggata cacctcacc agctactgga tgcactgggt gcgacaggcc | 120 |
| cctggacaag gcttgagtg gatgggaaat attaatccta gcaatggtgg tactaactac | 180 |
| aatgagaagt tcaagagcag agtcaccatg accagggaca cgtccacgag cacagtctac | 240 |
| atggagctga gcagcctgag atctgaggac acggccgtgt attactgtga actgggacag | 300 |
| ggctactggg gccagggaac actagtcaca gtctcctca | 339 |

<210> SEQ ID NO 38
<211> LENGTH: 336
<212> TYPE: DNA
<213> ORGANISM: Artificial Sequence
<220> FEATURE:
<223> OTHER INFORMATION: Humanized antibody construct comprising
      sequences from mus musculus and homo sapiens

<400> SEQUENCE: 38

| gatattgtga tacccagtc tccactctcc ctgcccgtca cccttggaca gccggcctcc | 60 |
| atctcctgca ggtctagtaa gagtctccta tataaggatg gaagacata cttgaattgg | 120 |
| tttcagcaga ggccaggcca atctccacag ctcctaattt atttgatgtc acccgtgca | 180 |
| tctggggtcc cagacagatt cagcggcggt gggtcaggca ctgatttcac actgaaaatc | 240 |
| agcaggtgg aggctgagga tgttggggtt tattactgcc aacaacttgt agagtatccg | 300 |
| ctcacgtttg gccaggggac caagctggag atcaaa | 336 |

<210> SEQ ID NO 39
<211> LENGTH: 1389
<212> TYPE: DNA
<213> ORGANISM: Artificial Sequence
<220> FEATURE:
<223> OTHER INFORMATION: Humanized antibody construct comprising
      sequences from mus musculus and homo sapiens

<400> SEQUENCE: 39

| atgggatgga gctgtatcat cctcttcttg gtagcaacag ctacaggtgt ccactcccag | 60 |
| gtgcagctgg tgcagtctgg ggctgaggtg aagaagcctg ggcctcagt gaaggtttcc | 120 |
| tgcaaggcat ctggatacac cttcaccagc tactggatgc actgggtgcg acaggcccct | 180 |
| ggacaagggc ttgagtggat gggaaatatt aatcctagca atggtggtac taactacaat | 240 |
| gagaagttca gagcagagt caccatgacc agggacacgt ccacgagcac agtctacatg | 300 |
| gagctgagca gcctgagatc tgaggacacg gccgtgtatt actgtgaact gggacagggc | 360 |
| tactggggcc aggaacact agtcacagtc tcctcagcct ccaccaaggg cccatcggtc | 420 |
| ttccccctgg cacctcctc caagagcacc tctgggggca gcggccct gggctgcctg | 480 |
| gtcaaggact acttccccga accggtgacg gtgtcgtgga actcaggcgc cctgaccagc | 540 |
| ggcgtgcaca ccttcccggc tgtcctacag tcctcaggac tctactccct cagcagcgtg | 600 |
| gtgaccgtgc cctccagcag cttgggcacc cagacctaca tctgcaacgt gaatcacaag | 660 |
| cccagcaaca ccaaggtgga caagaaagtt gagcccaaat cttgtgacaa aactcacaca | 720 |
| tgcccaccgt gcccagcacc tgaactcgcg gggcaccgt cagtcttcct cttccccca | 780 |
| aaacccaagg acaccctcat gatctcccgg acccctgagg tcacatgcgt ggtggtggac | 840 |
| gtgagccacg aagaccctga ggtcaagttc aactggtacg tggacggcgt ggaggtgcat | 900 |

```
aatgccaaga caaagccgcg ggaggagcag tacaacagca cgtaccgtgt ggtcagcgtc    960
ctcaccgtcc tgcaccagga ctggctgaat ggcaaggagt acaagtgcaa ggtctccaac   1020
aaagccctcc cagcccccat cgagaaaacc atctccaaag ccaaagggca gccccgagaa   1080
ccacaggtgt acaccctgcc cccatcccgg gatgagctga ccaagaacca ggtcagcctg   1140
acctgcctgg tcaaaggctt ctatcccagc gacatcgccg tggagtggga gagcaatggg   1200
cagccggaga acaactacaa gaccacgcct cccgtgctgg actccgacgg ctccttcttc   1260
ctctacagca agctcaccgt ggacaagagc aggtggcagc aggggaacgt cttctcatgc   1320
tccgtgatgc atgaggctct gcacaaccac tacacgcaga gagcctctc cctgtctccg   1380 ggtaaatga                                                          1389
```

<210> SEQ ID NO 40
<211> LENGTH: 717
<212> TYPE: DNA
<213> ORGANISM: Artificial Sequence
<220> FEATURE:
<223> OTHER INFORMATION: Humanized antibody construct comprising
      sequences from mus musculus and homo sapiens

<400> SEQUENCE: 40

```
atgggatgga gctgtatcat cctcttcttg gtagcaacag ctacaggtgt ccactccgat     60
attgtgataa cccagtctcc actctccctg cccgtcaccc ttggacagcc ggcctccatc    120
tcctgcaggt ctagtaagag tctcctatat aaggatggga agacatactt gaattggttt    180
cagcagaggc caggccaatc tccacagctc ctaatttatt tgatgtccac ccgtgcatct    240
ggggtcccag acagattcag cggcggtggg tcaggcactg atttcacact gaaaatcagc    300
agggtggagg ctgaggatgt gggggtttat tactgcaac aacttgtaga gtatccgctc     360
acgtttggcc aggggaccaa gctggagatc aaacgtacgg tggctgcacc atctgtcttc    420
atcttcccgc catctgatga gcagttgaaa tctggaactg cctctgttgt gtgcctgctg    480
aataacttct atcccagaga ggccaaagta cagtggaagg tggacaacgc cctccaatcg    540
ggtaactccc aggagagtgt cacagagcag gacagcaagg acagcaccta cagcctcagc    600
agcaccctga cgctgagcaa agcagactac gagaaacaca agtctacgc ctgcgaagtc     660 acccatcagg gcctgagctc gcccgtcaca aagagcttca caggggaga gtgttag         717
```

<210> SEQ ID NO 41
<211> LENGTH: 113
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 41

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
             20                  25                  30

Trp Met His Trp Val Arg Gln Ala Pro Gly Gln Gly Leu Glu Trp Ile
         35                  40                  45

Gly Asn Ile Asn Pro Ser Asn Gly Gly Thr Asn Tyr Asn Glu Lys Phe
     50                  55                  60

Lys Ser Lys Ala Thr Met Thr Arg Asp Thr Ser Thr Ser Thr Ala Tyr
 65                  70                  75                  80

Met Glu Leu Ser Ser Leu Arg Ser Glu Asp Thr Ala Val Tyr Tyr Cys
```

```
                  85                  90                  95
Glu Leu Gly Gln Gly Tyr Trp Gly Gln Gly Thr Leu Val Thr Val Ser
                100                 105                 110
Ser

<210> SEQ ID NO 42
<211> LENGTH: 462
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 42

Met Gly Trp Ser Cys Ile Ile Leu Phe Leu Val Ala Thr Ala Thr Gly
  1               5                  10                  15

Val His Ser Gln Val Gln Leu Val Gln Ser Gly Ala Glu Val Lys Lys
                 20                  25                  30

Pro Gly Ala Ser Val Lys Val Ser Cys Lys Ala Ser Gly Tyr Thr Phe
             35                  40                  45

Thr Ser Tyr Trp Met His Trp Val Arg Gln Ala Pro Gly Gln Gly Leu
         50                  55                  60

Glu Trp Ile Gly Asn Ile Asn Pro Ser Asn Gly Gly Thr Asn Tyr Asn
 65                  70                  75                  80

Glu Lys Phe Lys Ser Lys Ala Thr Met Thr Arg Asp Thr Ser Thr Ser
                 85                  90                  95

Thr Ala Tyr Met Glu Leu Ser Ser Leu Arg Ser Glu Asp Thr Ala Val
                100                 105                 110

Tyr Tyr Cys Glu Leu Gly Gln Gly Tyr Trp Gly Gln Gly Thr Leu Val
            115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335
```

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Thr Cys Leu Val
        370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 43
<211> LENGTH: 339
<212> TYPE: DNA
<213> ORGANISM: Artificial Sequence
<220> FEATURE:
<223> OTHER INFORMATION: Humanized antibody construct comprising
      sequences from mus musculus and homo sapiens

<400> SEQUENCE: 43
caggtgcagc tggtgcagtc tggggctgag gtgaagaagc ctggggcctc agtgaaggtt      60
tcctgcaagg catctggata caccttcacc agctactgga tgcactgggt gcgacaggcc     120
cctggacaag gcttgagtg gatcggaaat attaatccta gcaatggtgg tactaactac     180
aatgagaagt tcaagagcaa ggccaccatg accagggaca cgtccacgag cacagcctac     240
atggagctga gcagcctgag atctgaggac acggccgtgt attactgtga actgggacag     300
ggctactggg gccagggaac actagtcaca gtctcctca                            339

<210> SEQ ID NO 44
<211> LENGTH: 1389
<212> TYPE: DNA
<213> ORGANISM: Artificial Sequence
<220> FEATURE:
<223> OTHER INFORMATION: Humanized antibody construct comprising
      sequences from mus musculus and homo sapiens

<400> SEQUENCE: 44
atgggatgga gctgtatcat cctcttcttg gtagcaacag ctacaggtgt ccactcccag      60
gtgcagctgg tgcagtctgg ggctgaggtg aagaagcctg gggcctcagt gaaggtttcc     120
tgcaaggcat ctggatacac cttcaccagc tactggatgc actgggtgcg acaggcccct     180 ggacaaggc ttgagtggat cggaaatatt aatcctagca atggtggtac taactacaat     240
gagaagttca gagcaaggc caccatgacc agggacacgt ccacgagcac agcctacatg     300
gagctgagca gcctgagatc tgaggacacg gccgtgtatt actgtgaact gggacagggc     360
tactggggcc agggaacact agtcacagtc tcctcagcct ccaccaaggg cccatcggtc     420
ttccccctgg caccctcctc caagagcacc tctggggggca gcggccct gggctgcctg     480 gtcaaggact acttccccga accggtgacg gtgtcgtgga actcaggcgc cctgaccagc     540
ggcgtgcaca ccttccggc tgtcctacag tcctcaggac tctactccct cagcagcgtg     600
gtgaccgtgc cctccagcag cttgggcacc cagacctaca tctgcaacgt gaatcacaag     660

-continued

```
cccagcaaca ccaaggtgga caagaaagtt gagcccaaat cttgtgacaa aactcacaca    720
tgcccaccgt gcccagcacc tgaactcgcg ggggcaccgt cagtcttcct cttcccccca    780
aaacccaagg acaccctcat gatctcccgg acccctgagg tcacatgcgt ggtggtggac    840
gtgagccacg aagaccctga ggtcaagttc aactggtacg tggacggcgt ggaggtgcat    900
aatgccaaga caaagccgcg ggaggagcag tacaacagca cgtaccgtgt ggtcagcgtc    960
ctcaccgtcc tgcaccagga ctggctgaat ggcaaggagt acaagtgcaa ggtctccaac   1020
aaagccctcc cagcccccat cgagaaaacc atctccaaag ccaaagggca gccccgagaa   1080
ccacaggtgt acaccctgcc cccatcccgg gatgagctga ccaagaacca ggtcagcctg   1140
acctgcctgg tcaaaggctt ctatcccagc gacatcgccg tggagtggga gagcaatggg   1200
cagccggaga acaactacaa gaccacgcct cccgtgctgg actccgacgg ctccttcttc   1260
ctctacagca agctcaccgt ggacaagagc aggtggcagc aggggaacgt cttctcatgc   1320
tccgtgatgc atgaggctct gcacaaccac tacacgcaga agagcctctc cctgtctccg   1380
ggtaaatga                                                            1389
```

<210> SEQ ID NO 45
<211> LENGTH: 4
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 45

Met Gln Gly Tyr
 1

<210> SEQ ID NO 46
<211> LENGTH: 200
<212> TYPE: PRT
<213> ORGANISM: Callithrix jacchus

<400> SEQUENCE: 46

Val Gln Asp Ser Leu Cys Pro Val Ala Gln Leu Cys Pro Ser Phe Glu
 1               5                  10                  15

Glu Ser Glu Ala Thr Pro Ser Pro Val Leu Pro Asp Ile Val Met Glu
            20                  25                  30

Ala Pro Leu Asn Ser Ala Val Pro Ser Ala Gly Ala Ser Ala Val Gln
        35                  40                  45

Pro Ser Ser Ser Pro Leu Glu Ala Ser Val Asn Phe Glu Ser Val
    50                  55                  60

Lys His Glu Pro Glu Asn Pro Pro Tyr Glu Ala Met Asn Val
65                  70                  75                  80

Ser Arg Lys Lys Val Ser Gly Ile Lys Glu Glu Ile Lys Glu Pro Glu
                85                  90                  95

Ser Ile Asn Ala Ala Val Gln Glu Thr Glu Ala Pro Tyr Ile Ser Ile
            100                 105                 110

Ala Cys Asp Leu Ile Lys Glu Thr Lys Leu Ser Ala Glu Pro Thr Pro
        115                 120                 125

Asp Phe Ser Ser Tyr Ser Glu Met Ala Lys Val Glu Gln Pro Leu Pro
    130                 135                 140

Asp His Ser Glu Leu Val Glu Asp Ser Ser Pro Asp Ser Glu Pro Val
145                 150                 155                 160

Asp Leu Phe Ser Asp Asp Ser Ile Pro Asp Val Pro Gln Lys Gln Asp

```
                              165                 170                 175
Glu Ala Val Ile Leu Val Lys Glu Thr Leu Thr Glu Thr Ser Phe Glu
                180                 185                 190

Ser Met Ile Glu His Glu Asn Lys
        195                 200

<210> SEQ ID NO 47
<211> LENGTH: 113
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Ile
            35                  40                  45

Gly Asn Ile Asn Pro Ser Gly Gly Thr Asn Tyr Asn Glu Lys Phe
    50                  55                  60

Lys Ser Arg Ala Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Glu Leu Met Gln Gly Tyr Trp Gly Gln Gly Thr Leu Val Thr Val Ser
                100                 105                 110

Ser

<210> SEQ ID NO 48
<211> LENGTH: 113
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Asn Ile Asn Pro Ser Asn Gly Gly Thr Asn Tyr Asn Glu Lys Phe
    50                  55                  60

Lys Ser Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Glu Leu Met Gln Gly Tyr Trp Gly Gln Gly Thr Leu Val Thr Val Ser
                100                 105                 110

Ser

<210> SEQ ID NO 49
<211> LENGTH: 113
<212> TYPE: PRT
```

<213> ORGANISM: Artificial Sequence
<220> FEATURE:
<223> OTHER INFORMATION: Humanized antibody construct comprising
      sequences from mus musculus and homo sapiens

<400> SEQUENCE: 49

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Asn Ile Asn Pro Ser Asn Gly Gly Thr Asn Tyr Asn Glu Lys Phe
    50                  55                  60

Lys Ser Lys Ala Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Glu Leu Met Gln Gly Tyr Trp Gly Gln Gly Thr Leu Val Thr Val Ser
            100                 105                 110

Ser

<210> SEQ ID NO 50
<211> LENGTH: 339
<212> TYPE: DNA
<213> ORGANISM: Artificial Sequence
<220> FEATURE:
<223> OTHER INFORMATION: Humanized antibody construct comprising
      sequences from mus musculus and homo sapiens

<400> SEQUENCE: 50
caggtgcagc tggtgcagtc tggggctgag gtgaagaagc ctggggcctc agtgaaggtt      60
tcctgcaagg catctggata caccttcacc agctactgga tgcactgggt gcgacaggcc     120
cctggacaag ggcttgagtg gatcggaaat attaatccta gcaatggtgg tactaactac     180
aatgagaagt tcaagagcag agccaccatg accaggaca cgtccacgag cacagcctac      240
atggagctga gcagcctgag atctgaggac acggccgtgt attactgtga actgatgcag      300
ggctactggg gccagggaac actagtcaca gtctcctca                            339

<210> SEQ ID NO 51
<211> LENGTH: 339
<212> TYPE: DNA
<213> ORGANISM: Artificial Sequence
<220> FEATURE:
<223> OTHER INFORMATION: Humanized antibody construct comprising
      sequences from mus musculus and homo sapiens

<400> SEQUENCE: 51
caggtgcagc tggtgcagtc tggggctgag gtgaagaagc ctggggcctc agtgaaggtt      60
tcctgcaagg catctggata caccttcacc agctactgga tgcactgggt gaaacagcga     120
cctggacaag ggcttgagtg gatcggaaat attaatccta gcaatggtgg tactaactac     180
aatgagaagt tcaagagcaa agccaccctc accgtcgaca atccacgag cacagcctac      240 atggagctga gcagcctgag atctgaggac acggccgtgt attactgtga actgatgcag      300
ggctactggg gccagggaac actagtcaca gtctcctca                            339

<210> SEQ ID NO 52
<211> LENGTH: 339
<212> TYPE: DNA

<213> ORGANISM: Artificial Sequence
<220> FEATURE:
<223> OTHER INFORMATION: Humanized antibody construct comprising
      sequences from mus musculus and homo sapiens

<400> SEQUENCE: 52

```
caggtgcagc tggtgcagtc tggggctgag gtgaagaagc ctggggcctc agtgaaggtt      60
tcctgcaagg catctggata caccttcacc agctactgga tgcactgggt gcgacaggcc     120
cctggacaag ggcttgagtg gatcggaaat attaatccta gcaatggtgg tactaactac     180
aatgagaagt tcaagagcaa ggccaccatg accagggaca cgtccacgag cacagcctac     240
atggagctga gcagcctgag atctgaggac acggccgtgt attactgtga actgatgcag     300
ggctactggg gccagggaac actagtcaca gtctcctca                            339
```

<210> SEQ ID NO 53
<211> LENGTH: 462
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 53

```
Met Gly Trp Ser Cys Ile Ile Leu Phe Leu Val Ala Thr Ala Thr Gly
 1               5                   10                  15

Val His Ser Gln Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
         35                  40                  45

Thr Ser Tyr Trp Met His Trp Val Arg Gln Ala Pro Gly Gln Gly Leu
     50                  55                  60

Glu Trp Ile Gly Asn Ile Asn Pro Ser Asn Gly Gly Thr Asn Tyr Asn
 65                  70                  75                  80

Glu Lys Phe Lys Ser Arg Ala Thr Met Thr Arg Asp Thr Ser Thr Ser
                 85                  90                  95

Thr Ala Tyr Met Glu Leu Ser Ser Leu Arg Ser Glu Asp Thr Ala Val
            100                 105                 110

Tyr Tyr Cys Glu Leu Met Gln Gly Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
                245                 250                 255

Leu Phe Pro Pro Lys Pro Lys Asp Thr Leu Met Ile Ser Arg Thr Pro
            260                 265                 270
```

```
Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
        290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
450                 455                 460

<210> SEQ ID NO 54
<211> LENGTH: 462
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 54

Met Gly Trp Ser Cys Ile Ile Leu Phe Leu Val Ala Thr Ala Thr Gly
 1               5                  10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Asn Ile Asn Pro Ser Asn Gly Gly Thr Asn Tyr Asn
65                  70                  75                  80

Glu Lys Phe Lys Ser Lys Ala Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Glu Leu Met Gln Gly Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175
```

```
Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 55
<211> LENGTH: 462
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 55

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Met His Trp Val Arg Gln Ala Pro Gly Gln Gly Leu
    50                  55                  60

Glu Trp Ile Gly Asn Ile Asn Pro Ser Asn Gly Gly Thr Asn Tyr Asn
65                  70                  75                  80
```

Glu Lys Phe Lys Ser Lys Ala Thr Met Thr Arg Asp Thr Ser Thr Ser
                    85                  90                  95

Thr Ala Tyr Met Glu Leu Ser Ser Leu Arg Ser Glu Asp Thr Ala Val
            100                 105                 110

Tyr Tyr Cys Glu Leu Met Gln Gly Tyr Trp Gly Gln Gly Thr Leu Val
        115                 120                 125

Thr Val Ser Ser Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
450                 455                 460

<210> SEQ ID NO 56
<211> LENGTH: 1389
<212> TYPE: DNA
<213> ORGANISM: Artificial Sequence
<220> FEATURE:
<223> OTHER INFORMATION: Humanized antibody construct comprising sequences from mus musculus and homo sapiens

<400> SEQUENCE: 56

| | |
|---|---|
| atgggatgga gctgtatcat cctcttcttg gtagcaacag ctacaggtgt ccactcccag | 60 |
| gtgcagctgg tgcagtctgg ggctgaggtg aagaagcctg gggcctcagt gaaggtttcc | 120 |
| tgcaaggcat ctggatacac cttcaccagc tactggatgc actgggtgcg acaggcccct | 180 |
| ggacaagggc ttgagtggat cggaaatatt aatcctagca atggtggtac taactacaat | 240 |
| gagaagttca gagcagagc caccatgacc agggacacgt ccacgagcac agcctacatg | 300 |
| gagctgagca gcctgagatc tgaggacacg gccgtgtatt actgtgaact gatgcagggc | 360 |
| tactggggcc agggaacact agtcacagtc tcctcagcct ccaccaaggg cccatcggtc | 420 |
| ttccccctgg cacctcctc caagagcacc tctgggggca gcggccct gggctgcctg | 480 |
| gtcaaggact acttccccga accggtgacg gtgtcgtgga actcaggcgc cctgaccagc | 540 |
| ggcgtgcaca ccttcccggc tgtcctacag tcctcaggac tctactccct cagcagcgtg | 600 |
| gtgaccgtgc cctccagcag cttgggcacc cagacctaca tctgcaacgt gaatcacaag | 660 |
| cccagcaaca ccaaggtgga caagaaagtt gagcccaaat cttgtgacaa aactcacaca | 720 |
| tgcccaccgt gcccagcacc tgaactcgcg gggcaccgt cagtcttcct cttccccca | 780 |
| aaacccaagg acaccctcat gatctcccgg acccctgagg tcacatgcgt ggtggtggac | 840 |
| gtgagccacg aagaccctga ggtcaagttc aactggtacg tggacggcgt ggaggtgcat | 900 |
| aatgccaaga caaagccgcg ggaggagcag tacaacagca cgtaccgtgt ggtcagcgtc | 960 |
| ctcaccgtcc tgcaccagga ctggctgaat ggcaaggagt acaagtgcaa ggtctccaac | 1020 |
| aaagccctcc cagcccccat cgagaaaacc atctccaaag ccaaagggca gccccgagaa | 1080 |
| ccacaggtgt acaccctgcc cccatcccgg gatgagctga ccaagaacca ggtcagcctg | 1140 |
| acctgcctgg tcaaaggctt ctatcccagc gacatcgccg tggagtggga gagcaatggg | 1200 |
| cagccggaga acaactacaa gaccacgcct cccgtgctgg actccgacgg ctccttcttc | 1260 |
| ctctacagca agctcaccgt ggacaagagc aggtggcagc aggggaacgt cttctcatgc | 1320 |
| tccgtgatgc atgaggctct gcacaaccac tacacgcaga agagcctctc cctgtctccg | 1380 |
| ggtaaatga | 1389 |

<210> SEQ ID NO 57
<211> LENGTH: 1389
<212> TYPE: DNA
<213> ORGANISM: Artificial Sequence
<220> FEATURE:
<223> OTHER INFORMATION: Humanized antibody construct comprising
      sequences from mus musculus and homo sapiens

<400> SEQUENCE: 57

| | |
|---|---|
| atgggatgga gctgtatcat cctcttcttg gtagcaacag ctacaggtgt ccactcccag | 60 |
| gtgcagctgg tgcagtctgg ggctgaggtg aagaagcctg gggcctcagt gaaggtttcc | 120 |
| tgcaaggcat ctggatacac cttcaccagc tactggatgc actgggtgaa acagcgacct | 180 |
| ggacaagggc ttgagtggat cggaaatatt aatcctagca atggtggtac taactacaat | 240 |
| gagaagttca gagcaaagc caccctcacc gtcgacaaat ccacgagcac agcctacatg | 300 |
| gagctgagca gcctgagatc tgaggacacg gccgtgtatt actgtgaact gatgcagggc | 360 |
| tactggggcc agggaacact agtcacagtc tcctcagcct ccaccaaggg cccatcggtc | 420 |
| ttccccctgg cacctcctc caagagcacc tctgggggca gcggccct gggctgcctg | 480 |
| gtcaaggact acttccccga accggtgacg gtgtcgtgga actcaggcgc cctgaccagc | 540 |

```
ggcgtgcaca ccttcccggc tgtcctacag tcctcaggac tctactccct cagcagcgtg    600
gtgaccgtgc cctccagcag cttgggcacc cagacctaca tctgcaacgt gaatcacaag    660
cccagcaaca ccaaggtgga caagaaagtt gagcccaaat cttgtgacaa aactcacaca    720
tgcccaccgt gcccagcacc tgaactcgcg ggggcaccgt cagtcttcct cttccccca     780 aaacccaagg acaccctcat gatctcccgg acccctgagg tcacatgcgt ggtggtggac    840
gtgagccacg aagaccctga ggtcaagttc aactggtacg tggacggcgt ggaggtgcat    900
aatgccaaga caaagccgcg ggaggagcag tacaacagca cgtaccgtgt ggtcagcgtc    960
ctcaccgtcc tgcaccagga ctggctgaat ggcaaggagt acaagtgcaa ggtctccaac   1020
aaagccctcc cagcccccat cgagaaaacc atctccaaag ccaaagggca gccccgagaa   1080
ccacaggtgt acaccctgcc cccatcccgg gatgagctga ccaagaacca ggtcagcctg   1140
acctgcctgg tcaaaggctt ctatcccagc gacatcgccg tggagtggga gagcaatggg   1200
cagccggaga caaactacaa gaccacgcct cccgtgctgg actccgacgg ctccttcttc   1260
ctctacagca agctcaccgt ggacaagagc aggtggcagc aggggaacgt cttctcatgc   1320
tccgtgatgc atgaggctct gcacaaccac tacacgcaga agagcctctc cctgtctccg   1380
ggtaaatga                                                           1389
```

<210> SEQ ID NO 58
<211> LENGTH: 1389
<212> TYPE: DNA
<213> ORGANISM: Artificial Sequence
<220> FEATURE:
<223> OTHER INFORMATION: Humanized antibody construct comprising
      sequences from mus musculus and homo sapiens

<400> SEQUENCE: 58

```
atgggatgga gctgtatcat cctcttcttg gtagcaacag ctacaggtgt ccactcccag     60
gtgcagctgg tgcagtctgg ggctgaggtg aagaagcctg ggcctcagt gaaggtttcc    120 tgcaaggcat ctggatacac cttcaccagc tactggatgc actgggtgcg acaggcccct    180
ggacaagggc ttgagtggat cggaaatatt aatcctagca atggtggtac taactacaat    240
gagaagttca gagcaaggc caccatgacc agggacacgt ccacgagcac agcctacatg    300
gagctgagca gcctgagatc tgaggacacg gccgtgtatt actgtgaact gatgcagggc    360
tactgggccc agggaacact agtcacagtc tcctcagcct ccaccaaggg cccatcggtc    420
ttccccctgg caccctcctc caagagcacc tctggggggca gcggccct gggctgcctg    480 gtcaaggact acttccccga accggtgacg gtgtcgtgga actcaggcgc cctgaccagc    540
ggcgtgcaca ccttcccggc tgtcctacag tcctcaggac tctactccct cagcagcgtg    600
gtgaccgtgc cctccagcag cttgggcacc cagacctaca tctgcaacgt gaatcacaag    660
cccagcaaca ccaaggtgga caagaaagtt gagcccaaat cttgtgacaa aactcacaca    720
tgcccaccgt gcccagcacc tgaactcgcg ggggcaccgt cagtcttcct cttccccca     780 aaacccaagg acaccctcat gatctcccgg acccctgagg tcacatgcgt ggtggtggac    840
gtgagccacg aagaccctga ggtcaagttc aactggtacg tggacggcgt ggaggtgcat    900
aatgccaaga caaagccgcg ggaggagcag tacaacagca cgtaccgtgt ggtcagcgtc    960
ctcaccgtcc tgcaccagga ctggctgaat ggcaaggagt acaagtgcaa ggtctccaac   1020
aaagccctcc cagcccccat cgagaaaacc atctccaaag ccaaagggca gccccgagaa   1080
ccacaggtgt acaccctgcc cccatcccgg gatgagctga ccaagaacca ggtcagcctg   1140
```

```
acctgcctgg tcaaaggctt ctatcccagc gacatcgccg tggagtggga gagcaatggg    1200
cagccggaga caactacaa gaccacgcct cccgtgctgg actccgacgg ctccttcttc    1260
ctctacagca agctcaccgt ggacaagagc aggtggcagc aggggaacgt cttctcatgc    1320
tccgtgatgc atgaggctct gcacaaccac tacacgcaga gagcctctc cctgtctccg    1380 ggtaaatga                                                            1389
```

```
<210> SEQ ID NO 59
<211> LENGTH: 462
<212> TYPE: PRT
<213> ORGANISM: Artificial Sequence
<220> FEATURE:
<223> OTHER INFORMATION: Chimaeric antibody construct comprising
      sequences from mus musculus and homo sapiens

<400> SEQUENCE: 59
```

```
Met Gly Trp Ser Cys Ile Ile Leu Phe Leu Val Ala Ala Thr Gly
 1               5                  10                  15

Val His Ser Gln Val Gln Leu Gln Gln Pro Gly Thr Glu Leu Val Lys
                20                  25                  30

Pro Gly Ala Ser Val Lys Leu Ser Cys Lys Ala Ser Gly Tyr Thr Phe
            35                  40                  45

Thr Ser Tyr Trp Met His Trp Val Lys Gln Arg Pro Gly Gln Gly Leu
    50                  55                  60

Glu Trp Ile Gly Asn Ile Asn Pro Ser Asn Gly Thr Asn Tyr Asn
65                  70                  75                  80

Glu Lys Phe Lys Ser Lys Ala Thr Leu Thr Val Asp Lys Ser Ser
                85                  90                  95

Thr Ala Tyr Met Gln Leu Ser Ser Leu Thr Ser Glu Asp Ser Ala Val
                100                 105                 110

Tyr Tyr Cys Glu Leu Met Gln Gly Tyr Trp Gly Gln Gly Thr Leu Val
            115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Ala Gly Ala Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320
```

```
Leu Thr Val Leu His Gln Asp Trp Leu Asn Gly Lys Glu Tyr Lys Cys
            325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
    450                 455                 460

<210> SEQ ID NO 60
<211> LENGTH: 12
<212> TYPE: PRT
<213> ORGANISM: Homo Sapiens

<400> SEQUENCE: 60

Val Leu Pro Asp Ile Val Met Glu Ala Pro Leu Asn
1               5                   10

<210> SEQ ID NO 61
<211> LENGTH: 113
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
            35                  40                  45

Gly Asn Ile Asn Pro Ser Asn Gly Gly Thr Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Glu Leu Gly Gln Ser Tyr Trp Gly Gln Gly Thr Leu Val Thr Val Ser
            100                 105                 110

Ser

<210> SEQ ID NO 62
<211> LENGTH: 4
<212> TYPE: PRT
<213> ORGANISM: Artificial Sequence
<220> FEATURE:
<223> OTHER INFORMATION: Humanized antibody construct comprising
```

-continued sequences from mus musculus and homo sapiens

<400> SEQUENCE: 62

Gly Gln Ser Tyr
1

<210> SEQ ID NO 63
<211> LENGTH: 113
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Ile
            35                  40                  45

Gly Asn Ile Asn Pro Ser Asn Gly Gly Thr Asn Tyr Asn Glu Lys Phe
        50                  55                  60

Lys Ser Arg Ala Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Glu Leu Gly Gln Ser Tyr Trp Gly Gln Gly Thr Leu Val Thr Val Ser
            100                 105                 110

Ser

<210> SEQ ID NO 64
<211> LENGTH: 113
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Asn Ile Asn Pro Ser Asn Gly Gly Thr Asn Tyr Asn Glu Lys Phe
        50                  55                  60

Lys Ser Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Glu Leu Gly Gln Ser Tyr Trp Gly Gln Gly Thr Leu Val Thr Val Ser
            100                 105                 110

Ser

<210> SEQ ID NO 65
<211> LENGTH: 113
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Asn Ile Asn Pro Ser Asn Gly Gly Thr Asn Tyr Asn Glu Lys Phe
    50                  55                  60

Lys Ser Lys Ala Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Glu Leu Gly Gln Ser Tyr Trp Gly Gln Gly Thr Leu Val Thr Val Ser
            100                 105                 110

Ser

<210> SEQ ID NO 66
<211> LENGTH: 113
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Asn Ile Asn Pro Ser Asn Gly Gly Thr Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Glu Leu Met Gln Gly Tyr Trp Gly Gln Gly Thr Leu Val Thr Val Ser
            100                 105                 110

Ser

<210> SEQ ID NO 67
<211> LENGTH: 112
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 67

Asp Ile Val Met Thr Gln Ser Pro Leu Ser Leu Pro Val Thr Leu Gly
1               5                   10                  15

Gln Pro Ala Ser Ile Ser Cys Arg Ser Ser Lys Ser Leu Leu Tyr Lys
            20                  25                  30

Asp Gly Lys Thr Tyr Leu Asn Trp Phe Arg Gln Arg Pro Gly Gln Ser
            35                  40                  45

Pro Gln Leu Leu Ile Tyr Leu Met Ser Thr Arg Ala Ser Gly Val Pro
    50                  55                  60

Asp Arg Phe Ser Gly Gly Gly Ser Gly Thr Asp Phe Thr Leu Lys Ile
65                  70                  75                  80

Ser Arg Val Glu Ala Glu Asp Val Gly Val Tyr Tyr Cys Gln Gln Leu
                85                  90                  95

Val Glu Tyr Pro Leu Thr Phe Gly Gln Gly Thr Lys Leu Glu Ile Lys
            100                 105                 110

<210> SEQ ID NO 68
<211> LENGTH: 112
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 68

Asp Ile Val Met Thr Gln Ser Pro Leu Ser Leu Pro Val Thr Leu Gly
1               5                   10                  15

Gln Pro Ala Ser Ile Ser Cys Arg Ser Ser Lys Ser Leu Leu Tyr Lys
            20                  25                  30

Asp Gly Lys Thr Tyr Leu Asn Trp Phe Gln Gln Arg Pro Gly Gln Ser
            35                  40                  45

Pro Arg Leu Leu Ile Tyr Leu Met Ser Thr Arg Ala Ser Gly Val Pro
    50                  55                  60

Asp Arg Phe Ser Gly Gly Gly Ser Gly Thr Asp Phe Thr Leu Lys Ile
65                  70                  75                  80

Ser Arg Val Glu Ala Glu Asp Val Gly Val Tyr Tyr Cys Gln Gln Leu
                85                  90                  95

Val Glu Tyr Pro Leu Thr Phe Gly Gln Gly Thr Lys Leu Glu Ile Lys
            100                 105                 110

<210> SEQ ID NO 69
<211> LENGTH: 112
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 69

Asp Ile Val Met Thr Gln Ser Pro Leu Ser Leu Pro Val Thr Leu Gly
1               5                   10                  15

Gln Pro Ala Ser Ile Ser Cys Arg Ser Ser Lys Ser Leu Leu Tyr Lys
            20                  25                  30

Asp Gly Lys Thr Tyr Leu Asn Trp Phe Arg Gln Arg Pro Gly Gln Ser
            35                  40                  45

Pro Arg Leu Leu Ile Tyr Leu Met Ser Thr Arg Ala Ser Gly Val Pro
    50                  55                  60

Asp Arg Phe Ser Gly Gly Gly Ser Gly Thr Asp Phe Thr Leu Lys Ile
65                  70                  75                  80

Ser Arg Val Glu Ala Glu Asp Val Gly Val Tyr Tyr Cys Gln Gln Leu
                85                  90                  95

Val Glu Tyr Pro Leu Thr Phe Gly Gln Gly Thr Lys Leu Glu Ile Lys
            100                 105                 110

```
<210> SEQ ID NO 70
<211> LENGTH: 112
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 70

Asp Ile Val Met Thr Gln Ser Pro Leu Ser Asn Pro Val Thr Leu Gly
 1               5                  10                  15

Gln Pro Val Ser Ile Ser Cys Arg Ser Ser Lys Ser Leu Leu Tyr Lys
            20                  25                  30

Asp Gly Lys Thr Tyr Leu Asn Trp Phe Arg Gln Arg Pro Gly Gln Ser
        35                  40                  45

Pro Gln Leu Leu Ile Tyr Leu Met Ser Thr Arg Ala Ser Gly Val Pro
    50                  55                  60

Asp Arg Phe Ser Gly Gly Gly Ser Gly Thr Asp Phe Thr Leu Lys Ile
65                  70                  75                  80

Ser Arg Val Glu Ala Glu Asp Val Gly Val Tyr Tyr Cys Gln Gln Leu
                85                  90                  95

Val Glu Tyr Pro Leu Thr Phe Gly Gln Gly Thr Lys Leu Glu Ile Lys
            100                 105                 110

<210> SEQ ID NO 71
<211> LENGTH: 112
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 71

Asp Ile Val Met Thr Gln Ser Pro Leu Ser Asn Pro Val Thr Leu Gly
 1               5                  10                  15

Gln Pro Val Ser Ile Ser Cys Arg Ser Ser Lys Ser Leu Leu Tyr Lys
            20                  25                  30

Asp Gly Lys Thr Tyr Leu Asn Trp Phe Leu Gln Arg Pro Gly Gln Ser
        35                  40                  45

Pro Arg Leu Leu Ile Tyr Leu Met Ser Thr Arg Ala Ser Gly Val Pro
    50                  55                  60

Asp Arg Phe Ser Gly Gly Gly Ser Gly Thr Asp Phe Thr Leu Lys Ile
65                  70                  75                  80

Ser Arg Val Glu Ala Glu Asp Val Gly Val Tyr Tyr Cys Gln Gln Leu
                85                  90                  95

Val Glu Tyr Pro Leu Thr Phe Gly Gln Gly Thr Lys Leu Glu Ile Lys
            100                 105                 110

<210> SEQ ID NO 72
<211> LENGTH: 112
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 72

Asp Ile Val Met Thr Gln Ser Pro Leu Ser Asn Pro Val Thr Leu Gly
 1               5                  10                  15

Gln Pro Val Ser Ile Ser Cys Arg Ser Ser Lys Ser Leu Leu Tyr Lys
            20                  25                  30
```

```
Asp Gly Lys Thr Tyr Leu Asn Trp Phe Arg Gln Arg Pro Gly Gln Ser
         35                  40                  45

Pro Arg Leu Leu Ile Tyr Leu Met Ser Thr Arg Ala Ser Gly Val Pro
     50                  55                  60

Asp Arg Phe Ser Gly Gly Ser Gly Thr Asp Phe Thr Leu Lys Ile
 65                  70                  75                  80

Ser Arg Val Glu Ala Glu Asp Val Gly Val Tyr Tyr Cys Gln Gln Leu
                 85                  90                  95

Val Glu Tyr Pro Leu Thr Phe Gly Gln Gly Thr Lys Leu Glu Ile Lys
             100                 105                 110
```

<210> SEQ ID NO 73
<211> LENGTH: 16
<212> TYPE: PRT
<213> ORGANISM: Homo Sapiens

<400> SEQUENCE: 73

```
Thr Pro Ser Pro Val Leu Pro Asp Ile Val Met Glu Ala Pro Leu Asn
 1               5                  10                  15
```

<210> SEQ ID NO 74
<211> LENGTH: 16
<212> TYPE: PRT
<213> ORGANISM: Homo sapiens

<400> SEQUENCE: 74

```
Val Leu Pro Asp Ile Val Met Glu Ala Pro Leu Asn Ser Ala Val Pro
 1               5                  10                  15
```

<210> SEQ ID NO 75
<211> LENGTH: 4
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 75

```
Arg Gln Gly Tyr
 1
```

<210> SEQ ID NO 76
<211> LENGTH: 4
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 76

```
Ile Gln Gly Tyr
 1
```

<210> SEQ ID NO 77
<211> LENGTH: 4
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 77

```
Gly Asp Gly Tyr
 1
```

```
<210> SEQ ID NO 78
<211> LENGTH: 4
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 78

Gly Ile Gly Tyr
 1

<210> SEQ ID NO 79
<211> LENGTH: 4
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 79

Gly Ser Gly Tyr
 1

<210> SEQ ID NO 80
<211> LENGTH: 4
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 80

Gly Gln Asn Tyr
 1

<210> SEQ ID NO 81
<211> LENGTH: 4
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 81

Gly Gln Tyr Tyr
 1

<210> SEQ ID NO 82
<211> LENGTH: 4
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 82

Gly Gln Leu Tyr
 1

<210> SEQ ID NO 83
<211> LENGTH: 4
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 83
```

```
Gly Gln Phe Tyr
 1

<210> SEQ ID NO 84
<211> LENGTH: 4
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 84

Gly Gln Gly Trp
 1

<210> SEQ ID NO 85
<211> LENGTH: 16
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 85

Tyr Glu Ser Ile Lys His Glu Pro Glu Asn Pro Pro Tyr Glu Glu
 1               5                  10                  15

<210> SEQ ID NO 86
<211> LENGTH: 4
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 86

Trp Gln Gly Tyr
 1

<210> SEQ ID NO 87
<211> LENGTH: 4
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 87

Gly Ala Gly Tyr
 1

<210> SEQ ID NO 88
<211> LENGTH: 4
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 88

Gly Leu Gly Tyr
 1

<210> SEQ ID NO 89
<211> LENGTH: 4
<212> TYPE: PRT
<213> ORGANISM: Artificial Sequence
<220> FEATURE:
<223> OTHER INFORMATION: Humanized antibody construct comprising
```

-continued sequences from mus musculus and homo sapiens

<400> SEQUENCE: 89

Gly Val Gly Tyr
1

<210> SEQ ID NO 90
<211> LENGTH: 4
<212> TYPE: PRT
<213> ORGANISM: Artificial Sequence
<220> FEATURE:
<223> OTHER INFORMATION: Humanized antibody construct comprising
      sequences from mus musculus and homo sapiens

<400> SEQUENCE: 90

Gly Gln Trp Tyr
1

<210> SEQ ID NO 91
<211> LENGTH: 438
<212> TYPE: PRT
<213> ORGANISM: Saimiri boliviensis

<400> SEQUENCE: 91

Met Ser Pro Ile Leu Gly Tyr Trp Lys Ile Lys Gly Leu Val Gln Pro
1               5                   10                  15

Thr Arg Leu Leu Leu Glu Tyr Leu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Glu Val Leu
    210                 215                 220

Phe Gln Gly Pro Leu Gly Ser Met Gln Glu Ser Leu Tyr Pro Val Ala
225                 230                 235                 240

Gln Leu Cys Pro Ser Phe Glu Ser Glu Ala Thr Pro Ser Pro Val
                245                 250                 255

Leu Pro Asp Ile Val Met Glu Ala Pro Leu Asn Ser Ala Val Pro Ser
            260                 265                 270

```
Ala Val Ala Ser Ala Val Gln Pro Ser Leu Ser Pro Leu Glu Ala Ser
            275                 280                 285

Ser Val Asn Tyr Glu Ser Val Lys His Glu Pro Glu Asn Pro Pro Pro
    290                 295                 300

Tyr Glu Glu Ala Met Asn Val Ser Leu Lys Lys Val Ser Gly Ile Lys
305                 310                 315                 320

Glu Glu Ile Lys Glu Pro Glu Ser Ile Lys Ala Ala Val Gln Glu Thr
                325                 330                 335

Glu Ala Pro Tyr Ile Ser Ile Ala Cys Asp Leu Ile Lys Glu Thr Lys
                340                 345                 350

Leu Ser Ala Glu Pro Thr Pro Asp Phe Ser Asn Tyr Ser Glu Met Ala
            355                 360                 365

Lys Val Glu Gln Pro Leu Pro Asp His Ser Glu Ile Val Glu Asp Ser
370                 375                 380

Ser Pro Asp Ser Glu Pro Val Asp Leu Phe Ser Asp Ser Ile Pro
385                 390                 395                 400

Asp Val Pro Gln Lys Gln Asp Glu Ala Val Ile Leu Val Lys Glu Asn
                405                 410                 415

Leu Thr Glu Thr Ser Phe Glu Ser Met Ile Glu His Glu Asn Lys Leu
            420                 425                 430

Glu Arg Pro His Arg Asp
        435
```

<210> SEQ ID NO 92
<211> LENGTH: 460
<212> TYPE: PRT
<213> ORGANISM: Macaca fascicularis

<400> SEQUENCE: 92

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205
```

```
Thr Phe Gly Gly Gly Asp His Pro Pro Lys Ser Asp Leu Glu Val Leu
    210                 215                 220

Phe Gln Gly Pro Leu Gly Ser Lys Met Asp Leu Val Gln Thr Ser Glu
225                 230                 235                 240

Val Met Gln Glu Ser Leu Tyr Pro Ala Ala Gln Leu Cys Pro Ser Phe
                245                 250                 255

Glu Glu Ser Glu Ala Thr Pro Ser Pro Val Leu Pro Asp Ile Val Met
            260                 265                 270

Glu Ala Pro Leu Asn Ser Ala Val Pro Ser Ala Gly Ala Ser Ala Val
        275                 280                 285

Gln Pro Ser Ser Ser Pro Leu Glu Ala Ser Ser Val Asn Tyr Glu Ser
    290                 295                 300

Ile Ile His Glu Pro Glu Asn Pro Pro Tyr Glu Glu Ala Met Ser
305                 310                 315                 320

Val Ser Leu Lys Lys Val Ser Gly Ile Lys Glu Ile Lys Glu Pro
                325                 330                 335

Glu Ser Ile Asn Ala Ala Val Gln Glu Thr Glu Ala Pro Tyr Ile Ser
            340                 345                 350

Ile Ala Cys Asp Leu Ile Lys Glu Thr Lys Leu Ser Ala Glu Pro Thr
        355                 360                 365

Pro Asp Phe Ser Asp Tyr Ser Glu Met Ala Lys Val Glu Gln Pro Val
370                 375                 380

Pro Asp His Ser Glu Leu Val Glu Asp Ser Ser Pro Asp Ser Glu Pro
385                 390                 395                 400

Val Asp Leu Phe Ser Asp Ser Ile Pro Asp Val Pro Gln Lys Gln
                405                 410                 415

Asp Glu Ala Val Met Leu Val Lys Glu Asn Leu Pro Gly Thr Ser Phe
        420                 425                 430

Glu Ser Met Ile Glu His Glu Asn Lys Glu Lys Leu Ser Ala Leu Pro
    435                 440                 445

Pro Glu Gly Gly Ser Ser Gly Arg Ile Val Thr Asp
    450                 455                 460

<210> SEQ ID NO 93
<211> LENGTH: 438
<212> TYPE: PRT
<213> ORGANISM: Callithrix jacchus

<400> SEQUENCE: 93

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125
```

```
Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Glu Val Leu
    210                 215                 220

Phe Gln Gly Pro Leu Gly Ser Val Gln Asp Ser Leu Cys Pro Val Ala
225                 230                 235                 240

Gln Leu Cys Pro Ser Phe Glu Glu Ser Glu Ala Thr Pro Ser Pro Val
                245                 250                 255

Leu Pro Asp Ile Val Met Glu Ala Pro Leu Asn Ser Ala Val Pro Ser
            260                 265                 270

Ala Gly Ala Ser Ala Val Gln Pro Ser Ser Ser Pro Leu Glu Ala Ser
        275                 280                 285

Ser Val Asn Phe Glu Ser Val Lys His Glu Pro Glu Asn Pro Pro
    290                 295                 300

Tyr Glu Glu Ala Met Asn Val Ser Arg Lys Lys Val Ser Gly Ile Lys
305                 310                 315                 320

Glu Glu Ile Lys Glu Pro Glu Ser Ile Asn Ala Ala Val Gln Glu Thr
                325                 330                 335

Glu Ala Pro Tyr Ile Ser Ile Ala Cys Asp Leu Ile Lys Glu Thr Lys
            340                 345                 350

Leu Ser Ala Glu Pro Thr Pro Asp Phe Ser Ser Tyr Ser Glu Met Ala
        355                 360                 365

Lys Val Glu Gln Pro Leu Pro Asp His Ser Glu Leu Val Glu Asp Ser
    370                 375                 380

Ser Pro Asp Ser Glu Pro Val Asp Leu Phe Ser Asp Ser Ile Pro
385                 390                 395                 400

Asp Val Pro Gln Lys Gln Asp Glu Ala Val Ile Leu Val Lys Glu Thr
                405                 410                 415

Leu Thr Glu Thr Ser Phe Glu Ser Met Ile Glu His Glu Asn Lys Leu
            420                 425                 430

Glu Arg Pro His Arg Asp
        435

<210> SEQ ID NO 94
<211> LENGTH: 432
<212> TYPE: PRT
<213> ORGANISM: Rattus rattus

<400> SEQUENCE: 94

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60
```

```
Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Glu Val Leu
210                 215                 220

Phe Gln Gly Pro Leu Gly Ser Ile Gln Glu Ser Leu Tyr Pro Thr Ala
225                 230                 235                 240

Gln Leu Cys Pro Ser Phe Glu Ala Glu Ala Thr Pro Ser Pro Val
                245                 250                 255

Leu Pro Asp Ile Val Met Glu Ala Pro Leu Asn Ser Leu Leu Pro Ser
            260                 265                 270

Ala Gly Ala Ser Val Val Gln Pro Ser Val Ser Pro Leu Glu Ala Pro
        275                 280                 285

Pro Pro Val Ser Tyr Asp Ser Ile Lys Leu Glu Pro Glu Asn Pro Pro
290                 295                 300

Pro Tyr Glu Glu Ala Met Asn Val Ala Leu Lys Ala Leu Gly Thr Lys
305                 310                 315                 320

Glu Gly Ile Lys Glu Pro Glu Ser Phe Asn Ala Ala Val Gln Glu Thr
                325                 330                 335

Glu Ala Pro Tyr Ile Ser Ile Ala Cys Asp Leu Ile Lys Glu Thr Lys
            340                 345                 350

Leu Ser Thr Glu Pro Ser Pro Asp Phe Ser Asn Tyr Ser Glu Ile Ala
        355                 360                 365

Lys Phe Glu Lys Ser Val Pro Glu His Ala Glu Leu Val Glu Asp Ser
370                 375                 380

Ser Pro Glu Ser Glu Pro Val Asp Leu Phe Ser Asp Asp Ser Ile Pro
385                 390                 395                 400

Glu Val Pro Gln Thr Gln Glu Glu Ala Val Met Leu Met Lys Glu Ser
                405                 410                 415

Leu Thr Glu Val Ser Glu Thr Val Ala Gln His Lys Glu Glu Arg Leu
            420                 425                 430

<210> SEQ ID NO 95
<211> LENGTH: 6
<212> TYPE: PRT
<213> ORGANISM: Homo Sapiens

<400> SEQUENCE: 95

Asp Glu Thr Phe Ala Leu
 1               5
```

```
<210> SEQ ID NO 96
<211> LENGTH: 6
<212> TYPE: PRT
<213> ORGANISM: Homo Sapiens

<400> SEQUENCE: 96

Glu Leu Ser Lys Thr Ser
 1               5
```